US010555989B2

(12) United States Patent
Hashimoto-Torii et al.

(10) Patent No.: US 10,555,989 B2
(45) Date of Patent: Feb. 11, 2020

(54) TREATMENT OF LEARNING DISABILITIES AND OTHER NEUROLOGICAL DISORDERS WITH SK CHANNEL INHIBITOR(S)

(71) Applicant: Children's National Medical Center, Washington, DC (US)

(72) Inventors: Kazue Hashimoto-Torii, Bethesda, MD (US); Masaaki Torii, Bethesda, MD (US); Mohammad Shahid, Hyattsville, MD (US); Hiroki Morizono, Washington, DC (US)

(73) Assignee: Children's National Medical Center, Washington, DC (US)

( * ) Notice: Subject to any disclaimer, the term of this patent is extended or adjusted under 35 U.S.C. 154(b) by 0 days.

(21) Appl. No.: 15/767,361

(22) PCT Filed: Oct. 13, 2016

(86) PCT No.: PCT/US2016/056835
§ 371 (c)(1),
(2) Date: Apr. 11, 2018

(87) PCT Pub. No.: WO2017/066444
PCT Pub. Date: Apr. 20, 2017

(65) Prior Publication Data
US 2018/0280472 A1     Oct. 4, 2018

Related U.S. Application Data

(60) Provisional application No. 62/240,561, filed on Oct. 13, 2015.

(51) Int. Cl.
| | |
|---|---|
| A61K 38/00 | (2006.01) |
| A61K 38/17 | (2006.01) |
| A61P 25/28 | (2006.01) |
| A61K 9/00 | (2006.01) |
| A61K 45/06 | (2006.01) |

(52) U.S. Cl.
CPC ........ *A61K 38/1767* (2013.01); *A61K 9/0085* (2013.01); *A61K 45/06* (2013.01); *A61P 25/28* (2018.01)

(58) Field of Classification Search
None
See application file for complete search history.

(56) References Cited

U.S. PATENT DOCUMENTS

| | | |
|---|---|---|
| 2011/0009330 A1 | 1/2011 | Hartmann et al. |
| 2014/0356343 A1 | 12/2014 | Chase et al. |

FOREIGN PATENT DOCUMENTS

| | | |
|---|---|---|
| WO | WO 2010/015037 A1 | 2/2010 |

OTHER PUBLICATIONS

International Search Report and Written Opinion dated Jan. 30, 2017 in PCT/US2016/056835 filed Oct. 13, 2016.
Emre, M., "Dementia associated with Parkinson's disease", The Lancet Neurology, Apr. 2003, vol. 2, pp. 229-237.
Ramadoss, J. et al., "Acid-sensitive channel inhibition prevents fetal alcohol spectrum disorders cerebellar Purkinje cell loss", American Journal of Physiology, Regulatory, Integrative and Comparative Physiology, Aug. 2008, vol. 295, No. 2, pp. 1-14.
Fakira, A. K. et al., "Increased SK2 channel-mediated negative feedback on NMDAR impairs synaptic plasticity following context-dependent sensitization to morphine", Biological Psychiatry, Jan. 15, 2014, vol. 75, No. 2, pp. 1-19.
Pedarzani, P. et al., "Tamapin, a Venom Peptide from the Indian Red Scorpion (*Mesobuthus tamulus*) That Targets Small Conductance $Ca^{2+}$-activated $K^+$ channels and Afterhyperpolarization Currents in Central Neurons", The Journal of Biological Chemistry, Nov. 29, 2002, vol. 227, No. 48, 10 total pages.
Pedarzani, P. et al., "Control of Electrical Activity in Central Neurons by Modulating the Gating of Small Conductance $Ca^{2+}$-activated $K^+$ Channels", The Journal of Biological Chemistry, Mar. 30, 2011, vol. 276, No. 13, 9 total pages.
Clusin, W. T., "Calcium-activated Ion Currents in Heart Failure and Ischemia: Point Counter Point", Journal of Cardiovascular Disorders, Sep. 19, 2014, vol. 1, No. 1, pp. 1-5.
Allen, D. et al., "SK2 channels are neuroprotective for ischemia-induced neuronal cell death", Journal of Cerebral Blood Flow & Metabolism, Jun. 29, 2011, vol. 31, pp. 2302-2312.
Extended European Search Report dated Apr. 29, 2019 in corresponding European Patent Application No. 16856191.8, 8 pages.
Jenny Lam, MD, et al.,"The Therapeutic Potential of Small-Conductance KCa2 Channels in Neurodegenerative and Psychiatric Diseases", Expert Opinion Therapeutic Targets, vol. 17, No. 10, XP055582092, Jul. 25, 2013, 26 pages.
Frederic W. Hopf et al., "The SK Channel as a Novel Target for Treating Alcohol Use Disorders", Channels, vol. 5, No. 4, XP055582096, Jul. 30, 2011, pp. 289-292 and cover page.

*Primary Examiner* — Olga N Chernyshev
(74) *Attorney, Agent, or Firm* — Oblon, McClelland, Maier & Neustadt, L.L.P.

(57) ABSTRACT

Methods for treating learning disabilities associated with fetal alcohol syndrome and other neurological disorders by administering SK channel blockers, antagonists, inhibitors or modifiers like tamapin.

10 Claims, 5 Drawing Sheets

Specification includes a Sequence Listing.

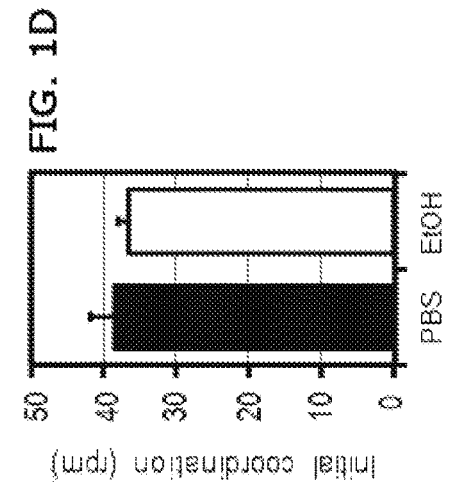
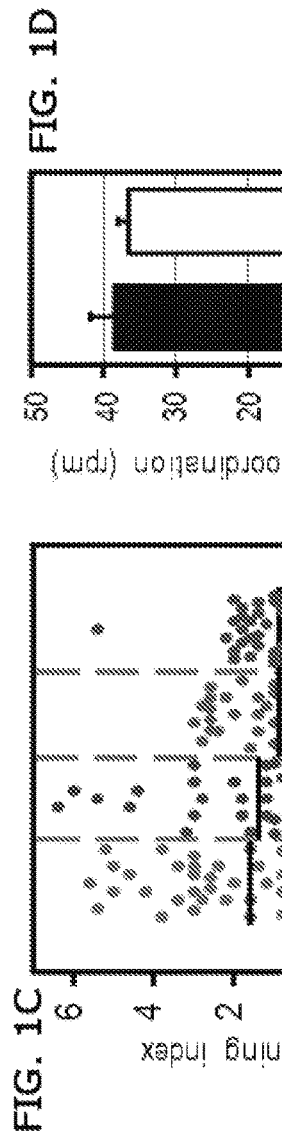
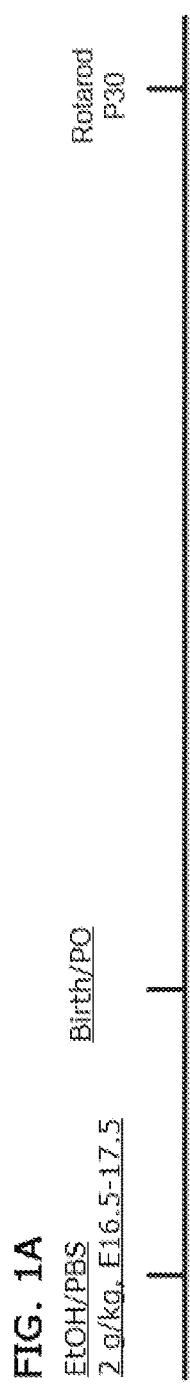
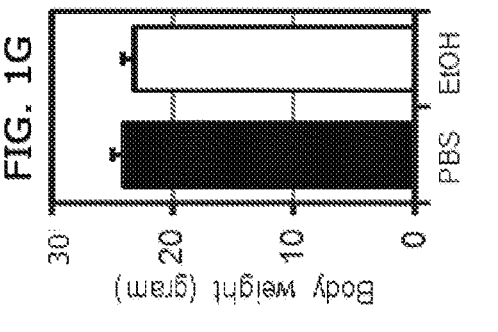
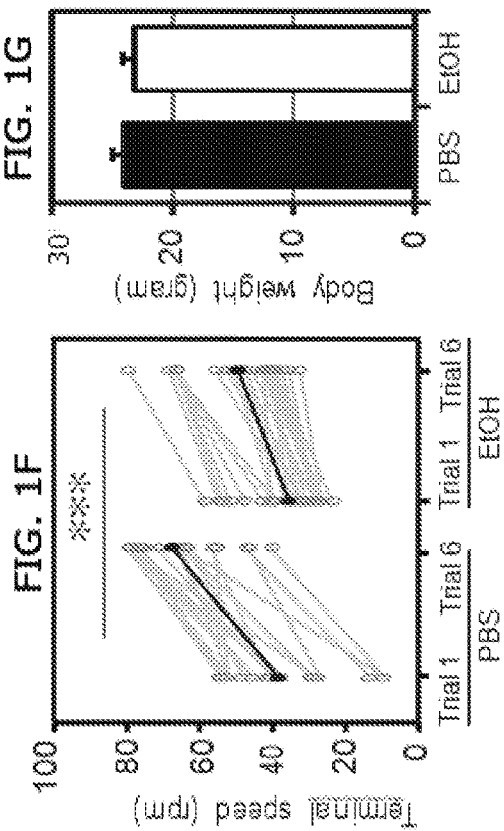
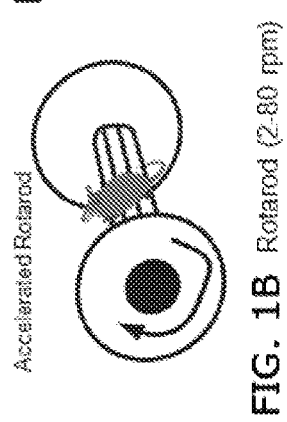
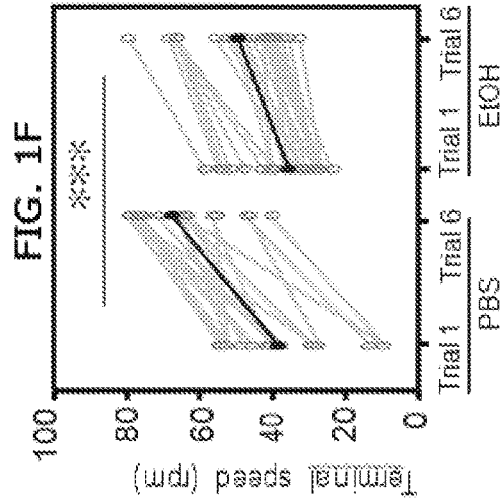

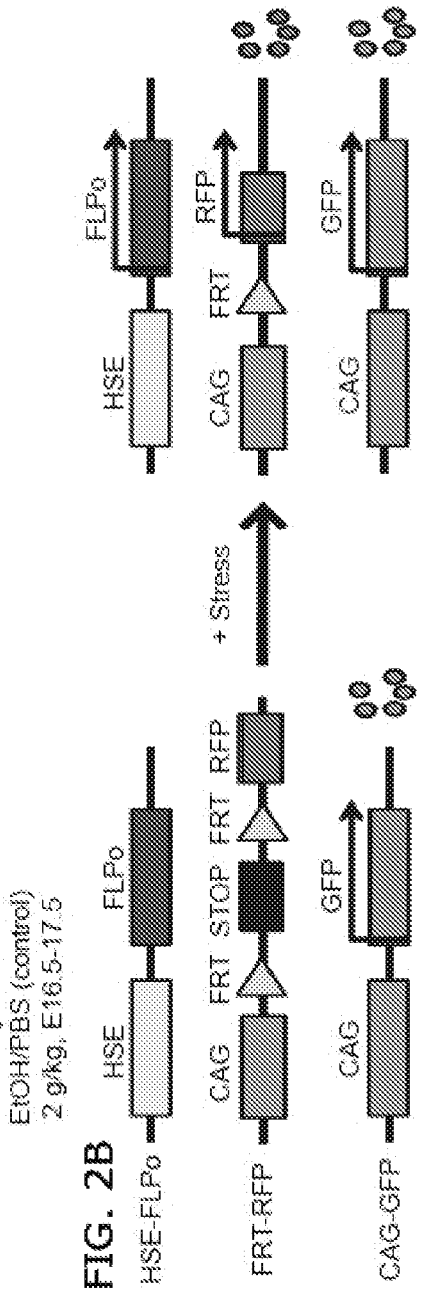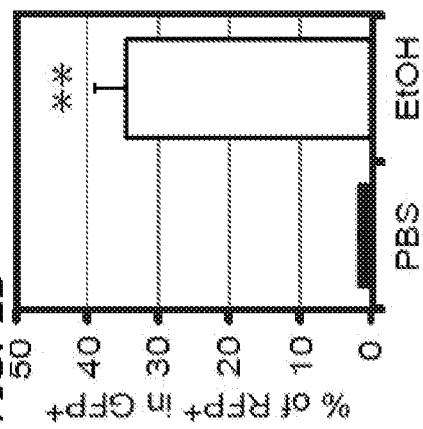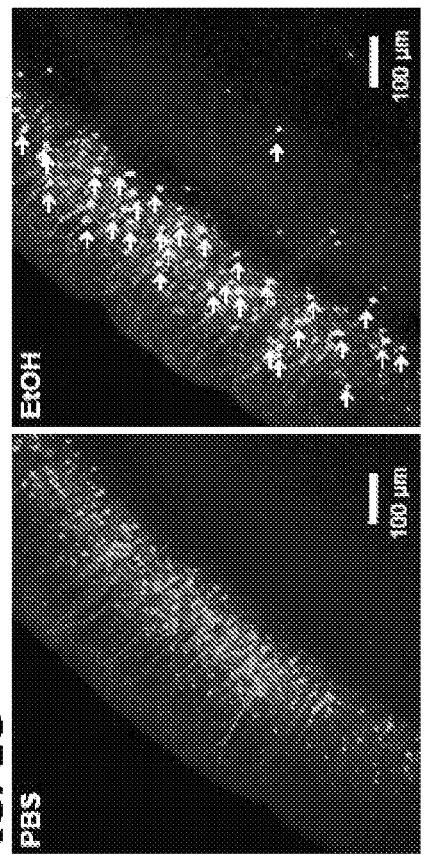

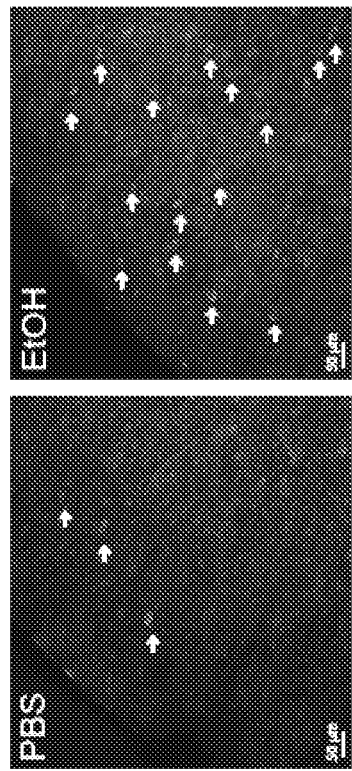
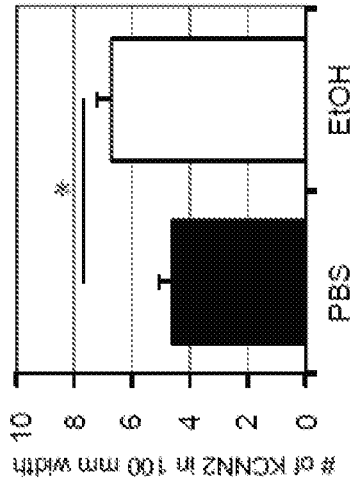
FIG. 3A
FIG. 3B
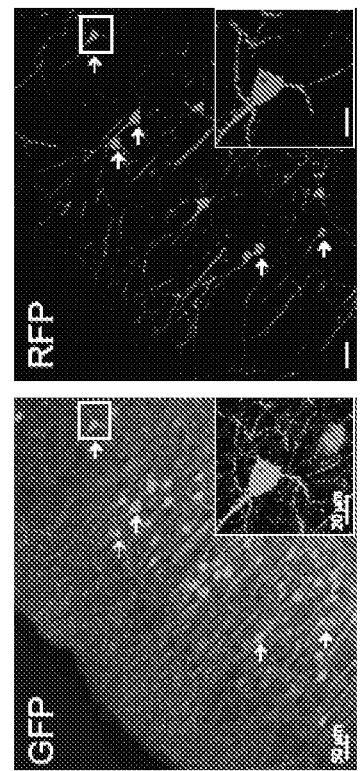
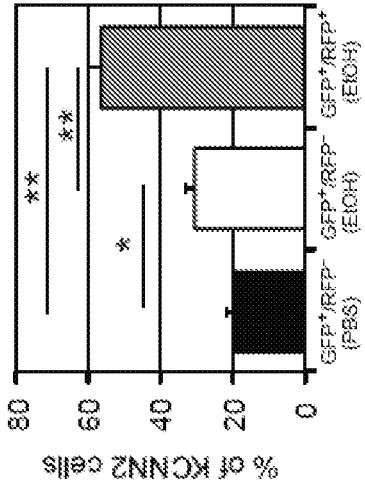
FIG. 3C
FIG. 3D
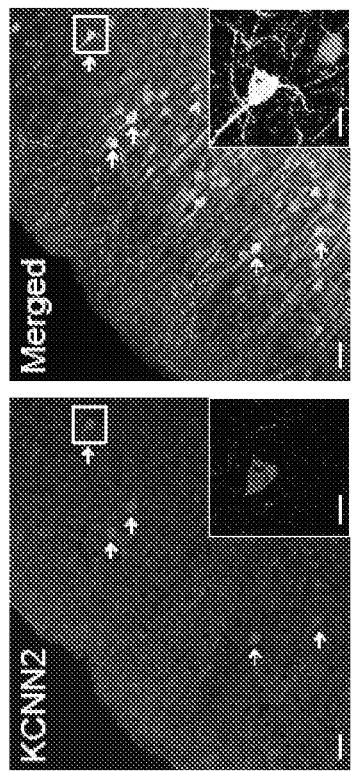
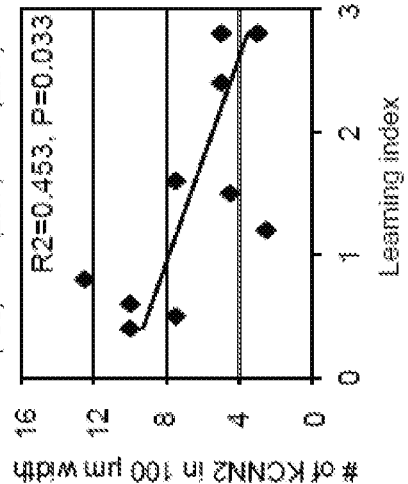
FIG. 3E

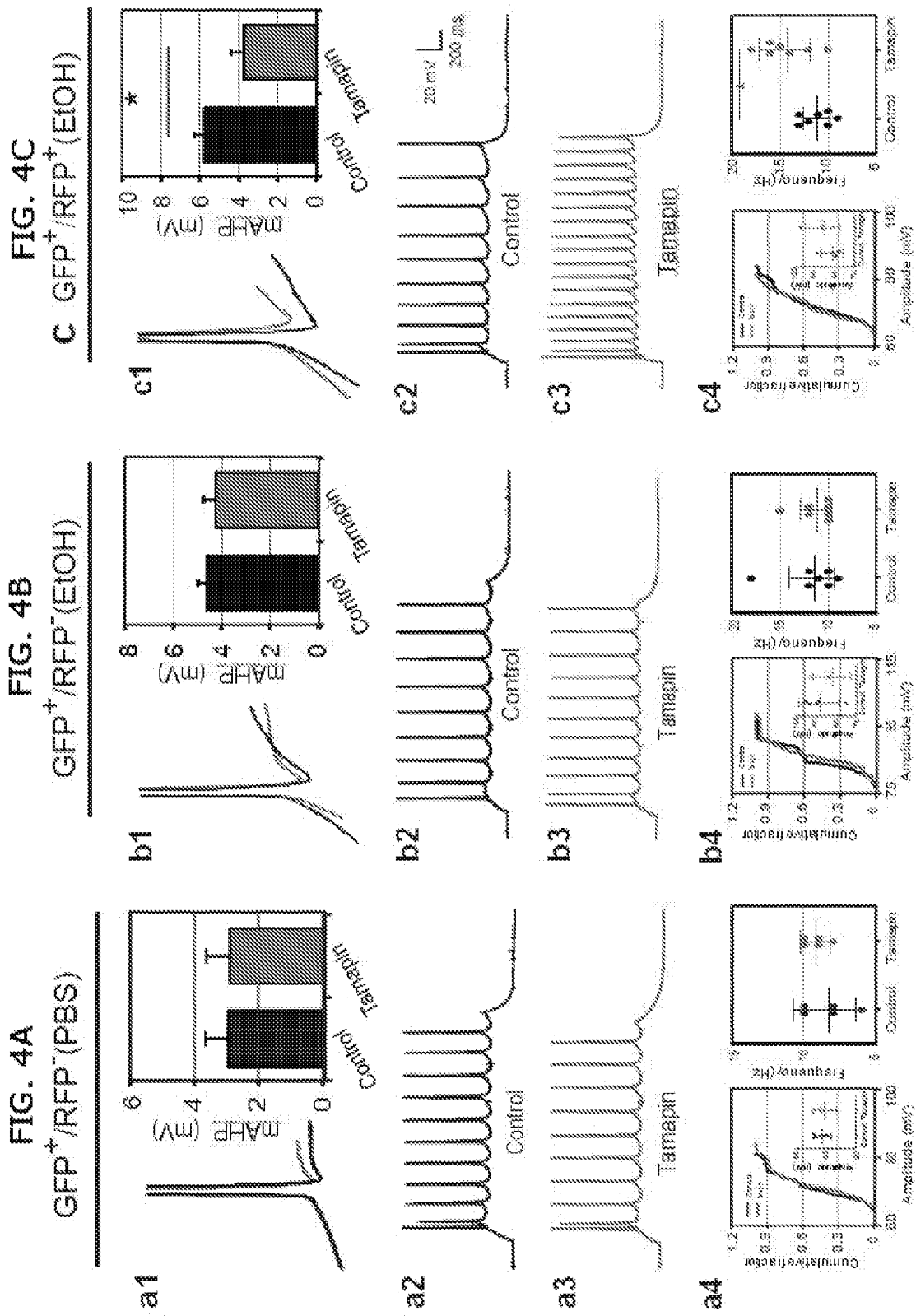

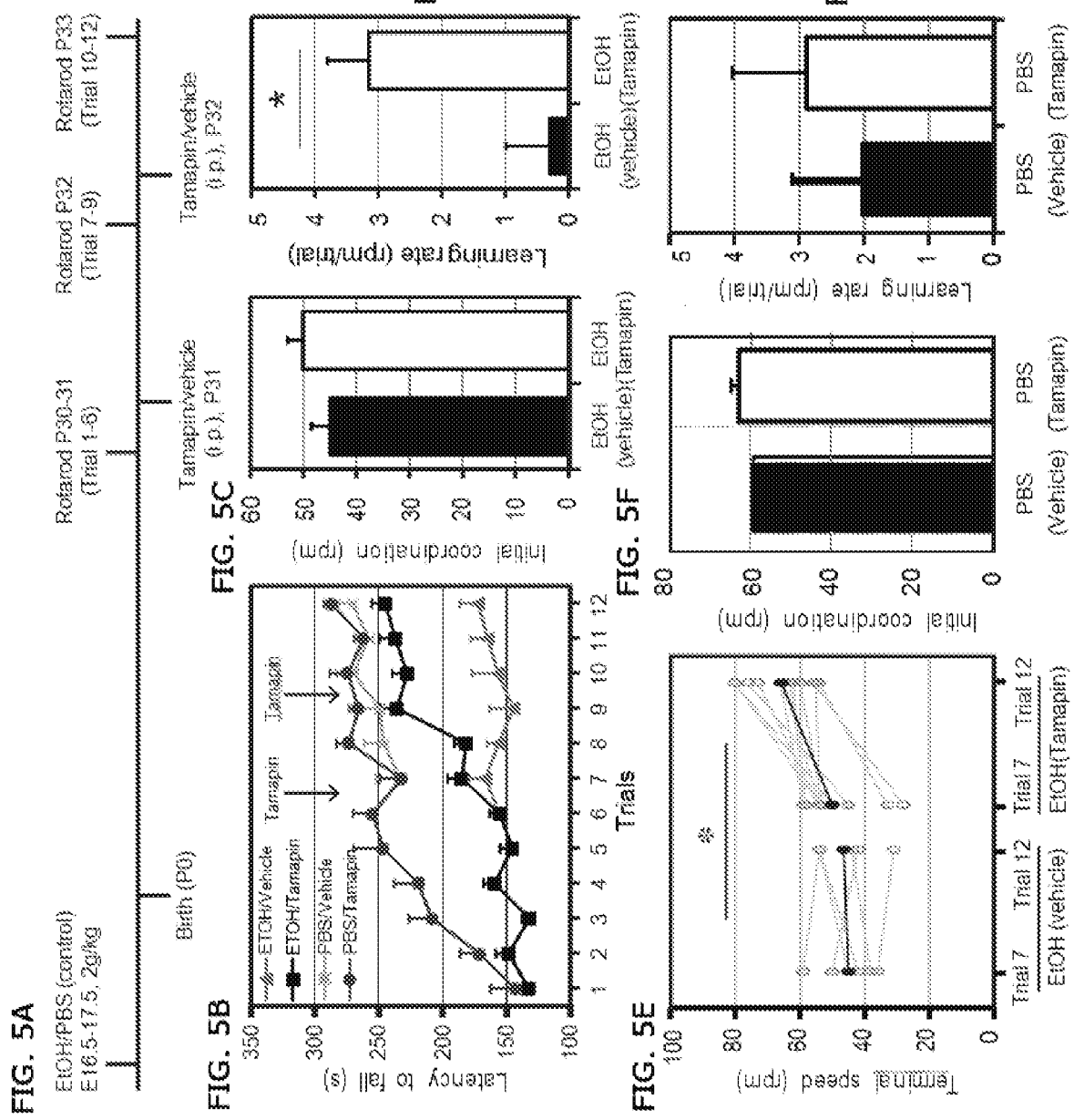

TREATMENT OF LEARNING DISABILITIES AND OTHER NEUROLOGICAL DISORDERS WITH SK CHANNEL INHIBITOR(S)

CROSS-REFERENCE TO RELATED APPLICATIONS

This application claims benefit of U.S. Provisional Application No. 62/240,561, filed Oct. 13, 2015 which is hereby incorporated by reference in its entirety.

STATEMENT REGARDING FEDERALLY SPONSORED RESEARCH OR DEVELOPMENT

This invention was made with government support under National Institute of Health grant R00 AA018387/AA/NIAAA. The government may have certain rights in the invention.

BACKGROUND OF THE INVENTION

Field of the Invention

The invention involves prevention, amelioration or treatment of learning disabilities or other neurological disorders or diseases, such as those associated with fetal alcohol syndrome (FAS), by administering a SK2 channel or other SK channel inhibitor. Exposure of the brain, such as a developing fetal brain, to alcohol or other harmful agents or conditions, causes learning disabilities that persist and can present life-long challenges for an individual so exposed. The inventors have found that such learning disabilities caused by stressors like alcohol exposure in utero, can be treated by administering a SK channel blocker, antagonist, inhibitor or modifier, such as the SK2 channel blocker tamapin which is a short peptide found in scorpion venom.

Description of the Related Art

The CDC estimates that 0.2 to 1.5 infants for every 1,000 live births have fetal alcohol syndrome (FAS) caused by exposure of the fetus in utero to alcohol. It estimates the lifetime cost for one individual with FAS to be $2 million dollars and the total cost to the U.S. to be $4 billion annually. Maternal alcohol consumption is the most commonly identifiable non-genetic cause of mental retardation or learning disability and damage to the brain associated with FAS. Ethanol is a common environmental toxin known to have age dependent effects on brain development and behavior. The cardinal features of intrauterine fetal exposure to EtOH include microcephaly, dysmorphic features, intellectual disability, and executive and behavioral dysfunction. In view of the significant consequences and costs, there is a need to identify prophylactic agents that ameliorate ethanol associated damage the brain and nervous system of a fetus as well as to treat such damage once it occurs, for example, in a neonate or child.

With this objective in mind, and based on earlier work involving heat shock protein expression described in U.S. Provisional Application No. 62/240,561 (herein incorporated by reference), the inventors sought to investigate brain injury acquired during fetal development and early life. They investigated mechanisms of injury, whether particular injuries correlate with learning disabilities, as well as specific factors or agents that might modify or mitigate injury or serve as post-injury interventions or treatments.

Tamapin is a short polypeptide toxin isolated from the Indian Red Scorpion (*Mesobuthus tamalus*) and is known to be a selective blocker of SK2 channels. A SK2 channel, also known as a KCNN2 or $K_{Ca}2.2$ channel, is a potassium intermediate/small conductance calcium-activated channel, subfamily N, member 2. SK2 is an ion channel protein that is activated before membrane hyperpolarization and is thought to regulate neuronal excitability by contributing to the slow component of synaptic afterhyperpolarization (AHP); see KCNN2 potassium calcium-activated channel subfamily N member 2, Gene ID: 3781, full report, updated 9 Oct. 2016, available at: https://_www.ncbi.nlm.nih.gov/gene?Db=gene&Cmd=ShowDetailView&TermToSearch=3781 (last accessed Oct. 11, 2016) which is hereby incorporated by reference.

The SK2 channel has not previously been associated with learning disabilities caused by fetal exposure to alcohol.

BRIEF DESCRIPTION OF THE DRAWINGS

FIG. 1 describes impaired motor skill learning in the mice exposed to EtOH at prenatal stages. FIG. 1A: Timeline of the experiment. FIG. 1B: Experimental paradigm of accelerated rotarod tests. FIG. 1C: Learning rates of EtOH-exposed mice are decreased compared to those of PBS-exposed mice both in males and females. F (1,185)=16.37, P<0.0001 by two-way ANOVA, P<0.05 by post hoc Tukey's test. The interaction between the sex (male: M or female: F) and exposure type (PBS or EtOH) was not observed. F (1,185)=0.014, P=0.9073 by post hoc Tukey's test (n=50, 35, 50 and 50 for PBS M, PBS F, EtOH M and EtOH F, respectively). FIG. 1D: The initial motor coordination (terminal speed at trial 1) was not affected by EtOH exposure. P=0.579 by Student's t-test (n=20: PBS and 44: EtOH). FIG. 1E: EtOH-exposed mice show shorter latency to fall after multiple trials, indicating impaired motor learning compared to controls (n=20: PBS and 44: EtOH, P=0.0001 by repeated-measure ANOVA. P=0.0001 by Kolmogorov-Smirnov test). FIG. 1F: Gray lines show the terminal speed on rotarod at trials 1 and 6 for individual mice. The solid lines indicate the means. ***P<0.0001 by Student's t-test (n=20: PBS and 26: EtOH). 1G: The body weight is not affected by EtOH-exposure. P=0.433 by Student's t-test (n=12: PBS and 12: EtOH).

FIG. 2 shows that Heat Shock reporter system for long-term labeling of the cells responded to prenatal alcohol exposure. FIG. 2A: Timeline of the experiment. FIG. 2B: Design of the heat shock signaling reporter construct. FIG. 2C: RFP reporter expression in $GFP^+$ electroporated cells in the M1 cortex of the mice prenatally exposed to PBS or EtOH. FIG. 2D: The Percentage of $RFP^+$ cells in $GFP^+$ cells. **P=0.0003 by Student's t-test (n=10: PBS and 10: EtOH).

FIG. 3 describes the increase of KCNN2-expressing pyramidal neurons in M1 cortex correlates with the severity of motor learning deficits in mice prenatally exposed to EtOH. FIG. 3A: KCNN2 expression in layers II/III in M1 cortex in P30 mice. White arrows indicate the $KCNN2^|$ cells. FIG. 3B: Quantification of $KCNN2^|$ cells in layers II/III in M1 cortex in PBS- and EtOH-exposed mice. More $KCNN2^+$ cells were observed in EtOH-exposed mice. * P=0.006 by Student's t-test (n=16: PBS and 16: EtOH). FIG. 3C: KCNN2 expression enriched in $RFP^+$ pyramidal neurons in layers II/III in M1 cortex in EtOH-exposed mice (insets show the higher magnification view of the squared areas). FIG. 3D: The percentages of $KCNN2^+$ neurons in $GFP^+/RFP^-$ cells in PBS (black)- or EtOH (white)-exposed mice and $GFP^+/RFP^+$ cells in EtOH-exposed (gray) mice. F (2, 34)=3 8.40, **P<0.01, *P<0.05 by posthoc Tukey's test. FIG. 3E: Pearson's correlation analysis revealed the negative correlation between the learning index and the number of KCNN2$^+$ cells in layers II/IIII in M1 cortex. (R=0.453, P=0.033).

FIG. 4 shows that a KCNN2 antagonist affects the medium AHP in reporter-positive pyramidal neurons in M1. Each of FIGS. 4A, 4B and 4C comprises four vertically arranged panels which are sublabeled a, b, c and d.

FIGS. 4A-4C: KCNN2 antagonist (tamapin, 100 nM)-sensitive afterhyperpolarization (mAHP) examined in PBS- or EtOH-exposed GFP$^+$/RFP$^+$ or GFP$^+$/RFP$^-$ neurons as indicated. The blockage of EtOH-induced KCNN2 overexpression by Tamapin in RFP$^+$ neurons reduced the mAHP (FIG. 4C, panel c1) (*P=0.009 by Student's t-test) and increased the firing frequency (FIG. 4C, panels c2 and c3). Tamapin showed no significant effects on RFP$^-$ neurons in PBS- or EtOH-exposed brains (FIGS. 4A-4B, panels a1-b3). FIG. 4A-4C, panels a4-c4, left graph: Cumulative distributions of the amplitude of action potential and the mean amplitude of action potentials (insets) recorded from control (black)- and Tamapin (light gray)-stimulated neurons. FIGS. 44-4C, panels a4-c4, right graph: Firing frequencies, showing significant increase in RFP$^+$ neurons. *P=0.016 by Student's t-test.

FIG. 5 shows that a KCNN2 antagonist improves motor skill learning in mice exposed to EtOH prenatally. FIG. 5A: Timeline of the experiment. FIG. 5B: The mice were tested for the motor learning before and after the Tamapin injection (i.p.). Tamapin improved the motor learning in the EtOH-exposed mice (trial 7-12). P=0.0001 by repeated-measure ANOVA, P=0.0001 by Kolmogorov-Smirnov test. The latency to fall at the first trial followed by injection (trial 7) is similar between vehicle and Tamapin in both PBS-exposed and EtOH-exposed groups (P=0.302 and 0.960 by Student's t-test, respectively). FIG. 5C: The initial motor coordination was not affected by Tamapin in EtOH-exposed mice. FIG. 5D: Motor leaning (trial 7-12) was rescued in Tamapin-injected EtOH-exposed mice. *P=0.015 by Student's t-test. FIG. 5E: The performance of individual mice (gray lines) on rotarod at the beginning (trail 7) and the end of Tamapin injection (trial 12). The solid lines indicate the means. *P=0.015 by Student's t-test (n=12: PBS and 7: EtOH). FIG. 5F: The initial motor coordination was not affected by Tamapin in PBS-exposed mice. FIG. 5G: No effects of Tamapin on motor learning were observed in PBS-exposed mice (trial 7-12), P=0.596 by Student's t-test.

DETAILED DESCRIPTION OF THE INVENTION

As demonstrated herein, the inventors have found that compounds, such as tamapin, that block, antagonize, inhibit or modify SK receptor numbers or SK receptor activity in the nervous system can protect and treat a subject, such as a fetus in utero or a neonate from the negative effects of exposure to ethanol or other stressors. Non-limiting aspects and applications of these findings include the following.

A method for treating a subject having, or at risk of acquiring a brain injury during fetal development comprising administering an inhibitor of at least one SK channel, such as tamapin or a tamapin analog that blocks, antagonizes, inhibits or modifies the SK2 channel. The subject may be fetus, such as a first, second, or third trimester fetus in utero, a pregnant woman, a preterm infant, neonate, child or adult at risk of acquiring injury to the brain or nervous system, especially, a fetus, preterm infant, or child whose brain is growing or developing and thus is susceptible to disruptions to growth or development associated with overexpression or over-activity of a SK channel compared to a corresponding normal individual. A SK channel blocker can physically block a channel comprising a SK protein; a SK channel inhibitor or antagonist, which may also be a channel blocker, inhibits or antagonizes activity associated with a SK channel such as ion transport or signal transduction; a SK channel modifier modifies the structure of a SK channel, e.g., by allosteric effects, or modifies at least one activity associated with a SK channel. These compounds may selectively or predominantly block or act on one kind of SK channel or act block or act on different SK channels, such as on channels comprising SK1 (KCNN1) and/or SK2 (KCNN2) and/or SK3 (KCNN3) and/or SK4 (KCNN4) proteins.

A subject may also be one who is at risk, who has been diagnosed to be at risk, or who has fetal alcohol syndrome or damage to the brain or nervous system associated with exposure to alcohol, drugs or other agents or conditions that increase SK channel protein expression or activity. A subject also, specifically, includes a pregnant woman who carries a subject in need of treatment. A subject is preferably a human; however, the invention also includes treatment of other mammalian or animal subjects who express SK or SK-like channel proteins, including canines, felines, equines, simians and other valuable or commercially raised animals.

Advantageously, the method comprises administering tamapin or another SK channel blocker, antagonist, inhibitor or modifier to the subject, optionally, along with a carrier or excipient. Other active ingredients may be coadministered before, at the same time, or after the SK channel inhibitor. One or more SK inhibitors may be administered or a SK inhibitor that inhibits more than one type of SK channel may be selected.

The invention also involves a method for treating a learning disability associated with fetal alcohol syndrome or for treating another learning disability, neurological disease, disorder or condition, comprising administering tamapin or a tamapin analog or at least one other SK channel inhibitor to a subject in need thereof. A subject may be one having a learning disability such as cognitive dysfunction, intellectual disability, dyspraxia, or mental retardation. A subject may also have another disease, disorder or condition associated with fetal alcohol syndrome, a fetal alcohol spectrum disorder, have been exposed in utero to a drug or other toxic agent, such as one inducing or triggering the expression of at least one heat shock protein. In one embodiment the subject is a fetal subject exposed to alcohol or agent(s) or condition(s) that increase the expression or activity of SK2 (KCNN2) channel or another SK channel protein such as SK1, SK3, or SK4 in utero.

SK channel blockers, antagonists, inhibitors and modifiers include tamapin, Lei-dab7, Apamin, Scyllatoxin or analog(s) thereof. Other SK channel blockers include Dequalinium, d-Tubocurarine, UC1-1684, UCL-1848, Cyproheptadine, Fluoxetine, NS8593, Scyllatoxin (Leiurotoxin-I), Lei-Dab7, N-methyl-laudanosine, N-Me-bicuculline, Pancuronium, Atracurium, 1-ethyl-1H-benzo[d]imidazol-2(3H)-on, 6,7-dichloro-3-(hydroxyimino)indolin-2-one, N-cyclohexyl-2-(3,5-dimethyl-1H-pyrazol-1-yl)-6-methyl-pyrimidin-4-amine, and (R)—N-(1,2,3,4-tetrahydronaphthalen-1-yl)-1H-benzo[d]imidazol-2-amine. Such blockers, antagonists, inhibitors or modifiers may act reversibly or irreversibly.

In one embodiment methods according to the invention will administer tamapin or a tamapin analog to a subject, such as a subject in utero or to another subject in need thereof. Tamapin or a tamapin analog may be administered to a fetus who has been exposed to alcohol, ischemia or to at least one agent or condition that increases the expression or activity of SK2 channel or another SK channel in cells of the nervous system compared to those in a normal subject not exposed to alcohol, ischemia, or said at least one agent. A therapeutic amount of tamapin or tamapin analog within a suitable therapeutic range for a particular subject may be selected by one skilled in the art. For example, a dosage sufficient to expose SK receptors in neurons or other cells of the nervous system to a concentration of 24 pM to 1 nM tamapin or tamapin analog may be administered.

In some embodiments of the invention, tamapin analogs will be administered to a subject in need thereof. Such analogs include Tamapin isotype 2, peptides having 1, 2, 3, 4, 5, 6, 7, 8, 9, 10 or more substitutions, deletions or additions to a native tamapin sequence as well as the specific analogs described in Table 1. Preferably, a tamapin derivative or analog will retain at least one functional property of native tamapin, such as the ability to block, antagonize, inhibit, or modify a SK channel or SK channel activity, block in a reversible manner SK2 channels with selectivity for SK2 channels over SK1 channels, block SK2 channels with higher affinity than SK3 channels and SK4 channels (affinity for SK2 channel>SK3>SK1>SK4), exhibit activity that is not voltage dependent, or induce cellular uptake, inactivation, recycling or destruction of SK channels.

Examples of tamapin derivatives are peptides of not more than 50 amino acids in length that have the ability to bind to SK2-type channels and affect the ability of those channel classes to transport ions, for example, to decrease their ability to transport ions. Tamapin derivatives and analogs include those which show specific and definable binding properties to all and/or certain subclasses of SK2-type channels. Such analogs or derivatives also include peptides whose sequences can be generated by using any combination of subparts of the peptides listed below using recombinant DNA techniques or chemical synthesis (e.g., peptide synthesis).

The native tamapin peptide, tamapin isotype 2, as well as tamapin derivatives or analogs in which amino acid changes can be engineered based on combinatorial fusion/shuffling of the amino acid sequences described in Table 1. For example, a shuffled variant can comprise residues (1 to n) of a first sequence selected from Table 1 and residues n+1 to 31) of a second sequence selected from Table 1, where n is 2 to 30. Similar shuffling among 3 or more variants may also be used to derive a new variant or a longer peptide construct comprising a new variant.

The analogs described in Table 1 as well as combinatorial variants thereof may comprise additional amino acid residues or other moieties at the N or C termini, for example, sequences or moieties that improve stability of tamapin or its analog in the blood or its other pharmacokinetic properties or sequences or moieties which target or facilitate passage of tamapin or its analogs into the brain or nervous system tissues. Combinatorial fusion of these sequences may be performed suing standard molecular biology techniques or by chemical synthesis such as peptide synthesis. Further modifications to tamapin or its derivatives or analogs include addition of linker peptides, effector moieties, or other covalent modifications, such as insertion or addition of non-natural amino acids (e.g., D-amino acids, or D- or L-amino acids other than the conventional twenty amino acids), use of modified or functionalized amino acids, or replacement of amino acids in the sequence with other chemical compounds.

Another aspect of the invention involves a method for treating a neurological disease, disorder or condition, comprising administering tamapin or a tamapin analog or at least one other SK channel inhibitor to a subject in need thereof. Such a method may, but need not be, directed to a subject having or at risk of having a learning disability. For example, such a method may be practiced with a subject having Alzheimer's disease or other dementia, neurofibromatosis, Angelman syndrome or another neurological disease, disorder or condition associated with aberrant expression of SK channels. Disease, disorders or conditions associated with stress, injury, insult or ischemia may also be mentioned when associated with the over-expression or over-activity of at least one SK channel in the cells of the nervous system compared to those of a normal individual. Such channels include SK1, SK2, SK3 and SK4 type channels.

A subject who has been exposed to (or is at risk of exposure to) agent(s) or condition(s) that increase the expression or activity of SK2 channel or another SK channel in cells of the nervous system compared to those of a normal individual may be selected for treatment. A fetal subject or a subject of any age who has been exposed to alcohol, drugs, toxins, poisons, or other chemical agents that increase the expression or activity of SK2 channel or another SK channel in cells of the nervous system compared to those of a normal individual may be selected. A fetal subject or subject of any age who has been exposed to prions, viruses, bacteria, yeast, fungi or other microbes, immunogens, allergens, or autoantigens that increase the expression or activity of SK2 channel or another SK channel in cells of the nervous system compared to those of a normal individual may be selected. A subject who has undergone surgery, injury, trauma or ischemia that that increases the expression or activity of a SK2 channel or another SK channel in cells of the nervous system compared to those of a normal or control individual may be selected.

Such subjects may be administered one or more channel blockers, inhibitors or modifiers for a SK channel including those for a SK1, SK2, SK3, and/or SK4 channel, advantageously in a form that reaches a target tissue expressing SK channels. In some embodiments, tamapin, a tamapin analog or one or more SK2 channel blockers, inhibitors or modifiers will be administered. Such SK2 channel blockers, inhibitors or modifiers may be selective for, or predominantly block SK2 channels. Alternatively, they may also block other kinds of SK channels.

In embodiments of the invention, a subject may be a fetal subject or a subject of any age, such as first, second or third trimester human fetus, neonate, toddler, child, pre-teen, preadolescent, adolescent or other individual with a developing, growing, reorganizing or remodeling nervous system. Subjects having diseases, disorders or conditions that caused by, are characterized by, or otherwise associated with over-expression or over-activity of SK channel proteins or with epigenetic changes to the nervous system, including obesity, alcohol, drug or other substance abuse or addiction, cardiovascular disease, diabetes, arthritis, and autoimmune diseases may benefit from administration of a SK channel blocker, antagonist, inhibitor or modifier.

Normal subjects who are at risk of, or who expect to be exposed to, alcohol, drugs, inhalants, chemical agents, biological agents, antigens, allergens, toxins, radiation, X-ray, UV, physical agents, physical, mental or psychological stress, post-traumatic stress, athletic or occupational injury or stress, battlefield injury or stress, or other conditions that increase the expression of or activity of, a SK channel in the brain or nervous system may also benefit from administration of a SK channel blocker, antagonist, inhibitor or modifier either prophylactically (before), currently with, or after exposure to said agent or condition in order to prevent or ameliorate the effects of said exposure.

The present invention provides pharmaceutical compositions comprising at least one SK channel blocker, antagonist, inhibitor or modifier which may be admixed with other active ingredients or pharmaceutically acceptable carriers. Such channels include SK1, SK2, SK3 and/or SK4. The ingredients, formulations and forms of such compositions are selected so as to permit delivery of a SK channel blocker, antagonist, inhibitor or modifier to a target tissue, such as to neurons or cells in the nervous system, including the central nervous system, peripheral nervous system, sensory, motor, sympathetic, parasympathetic, autonomic, somatic and other divisions thereof, including the enteric nervous system. Advantageously compositions containing SK channel blocker, antagonist, inhibitor or modifier such as tamapin are formulated to permit their uptake into the blood stream and/or passage into the nervous system.

Such pharmaceutical compositions can be configured for administration to a subject by a wide variety of delivery routes including but not limited to an intravascular delivery route such as by injection or infusion, subcutaneous, intramuscular, intraperitoneal, epidural, or intrathecal delivery routes, or configured for oral, enteral, pulmonary (e.g., via inhalation), intranasal, transmucosal (e.g., by sublingual administration), transdermal or other delivery routes and/or forms of administration known in the art.

The pharmaceutical compositions may be prepared in liquid form, or may be in dried powder form, such as lyophilized form. For oral or enteral use, the pharmaceutical compositions can be configured, for example, as tablets, troches, lozenges, aqueous or oily suspensions, dispersible powders or granules, emulsions, hard or soft capsules, syrups, elixirs or enteral formulas.

The compositions of the invention containing at least one SK channel blocker, antagonist, inhibitor or modifier can be prepared in liquid form, or can be in dried powder, such as lyophilized form, implantable sustained release formulations are also useful, as are transdermal or transmucosal formulations. Additionally or alternatively, the invention provides compositions for use in any of the various slow or sustained release formulations or microparticle formulations known to the skilled artisan, for example, sustained release microparticle formulations, which can be administered via pulmonary, intranasal, or subcutaneous delivery routes.

Liquid pharmaceutical compositions of the invention that are sterile solutions or suspensions can be administered to a patient by injection, for example, intramuscularly, intrathecally, epidurally, intravascularly, intravenously, intrarterially, intraperitoneally or subcutaneously. Sterile solutions can also be administered by intravenous infusion. A SK channel blocker, antagonist, inhibitor or modifier can be included in a sterile solid pharmaceutical composition, such as a lyophilized powder, which can be dissolved or suspended at a convenient time before administration to a patient using sterile water, saline, buffered saline or other appropriate sterile injectable medium.

Implantable sustained release formulations containing at least one SK channel blocker, antagonist, inhibitor or modifier are also useful embodiments of the pharmaceutical compositions of the invention. For example, the pharmaceutically acceptable carrier, being a biodegradable matrix implanted within the body or under the skin of a human or non-human vertebrate, can be a hydrogel. Alternatively, it may be formed from a poly-alpha-amino acid component. Other techniques for making implants for delivery of drugs are also known and useful in accordance with the invention.

Nasal delivery forms. In accordance with the invention, intranasal delivery of a composition containing at least one SK channel blocker, antagonist, inhibitor or modifier is also useful. This mode allows passage of the at least one SK channel blocker, antagonist, inhibitor or modifier to the blood stream directly after administration to the inside of the nose, without the necessity for deposition of the product in the lung. Formulations suitable for intransal administration include those with dextran or cyclodextran, and intranasal delivery devices are known.

Oral dosage forms. An oral dosage form containing at least one SK channel blocker, antagonist, inhibitor or modifier, may be used. If necessary, the composition can be chemically modified so that oral delivery is efficacious. Generally, the chemical modification contemplated is the attachment of at least one moiety to the molecule itself, where said moiety permits inhibition of proteolysis; and uptake into the blood stream from the stomach or intestine. Also desired is the increase in overall stability of the compound and increase in circulation time in the body. Moieties useful as covalently attached half-life extending moieties in this invention can also be used for this purpose. Examples of such moieties include: PEG, copolymers of ethylene glycol and propylene glycol, carboxymethyl cellulose, dextran, polyvinyl alcohol, polyvinyl pyrrolidone and polyproline. Other polymers that could be used are poly-1, 3-dioxolane and poly-1,3,6-tioxocane. Preferred for pharmaceutical usage, as indicated above, are PEG moieties.

In powder forms, the pharmaceutically acceptable carrier is a finely divided solid, which is in admixture with finely divided active ingredient(s), including the inventive composition. For example, in some embodiments, a powder form is useful when the pharmaceutical composition is configured as an inhalant.

Pulmonary delivery forms. Pulmonary delivery of the inventive compositions is also useful. The at least one SK channel blocker, antagonist, inhibitor or modifier is delivered to the lungs of a mammal while inhaling and traverses across the lung epithelial lining to the blood stream. A wide range of mechanical devices designed for pulmonary delivery of therapeutic products, including but not limited to nebulizers, metered dose inhalers, and powder inhalers, all of which are familiar to those skilled in the art may be employed. All such devices require the use of formulations suitable for the dispensing of the inventive compound. Typically, each formulation is specific to the type of device employed and can involve the use of an appropriate propellant material, in addition to diluents, adjuvants and/or carriers useful in therapy. A SK channel blocker, antagonist, inhibitor or modifier may be prepared in particulate form with an average particle size of less than 10 microns most preferably 0.5 to 5 microns for effective delivery to the distal lung. The use of liposomes, microcapsules or microspheres, inclusion complexes, or other types of carriers is contemplated. Formulations suitable for use with a nebulizer, either jet or ultrasonic, will typically comprise the inventive compound dissolved in water at a concentration of about 0.1 to 25 mg of biologically active protein per mL of solution. The formulation can also include a buffer and/or simple sugar for protein stabilization and regulation of osmotic pressure. The nebulizer formulation may also contain a surfactant to reduce or prevent surface induced aggregation of the protein caused by atomization of the solution in forming the aerosol.

Formulations for use with a metered-dose inhaler device will generally comprise a finely divided powder containing at least one SK channel blocker, antagonist, inhibitor or modifier suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be used as a surfactant. Formulations for dispensing from a powder inhaler device will comprise a finely divided dry powder containing the at least one SK channel blocker, antagonist, inhibitor or modifier and can also include a bulking agent, such as lactose, sorbitol, sucrose, mannitol, trehalose, or xylitol in amounts which facilitate dispersal of the powder from the device, e.g., 50 to 90% by weight of the formulation.

Transdermal, transmucosal and buccal delivery. In some embodiments, a pharmaceutical composition comprising at least one SK channel blocker, antagonist, inhibitor or modifier is configured as a part of a pharmaceutically acceptable transdermal or transmucosal patch or a troche. Transdermal patch drug delivery systems, for example, matrix type transdermal patches, are known and useful for practicing some embodiments of the present pharmaceutical compositions. A variety of pharmaceutically acceptable systems for transmucosal delivery of therapeutic agents is also known in the art and is compatible with the practice of the present invention. Optionally, a transmucosal delivery system can be in the form of a bilayer tablet, in which the inner layer also contains additional binding agents, flavoring agents, or fillers. Some useful systems employ a non-ionic detergent along with a permeation enhancer. Transmucosal delivery devices may be in free form, such as a cream, gel, or ointment, or may comprise a determinate form such as a tablet, patch or troche. For example, delivery of the inventive composition can be via a transmucosal delivery system comprising a laminated composite of, for example, an adhesive layer, a backing layer, a permeable membrane defining a reservoir containing the inventive composition, a peel seal disc underlying the membrane, one or more heat seals, and a removable release liner. These examples are merely illustrative of available transmucosal drug delivery technology and are not limiting of the present invention.

Buccal delivery formulations are known in the art for use with peptides, such as the tamapin peptide. For example, known tablet or patch systems configured for drug delivery through the oral mucosa such as via sublingual mucosa, include some embodiments that comprise an inner layer containing the drug, a permeation enhancer, such as a bile salt or fusidate, and a hydrophilic polymer, such as hydroxypropyl cellulose, hydroxypropyl methylcellulose, hydroxyethyl cellulose, dextran, pectin, polyvinyl pyrrolidone, starch, gelatin, or other polymers known to be useful for this purpose. This inner layer can have one surface adapted to contact and adhere to the moist mucosal tissue of the oral cavity and can have an opposing surface adhering to an overlying non-adhesive inert layer.

The dosage regimen involved in a method for treating the diseases, disorders or conditions described herein will be determined by the attending physician, considering various factors which modify the action of drugs such as the age, condition, body weight, sex and diet of the patient, the severity of disability, disease, or condition, time of administration and other clinical factors. Dosages will depend on the nature of the at least one SK channel blocker, antagonist, inhibitor, or modifier. Representative dosages include dosages in the range of 0.001-1,000 micrograms, 0.01-100, or 0.1-50 micrograms per kilogram of body weight may be selected. Non-limiting dosage ranges for several SK channel protein blockers, antagonists, inhibitors or modifiers are: Lei-dab? (min: 3 nM and max: 1.0 μM), Apamin (min 0.1 g/kg and max 2.0 g/kg) or (min 50 nM and max 1.0 μM), Scyllatoxin (min 100 pM and max 1.0 nM), and Tamapin (min 24 pM and max 1.0 nM). Administered dosages may be selected to provide the above molar concentrations of these agents at the sites of action.

Medical devices suitable for single, metered, depot, or continuous administration of compositions according to the invention are also contemplated. A device may be designed or adapted to control, meter, measure a precise volume or amount of at least one SK channel blocker, antagonist, inhibitor or modifier. It may also be designed or adapted to administer the SK inhibitor to a subject in utero, to a subject at risk of exposure to alcohol, chemical agents or deleterious conditions, or to an injured or a subject undergoing a surgical procedure. Such devices or compositions may be included in a kit that includes packaging materials or instructions for use.

EXAMPLES

The following Examples describe certain, nonlimiting features of the invention.

Example 1: Impaired Motor Skill Learning in Mice Exposed to EtOH in Utero

Pregnant mice CD-1 mice purchased from Charles River Company and bred under a light-dark cycle at a constant temperature were injected i.p. with 2 g/kg with either PBS (control) or ethanol (EtOH) thus exposing fetal mice in utero to PBS or EtOH. Thirty days after mice were born (day P30) motor skills of the control and EtOH-treated groups were compared using Rotarod test. The treatment timeline for the mice is shown in FIG. 1A and the Rotarod test is depicted by FIG. 1B.

For assessment of motor learning behavior, mice (P30) were carried out using an accelerating Rotarod [5] apparatus (TSE Instruments) over 3 repeated trials (5 minutes per trial)/day for 2 consecutive days before testing phase. The Rotarod testing involves placing the mice on a rotating bar and determining the length of time that they can retain their balance as the rate of rotation is increased (max 80 rpm, for 5 min). On the day of testing, mice were kept in their home cages and acclimated to the testing room for at least 15 min. 2 min acclimation session at 2 rpm one time prior to the test phase was performed. Testing phase consisted of 3 trials per day separated by 30 min each for 2 consecutive days (total 6 trials). Each trail was terminated when mouse fell off or reached maximum 5 min (maximum speed). During the trials, mice that moved 180° (same direction of rotation) were gently turned around, face forward, to opposite direction of rotation. The latency to fall from a rotating rod was scored automatically with infrared sensors in a Rotamex 5 rotarod (Columbus Inst.; Columbus, Ohio).

The learning index of control and EtOH treated male and female based on the Rotarod test are shown in FIG. 1C.

Learning rates of male (M) and female (F) mice exposed in utero to EtOH were decreased compared to control mice administered PBS in utero.

While initial coordination of PBS- and EtOH-treated mice was not affected by EtOH exposure as shown by FIG. 1D and in trial 1 in FIG. 1E, the mice exposed to EtOH in utero had significant shorter latency to fall time during subsequent trials 2, 3, 4, 5 and 6 as shown in FIG. 1E.

Rotarod terminal speed was determined on trial 1 and again on trial 6. The mean Rotarod terminal speed for control mice was significantly higher than that for EtOH-treated mice as shown by the black lines in FIG. 1F. These results did not correlate with body weight differences between PBS- and EtOH-treated mice which were comparable as shown by FIG. 1G.

These results show that exposure of fetal mice to EtOH in utero negatively affects learning and motor skills compared to control mice not given EtOH.

Example 2: Heat Shock Reporter System for Long-Term Labelling of Cells Stressed in Utero In utero electroporation (IUE) with a reporter construct and in utero exposure of fetal CD-1 mice to PBS (control) or ethanol (EtOH) was carried out as described by the timeline in FIG. 2A. FIG. 2B shows the design of the reporter construct. The reporter construct expresses green fluorescent protein (GFP) (FIG. 2B left side) when transformed cells are not exposed to stress (EtOH). When exposed to stress reporter construct expresses both GPF and red fluorescent protein (RFP) (FIG. 2B, right side). Red protein is depicted by the circles in the middle section of the right side of FIG. 2B and GFP by the circles in the bottom section of this figure.

In utero electroporation was carried out as described [1-3]. Briefly, the plasmid for Flippase-FRT based reporter of heat shock factor 1 (Hsf1) activation was co-electroporated with EGFP-f plasmid (Addgene, 2 µg/µl each). FIG. 2C, left panel shows only expression of GFP in PBS-treated control mice; FIG. 2C, right panel shows GFP and RFP reporter expression in GFP$^+$ electroporated cells in the M1 cortex of the mix prenatally exposed to EtOH (arrows indicate locations of reporter expressions in original color micrograph). FIG. 2D shows the relative percentage of RFP$^+$ cells in cells derived from PBS-treated control mice and those from EtOH-treated mice. These data show permanent labelling of cells experiencing high level heat shock protein activation during prenatal stage.

By using this method, the cells that had robust prenatal Hsf1 activation were labeled by RFP reporter. This visualizes the neurons into the primary motor cortex at embryonic day 15.5 (E15.5) at which layer II/III neurons are generated by intraperitoneal (i.p.) injection of PBS/ethanol (2.0 mg/kg body weight) at E16.5 and E17.5.

The RFP reporter expression was induced upon Hsf1 activation in a subset of GFP-positive neurons. This alcohol regimen did not induce any obvious effects in brain structure. Around 35% of the electroporated neurons expressed in the reporter positive cells. However, the reporter expression rate and pattern varied among embryos due to the stochastic activation of Hsf1. Pups were screened using an epifluorescence stereomicroscope at postnatal days (P1) that had GFP-positive cells in their primary motor cortex. Further experiments were performed on these mice i.e., single cell sampling, electrophysiology study, immunohistochemistry (IHC) and neurons morphology at P30. FIG. 2D shows the percentage of RFP+ cells in GFP+ cells.

Single cell sampling. As described previously [4], the cell contents of live single neuron from brain tissue were obtained with the following modification. Under the visual guidance, frontal motor cortex layer II/III neurons that expressed the GFP$^|$/RFP$^|$ cells and GFP$^|$/RFP$^-$ cells in the motor cortex were targeted by a patch electrode. The patch electrode (3-3.5 MΩ) was used to collect the cell content that was mounted on a micromanipulator (Sutter MP 285) and place over the target neuron under visual guidance. Prior to entering into the artificial cerebral spinal fluid (aCSF) positive pressure in the electrode was applied so that the internal air was flowing out during the whole process. After the electrode had approached to the neuron under visual guidance, small negative pressure was applied by 1 ml syringe suction to rupture the cell membrane. To collect the neuronal contents, strong negative pressure was applied with a 1 ml syringe until the soma was completely extracted into the electrode. The complete aspiration of soma content into the patch electrode was visualized under DIC optics by focusing on various Z plane levels. The electrode was rapidly retracted from the bath and the contents expelled into a thin-walled RNA free PCR tube (corning) containing 2 µl lysis buffer (10 U/µl RNase OUT, 10% IGEPAL and 40 U/µl nuclease free water). The collected single cell contents were then immediately frozen on dry ice and stored at −80° C. until further processing for single cell RNA sequencing.

Example 3: The Increase in KCNN2-Expressing Pyramidal Neurons in M1 Cortex Correlates with the Severity of Motor Learning Deficits in Mice Prenatally Exposed to EtOH In single cell RNA sequencing of reporter+ and reporter− neurons, the inventors found the specific expression of KCNN2 in reporter+ neurons. As shown by FIG. 3A, the SK2 (KCNN2) protein was expressed at a significantly higher level in layers II/III in M1 cortex in P30 mice who had been treated in utero with EtOH, compare FIG. 3A, left (PBS) and right (EtOH) panels where white arrows indicate the KCNN2$^+$ cells. FIG. 3B shows a statistically significant difference in KCNN2 between PBS and EtOH samples. Quantification of KCNN2$^+$ cells in layers II/III in M1 cortex in PBS- and EtOH-exposed mice. More KCNN2$^+$ cells were observed in EtOH-exposed mice. * $P=0.006$ by Student's t-test (n=16: PBS and 16: EtOH).

FIG. 3C shows that KCNN2 expression was enriched in RFP$^+$ pyramidal neurons in layers II/III in M1 cortex in EtOH-exposed mice (insets show the higher magnification view of the squared areas). FIG. 3D shows the percentages of KCNN2$^+$ neurons in GFP$^+$/RFP$^-$ cells in PBS (black)- or EtOH (white)-exposed mice and GFP$^+$/RFP$^+$ cells in EtOH-exposed (gray) mice. $F(2, 34)=38.40$, **$P<0.01$, *$P<0.05$ by posthoc Tukey's test. FIG. 3E provides a Pearson's correlation analysis revealing the negative correlation between the learning index and the number of KCNN2$^|$ cells in layers in M1 cortex. ($R=0.453$, $P=0.033$). These data demonstrate that higher levels of KCNN2+ cells in brains of mice treated in utero with EtOH correlated with learning disability.

Electrophysiology: Coronal slices containing primary motor cortex (300 µm) were prepared as described above by using a vibrating blade microtome (Leica VT 1000S) from DNA (HSE-FLP0, CAG GFP and RFP FRT, 2 µg/µl each) electroporated mice (P30) brain. The recording chamber was perfused with oxygenated (95% $O_2$/5% $CO_2$) aCSF at 2 ml/min at room temperature. DNA electroporated primary motor cortex neurons were visualized through an infrared charge-coupled device (CCD) camera (C2741-79; Hamamatsu Photonics, Hamamatsu, Japan). The electrodes were filled with internal solution containing (in mM) 130 K-glucose, 10 KCl, 10 HEPES, 10 EGTA, 2 MgCl$_2$, 2 Na$_2$-ATP and 0.3 Na-GTP (pH 7.3; electrode resistances: 4-6 MΩ). Cells were recorded in the whole-cell voltage or current clamp mode with a holding potential of −60 mV using a patch-clamp amplifier (700B; Molecular Devices, Sunnyvale, Calif. USA). Series resistance was compensated. The output of the amplifier was digitized using an A/D converter board (Digidata 1322; Molecular Devices) with a sampling rate of 10 kHz, and recorded on a hard disk by data acquisition software (pCLAMP10; Molecular Devices). For the mAHP, cells were held at −60 mV under current clamp mode and action potentials were evoked through injecting positive current. LTP was induced electrically under voltage clamp mode by applying single 1-sec train (100 Hz, 100 μA, Isoflexm, A.M.P.I; CPI, Carl Pisaturo Standord University). 100 nM Tamapin (Sigma-Aldrich) was dissolved in normal aCSF and perfused whenever required as shown in figure legends.

Immunohistochemistry: The brains were removed and post fixed in the same fixative (4% PFA) at 4° C. for overnight, followed by 10% and 30% sucrose in PBS for 24 h each. Thereafter, coronaUsagittal sections were prepared (60 μm) on cryostat (Leica). Free floating mouse brain sections were subjected to target retrieval solution (Dako, California) for 30 min around 100° C. and thereafter incubated for 60 min in methanol (MeOH) and hydrogen peroxide (H2O2) (4:1) solution to diminish the endogenous peroxidase. After subsequently rinsing with PBS-T (3×), nonspecific binding sites were blocked with 2% bovine serum albumin (BSA) for 30 min at room temperature (RT) and the primary antibodies {anti-goat KCNN2 (1:500, Abcam), anti-chicken CFP (1:700, Abcam) and anti-rabbit RFP (1:500, Abcam)} were applied overnight at 4° C. Three-time rinses with PBS-T before incubation with the secondary antibody (anti-goat HRP (1:500, Jackson Immunolab), anti-chicken cy2 (1:200, Jackson Immunolab) and biotinylated anti-rabbit (1:200, Jackson Immunolab)} for 3 h at RT. KCNN2 immunoreactivity was visualized by reaction with cy3: ISA (1:500) for 1 h at RT after rinsing (PBS-T, 3×). Thereafter, these section were treated with PBS: H$_2$O$_2$ (30:1) after rinsing (PBS-T, 3×) for 1 h at RT before A:B:C (1:1:100) incubation for 1 h at RT. The RFP staining was visualized with cy5: TSA (1:500) for 1 h at RT after rinsing (PBS-T, 3×). DAPI (1:10,000) solution was used to reveal the nuclei. The sections were analyzed using Olympus confocal microscope (Japan) equipped with Olympus digital camera. Brightness of images was adjusted using image J and Photoshop.

Example 4 KCNN2 Antagonist, Tamapin (100 nM), Affects the Medium Duration Afterhyperpolarization (mAHP) in Reporter-Positive Pyramidal Neurons in M1

FIGS. 4A, 4B and 4C show that KCNN2 antagonist (Tamapin, 100 nM)-sensitive afterhyperpolarization (mAHP) examined in PBS- or EtOH-exposed GFP$^+$/RFP$^+$ or GFP$^+$/RFP$^-$ neurons as indicated. The blockage of EtOH-induced KCNN2 overexpression by Tamapin in RFP$^+$ neurons reduced the mAHP (FIG. 4C, panel c1) (*P=0.009 by Student's t-test) and increased the firing frequency (FIG. 4C, panels c2 and c3). Tamapin showed no significant effects on RFP$^-$ neurons in PBS- or EtOH-exposed brains (a1-b3). (FIGS. 4A-4C, panels a4-c4) Left panels: Cumulative distributions of the amplitude of action potential and the mean amplitude of action potentials (insets)recorded from control (black)- and Tamapin (red)-stimulated neurons. Right panels: Firing frequencies, showing significant increase in RFP$^+$ neurons. *P=0.016 by Student's t-test.

These data suggest that administration of a KCNN2 antagonist can compensate or reverse effects caused by prenatal EtOH exposure.

Example 5: KCNN2 Antagonist Improves Motor Skill Learning in Mice Exposed to Etoh Prenatally Pregnant mice CD-1 mice were injected i.p. with 2 g/kg with either PBS (control) or ethanol (EtOH) thus exposing fetal mice in utero to PBS or EtOH. Mice were tested using the Rotarod test described above on postnatal days 30, 31, 32 and 33 days as shown by the timeline in FIG. 5A. After P30-31 and P32 trials, mice were injected i.p. with PBS or tamapin as also shown in FIG. 5A. Thus, the mice were tested for the motor learning before and after the Tamapin injection (i.p.).

As shown by FIG. 5B treatment of mice that had been exposed in utero to EtOH with tamapin (dark squares) significantly improved latency to fall scores compared to mice exposed in utero to EtOH who did not receive the post-natal tamapin treatment (bottom trace, triangles). FIG. 5D describes increased learning rate for mice exposed in utero to EtOH who received tamapin treatment compared to otherwise identical EtOH-treated mice not receiving tamapin. FIG. 5C is a control showing that initial coordination prior to tamapin treatment were approximately equivalent. Tamapin improved the motor learning in the EtOH-exposed mice (trial 7-12). P=0.0001 by repeated-measure ANOVA, P=0.0001 by Kolmogorov-Smirnov test. The latency to fall at the first trial followed by injection (trial 7) is similar between vehicle and Tamapin in both PBS-exposed and EtOH-exposed groups (P=0.302 and 0.960 by Student's t-test, respectively). FIG. 5C: The initial motor coordination was not affected by Tamapin in EtOH-exposed mice. FIG. 5D: Motor leaning (trial 7-12) was rescued in Tamapin-injected EtOH-exposed mice. *P=0.015 by Student's t-test.

FIGS. 5E, 5F and 5G, which are based on Rotarod terminal speed tests, show similar improvement in mice exposed in utero to EtOH and receiving tamapin compared to EtOH treated mice receiving only PBS. FIG. 5E: The performance of individual mice (gray lines) on rotarod at the beginning (trail 7) and the end of Tamapin injection (trial 12). The solid lines indicate the means. *P=0.015 by Student's t-test (n=12: PBS and 7: EtOH). FIG. 5F: The initial motor coordination was not affected by tamapin in PBS-exposed mice. FIG. 5G: No effects of tamapin on motor learning were observed in PBS-exposed mice (trial 7-12), P=0.596 by Student's t-test.

These data show that treatment with the KCNN2 antagonist, tamapin, significantly reversed effects of fetal exposure to EtOH.

In the Examples above, all statistical data were presented as the mean with standard error. All data comparisons (test and control) were collected at the same time period, and statistical analysis was performed using two-way analysis of variance (ANOVA) or one-way ANOVA followed by Tukey multiple range tests across multiple means. Repetitive measure ANOVA was used to compare the multiple time points among test and control. Pearson Correlation Coefficients (PCC) within the set was also calculated using Microsoft Excel sheet. The two-tail student's test was used for pairwise comparison. A 95% confidence level was used; considered to indicate statistical significance.

The foregoing discussion discloses embodiments in accordance with the present disclosure. As will be understood by those skilled in the art, the approaches, methods, techniques, materials, devices, and so forth disclosed herein may be embodied in additional embodiments as understood by those of skill in the art, it is the intention of this application to encompass and include such variation. Accordingly, this disclosure is illustrative and should not be taken as limiting the scope of the following claims.

REFERENCES

1. Hashimoto-Torii, K., et al., *Interaction between Reelin and Notch signaling regulates neuronal migration in the cerebral cortex*. Neuron, 2008. 60(2): p. 273-84.
2. Sarkisian, M. R., et al., *MEKK4 signaling regulates filamin expression and neuronal migration*. Neuron, 2006. 52(5): p. 789-801.
3. Torii, M. and P. Levitt, *Dissociation of corticothalamic and thalamocortical axon targeting by an EphA7-mediated mechanism*. Neuron, 2005. 48(4): p. 563-75.
4. Qiu, S., et al., *Single-neuron RNA-Seq: technical feasibility and reproducibility*. Front Genet, 2012. 3: p. 124.
5. Rothwell, P. E., et al., *Autism-associated neuroligin-3 mutations commonly impair striatal circuits to boost repetitive behaviors*. Cell, 2014. 158(1): p. 198-212.

TABLE 1

| Item | Designation | Sequence |
|---|---|---|
| 1 | Tamapin | AFCNLRRCELSCRSLGLLGKCIGEECKCVPY |
| 2 | Tamapin A1C | CFCNLRRCELSCRSLGLIGKCIGEECKCVPY |
| 3 | Tamapin A1D | DFCNLRRCELSCRSLGLLGKCIGEECKCVPY |
| 4 | Tamapin A1E | EFCNLRRCELSCRSLGLLGKCIGEECKCVPY |
| 5 | Tamapin A1F | FFCNIARCELSCRSLGLLGKCIGEECKCVPY |
| 6 | Tamapin A1G | GFCNIARCELSCRSLGLLGKCIGEECKCVPY |
| 7 | Tamapin A1H | HFCNLRRCELSCRSLGLLGKCIGEECKCVPY |
| 8 | Tamapin A1I | IFCNLRRCELSCRSLGLLGKCIGEECKCVPY |
| 9 | Tamapin A1K | KFCNLRRCELSCRSLGLLGKCIGEECKCVPY |
| 10 | Tamapin A1L | LFCNLRRCELSCRSLGLLGKCIGEECKCVPY |
| 11 | Tamapin A1M | MFCNLRRCELSCRSLGLLGKCIGEECKCVPY |
| 12 | Tamapin A1N | NFCNLRRCELSCRSLGLLGKCIGEECKCVPY |
| 13 | Tamapin A1P | PFCNLRRCELSCRSLGLLGKCIGEECKCVPY |
| 14 | Tamapin A1Q | QFCNLRRCELSCRSLGLLGKCIGEECKCVPY |
| 15 | Tamapin A1R | RFCNLRRCELSCRSLGLLGKCIGEECKCVPY |
| 16 | Tamapin A1S | SFCNLRRCELSCRSLGLLGKCIGEECKCVPY |
| 17 | Tamapin A1T | TFCNLRRCELSCRSLGULGKCIGEECKCVPY |
| 18 | Tamapin A1V | VFCNLRRCELSCRSLGLLGKCIGEECKCVPY |
| 19 | Tamapin A1W | WFCNLRRCELSCRSLGLLGKCIGEECKCVPY |
| 20 | Tamapin A1Y | YFCNLRRCELSCRSLGLLGKCIGEECKCVPY |
| 21 | Tamapin F2A | AACNLRRCELSCRSLGLLGKCIGEECKCVPY |

TABLE 1-continued

| Item | Designation | Sequence |
|---|---|---|
| 22 | Tamapin F2C | ACCNLRRCELSCRSLGLLGKCIGEECKCVPY |
| 23 | Tamapin F2D | ADCNLRRCELSCRSLGLLGKCIGEECKCVPY |
| 24 | Tamapin F2E | AECNLRRCELSCRSLGLLGKCIGEECKCVPY |
| 25 | Tamapin F2G | AGCNLRRCELSCRSLGLLGKCIGEECKCVPY |
| 26 | Tamapin F2H | AHCNLRRCELSCRSLGLLGKCIGEECKCVPY |
| 27 | Tamapin F2I | AICNLRRCELSCRSLGLLGKCIGEECKCVPY |
| 28 | Tamapin F2K | AKCNIARCELSCRSLGLLGKCIGEECKCVPY |
| 29 | Tamapin F2L | ALCNLRRCELSCRSLGLLGKCIGEECKCVPY |
| 30 | Tamapin F2M | AMCNLRRCELSCRSLGLLGKCIGEECKCVPY |
| 31 | Tamapin F2N | ANCNLRRCELSCRSLGLLGKCIGEECKCVPY |
| 32 | Tamapin F2P | APCNLRRCELSCRSLGLLGKCIGEECKCVPY |
| 33 | Tamapin F2Q | AQCNLRRCELSCRSLGLLGKCIGEECKCVPY |
| 34 | Tamapin F2R | ARCNLRRCELSCRSLGLLGKCIGEECKCVPY |
| 35 | Tamapin F2S | ASCNLRRCELSCRSLGLLGKCIGEECKCVPY |
| 36 | Tamapin F2T | ATCNLRRCELSCRSLGLLGKCIGEECKCVPY |
| 37 | Tamapin F2V | AVCNLRRCELSCRSLGILGKCIGEECKCVPY |
| 38 | Tamapin F2W | AWCNLRRCELSCRSLGLLGKCIGEECKCVPY |
| 39 | Tamapin F2Y | AYCNLARCELSCRSLGLLGKCIGEECKCVPY |
| 40 | Tamapin C3A | AFANLRRCELSCRSLGLLGKCIGEECKCVPY |
| 41 | Tamapin C3D | AFDNLRRCELSCRSLGLLGKCIGEECKCVPY |
| 42 | Tamapin C3E | AFENLRRCELSCRSLGLLGKCIGEECKCVPY |
| 43 | Tamapin C3F | AFFNLARCELSCRSLGLLGKCIGEECKCVPY |
| 44 | Tamapin C3G | AFGNLRRCELSCRSLGLLGKCIGEECKCVPY |
| 45 | Tamapin C3H | AFHNLARCELSCRSLGLLGKCIGEECKCVPY |
| 46 | Tamapin C3I | AFINLRRCELSCRSLGLLGKCIGEECKCVPY |
| 47 | Tamapin C3K | AFKNIARCELSCRSLGLLGKCIGEECKCVPY |
| 48 | Tamapin C3L | AFLNLRRCELSCRSLGLLGKCIGEECKCVPY |
| 49 | Tamapin C3M | AFMNLRRCELSCRSLGLLGKCIGEECKCVPY |
| 50 | Tamapin C3N | AFNNLRRCELSCRSLGLLGKCIGEECKCVPY |
| Si | Tamapin C3P | AFPNLRRCELSCRSLGLLGKCIGEECKCVPY |
| 52 | Tamapin C3Q | AFQNLRRCELSCRSLGLLGKCIGEECKCVPY |
| 53 | Tamapin C3R | AFRNLRRCELSCRSLGLLGKCIGEECKCVPY |
| 54 | Tamapin C3S | AFSNLRRCELSCRSLGLLGKCIGEECKCVPY |
| 55 | Tamapin C3T | AFTNLRRCELSCRSLGLLGKCIGEECKCVPY |
| 56 | Tamapin C3V | AFVNLRRCELSCRSLGLLGKCIGEECKCVPY |
| 57 | Tamapin C3W | AFWNLRRCELSCRSLGLLGKCIGEECKCVPY |
| 58 | Tamapin C3Y | AFYNLRRCELSCRSLGLLGKCIGEECKCVPY |
| 59 | Tamapin N4A | AFCALRRCEISCRSLGLLGKCIGEECKCYPY |
| 60 | Tamapin N4C | AFCCLRRCELSCRSLGLLGKCIGEECKCVPY |

TABLE 1-continued

| Item | Designation | Sequence |
|---|---|---|
| 61 | Tamapin N4D | AFCDLRRCEISCRSLGLLGKCIGEECKCYPY |
| 62 | Tamapin N4E | AFCELRRCELSCRSLGLLGKCIGEECKCVPY |
| 63 | Tamapin N4F | AFCFLRRCELSCRSLGLLGKCIGEECKCVPY |
| 64 | Tamapin N4G | AFCGLRRCELSCRSLGLLGKCIGEECKCVPY |
| 65 | Tamapin N4H | AFCHLRRCELSCRSLGLLGKCIGEECKCVPY |
| 66 | Tamapin N4I | AFCILRRCELSCRSLGLLGKCIGEECKCVPY |
| 67 | Tamapin N4K | AFCKLRRCELSCRSLGLLGKCIGEECKCNPY |
| 68 | Tamapin N4L | AFCLLARCELSCRSLGLLGKCIGEECKCVPY |
| 69 | Tamapin N4M | AFCMLRRCELSCRSLGLLGKCIGEECKCNPY |
| 70 | Tamapin N4P | AFCPLRRCELSCRSLGLLGKCIGEECKCVPY |
| 71 | Tamapin N4Q | AFCQLRRCELSCRSLGLLGKCIGEECKCVPY |
| 72 | Tamapin N4R | AFCRLRRCELSCRSLGLLGKCIGEECKCVPY |
| 73 | Tamapin N4S | AFCSLRRCELSCRSLGLLGKCIGEECKCVPY |
| 74 | Tamapin N4T | AFCTLRRCELSCRSLGLLGKCIGEECKCVPY |
| 75 | Tamapin N4V | AFCVLRRCELSCRSLGLLGKCIGEECKCVPY |
| 76 | Tamapin N4W | AFCWLRRCELSCRSLGLLGKCIGEECKCVPY |
| 77 | Tamapin N4Y | AFCYLRRCELSCRSLGLLGKCIGEECKCVPY |
| 78 | Tamapin L5A | AFCNARRCELSCRSLGLLGKCIGEECKCVPY |
| 79 | Tamapin L5C | AFCNCRRCELSCRSLGLLGKCIGEECKCVPY |
| 80 | Tamapin L5D | AFCNDRRCELSCRSLGLLGKCIGEECKCVPY |
| 81 | Tamapin L5E | AFCNERRCELSCRSLGLLGKCIGEECKCVPY |
| 82 | Tamapin L5F | AFCNFRRCELSCRSLGLLGKCIGEECKCVPY |
| 83 | Tamapin L5G | AFCNGRRCELSCRSLGLLGKCIGEECKCVPY |
| 84 | Tamapin L5H | AFCNHRRCELSCRSLGLLGKCIGEECKCVPY |
| 85 | Tamapin L5I | AFCNIRRCELSCRSLGLLGKCIGEECKCVPY |
| 86 | Tamapin L5K | AFCNKRRCELSCRSLGLLGKCIGEECKCVPY |
| 87 | Tamapin L5M | AFCNMRRCELSCRSLGLLGKCIGEECKCVPY |
| 88 | Tamapin L5N | AFCNNRRCELSCRSLGLLGKCIGEECKCVPY |
| 89 | Tamapin L5P | AFCNPRRCELSCRSLGLLGKCIGEECKCVPY |
| 90 | Tamapin L5Q | AFCNQRRCELSCRSLGLLGKCIGEECKCVPY |
| 91 | Tamapin L5R | AFCNRRRCELSCRSLGLLGKCIGEECKCVPY |
| 92 | Tamapin L5S | AFCNSRRCELSCRSLGLLGKCIGEECKCVPY |
| 93 | Tamapin L5T | AFCNTRRCELSCRSLGLLGKCIGEECKCVPY |
| 94 | Tamapin L5V | AFCNVRRCELSCRSLGLLGKCIGEECKCVPY |
| 95 | Tamapin L5W | AFCNWRRCELSCRSLGLLGKCIGEECKCVPY |
| 96 | Tamapin L5Y | AFCNYRRCELSCRSLGLLGKCIGEECKCVPY |
| 97 | Tamapin R6A | AFCNLARCELSCRSLGLLGKCIGEECKCVPY |
| 98 | Tamapin R6C | AFCNLCRCELSCRSLGLLGKCIGEECKCVPY |
| 99 | Tamapin R6D | AFCNLDRCELSCRSLGLLGKCIGEECKCVPY |
| 100 | Tamapin R6E | AFCNLERCELSCRSLGLLGKCIGEECKCVPY |
| 101 | Tamapin R6F | AFCNLFRCELSCRSLGLLGKCIGEECKCVPY |
| 102 | Tamapin R6G | AFCNLGRCELSCRSLGLLGKCIGEECKCVPY |
| 103 | Tamapin R6H | AFCNLHRCELSCRSLGLLGKCIGEECKCVPY |
| 104 | Tamapin R6I | AFCNLIRCELSCRSLGLLGKCIGEECKCVPY |
| 105 | Tamapin R6K | AFCNLKRCELSCRSLGLLGKCIGEECKCVPY |
| 106 | Tamapin RCL | AFCNLLRCELSCRSLGLLGKCIGEECKCVPY |
| 107 | Tamapin RCM | AFCNLMRCELSCRSLGLLGKCIGEECKCVPY |
| 108 | Tamapin RCN | AFCNLNRCELSCRSLGLLGKCIGEECKCVPY |
| 109 | Tamapin R6P | AFCNLPRCELSCRSLGLLGKCIGEECKCVPY |
| 110 | Tamapin R6Q | AFCNLQRCELSCRSLGLLGKCIGEECKCVPY |
| 111 | Tamapin R6S | AFCNLSRCELSCRSLGLLGKCIGEECKCVPY |
| 112 | Tamapin R6T | AFCNLTRCELSCRSLGLLGKCIGEECKCVPY |
| 113 | Tamapin R6V | AFCNLNRCELSCRSLGLLGKCIGEECKCVPY |
| 114 | Tamapin R6W | AFCNLWRCELSCRSLGLLGKCIGEECKCVPY |
| 115 | Tamapin R6Y | AFCNLYRCELSCRSLGLLGKCIGEECKCVPY |
| 116 | Tamapin R7A | AFCNLRACELSCRSLGLLGKCIGEECKCVPY |
| 117 | Tamapin R7C | AFCNLRCCELSCRSLGLLGKCIGEECKCVPY |
| 118 | Tamapin R7D | AFCNLRDCELSCRSLGLLGKCIGEECKCVPY |
| 119 | Tamapin R7E | AFCNLRECELSCRSLGLLGKCIGEECKCVPY |
| 120 | Tamapin R7F | AFCNLRFCELSCRSLGLLGKCIGEECKCVPY |
| 121 | Tamapin R7G | AFCNLRGCELSCRSLGLLGKCIGEECKCVPY |
| 122 | Tamapin R7H | AFCNLRHCELSCRSLGLLGKCIGEECKCVPY |
| 123 | Tamapin R7I | AFCNLRICELSCRSLGLLGKCIGEECKCVPY |
| 124 | Tamapin R7K | AFCNLRKCELSCRSLGLLGKCIGEECKCVPY |
| 125 | Tamapin R7L | AFCNLRLCELSCRSLGLLGKCIGEECKCVPY |
| 126 | Tamapin R7M | AFCNLRMCELSCRSLGLLGKCIGEECKCVPY |
| 127 | Tamapin R7N | AFCNLRNCELSCRSLGLLGKCIGEECKCVPY |
| 128 | Tamapin R7P | AFCNLRPCELSCRSLGLLGKCIGEECKCVPY |
| 129 | Tamapin R7Q | AFCNLRQCELSCRSLGLLGKCIGEECKCVPY |
| 130 | Tamapin R7S | AFCNLRSCELSCRSLGLLGKCIGEECKCVPY |
| 131 | Tamapin R7T | AFCNLRTCELSCRSLGLLGKCIGEECKCVPY |
| 132 | Tamapin R7V | AFCNLRVCELSCRSLGLLGKCIGEECKCVPY |
| 133 | Tamapin R7W | AFCNLRWCELSCRSLGLLGKCIGEECKCVPY |
| 134 | Tamapin R7Y | AFCNLRYCELSCRSLGLLGKCIGEECKCVPY |
| 135 | Tamapin C8A | AFCNLRRAELSCRSLGLLGKCIGEECKCVPY |
| 136 | Tamapin C8D | AFCNLRRDELSCRSLGLLGKCIGEECKCVPY |
| 137 | Tamapin C8E | AFCNLRREELSCRSLGLLGKCIGEECKCVPY |
| 138 | Tamapin C8F | AFCNLRRFELSCRSLGLLGKCIGEECKCVPY |

TABLE 1-continued

| Item | Designation | Sequence |
|---|---|---|
| 139 | Tamapin C8G | AFCNLRRGELSCRSLGLLGKCIGEECKCVPY |
| 140 | Tamapin C8H | AFCNLRRHELSCRSLGLLGKCIGEECKCVPY |
| 141 | Tamapin C8I | AFCNLRRIELSCRSLGLLGKCIGEECKCVPY |
| 142 | Tamapin C8K | AFCNLRRKELSCRSLGLLGKCIGEECKCVPY |
| 143 | Tamapin C8L | AFCNLRRLELSCRSLGLLGKCIGEECKCVPY |
| 144 | Tamapin C8M | AFCNLRRMELSCRSLGLLGKCIGEECKCVPY |
| 145 | Tamapin C8N | AFCNLRRNELSCRSLGLLGKCIGEECKCVPY |
| 146 | Tamapin C8P | AFCNLRRPELSCRSLGLLGKCIGEECKCVPY |
| 147 | Tamapin C8Q | AFCNLRRQELSCRSLGLLGKCIGEECKCVPY |
| 148 | Tamapin C8R | AFCNLRRREISCRSLGLLGKCIGEECKCYPY |
| 149 | Tamapin C8S | AFCNLRRSELSCRSLGLLGKCIGEECKCVPY |
| 150 | Tamapin C8T | AFCNLRRTELSCRSLGLLGKCIGEECKCVPY |
| 151 | Tamapin C8V | AFCNLRRVELSCRSLGLLGKCIGEECKCVPY |
| 152 | Tamapin C8W | AFCNLRRWELSCRSLGLLGKCIGEECKCVPY |
| 153 | Tamapin C8Y | AFCNLRRYELSCRSLGLLGKCIGEECKCVPY |
| 154 | Tamapin E9A | AFCNLRRCALSCRSLGLLGKCIGEECKCVPY |
| 155 | Tamapin E9C | AFCNLRRCCLSCRSLGLLGKCIGEECKCVPY |
| 156 | Tamapin E9D | AFCNLRRCDLSCRSLGLLGKCIGEECKCVPY |
| 157 | Tamapin E9F | AFCNLRRCFLSCRSLGLLGKCIGEECKCVPY |
| 158 | Tamapin E9G | AFCNLRRCGLSCRSLGLLGKCIGEECKCVPY |
| 159 | Tamapin E9H | AFCNLRRCHLSCRSLGLLGKCIGEECKCVPY |
| 160 | Tamapin E9I | AFCNLRRCILSCRSLGLLGKCIGEECKCVPY |
| 161 | Tamapin E9K | AFCNLRRCKLSCRSLGLLGKCIGEECKCVPY |
| 162 | Tamapin E9L | AFCNLRRCLLSCRSLGLLGKCIGEECKCVPY |
| 163 | Tamapin E9M | AFCNLRRCMLSCRSLGLLGKCIGEECKCVPY |
| 164 | Tamapin E9N | AFCNLRRCNLSCRSLGLLGKCIGEECKCVPY |
| 165 | Tamapin E9P | AFCNLRRCPLSCRSLGLLGKCIGEECKCVPY |
| 166 | Tamapin E9Q | AFCNLRRCQLSCRSLGLLGKCIGEECKCVPY |
| 167 | Tamapin E9R | AFCNLRRCRLSCRSLGLLGKCIGEECKCVPY |
| 168 | Tamapin E9S | AFCNLRRCSLSCRSLGLLGKCIGEECKCVPY |
| 169 | Tamapin E9T | AFCNLRRCTLSCRSLGLLGKCIGEECKCVPY |
| 170 | Tamapin E9V | AFCNLRRCVLSCRSLGLLGKCIGEECKCVPY |
| 171 | Tamapin E9W | AFCNLRRCWLSCRSLGLLGKCIGEECKCVPY |
| 172 | Tamapin E9Y | AFCNLRRCYLSCRSIGLLGKCIGEECKCVPY |
| 173 | Tamapin L10A | AFCNLRRCEASCRSLGLLGKCIGEECKCVPY |
| 174 | Tamapin L10C | AFCNLRRCECSCRSLGLLGKCIGEECKCVPY |
| 175 | Tamapin L10D | AFCNLRRCEDSCRSLGLLGKCIGEECKCVPY |
| 176 | Tamapin L10E | AFCNLRRCEESCRSLGLLGKCIGEECKCVPY |
| 177 | Tamapin L10F | AFCNLRRCEFSCRSLGLLGKCIGEECKCVPY |
| 178 | Tamapin L10G | AFCNLRRCEGSCRSLGLLGKCIGEECKCVPY |
| 179 | Tamapin L10H | AFCNLRRCEHSCRSLGLLGKCIGEECKCVPY |
| 180 | Tamapin L10I | AFCNLRRCEISCRSLGLLGKCIGEECKCVPY |
| 181 | Tamapin L10K | AFCNLRRCEKSCRSLGLLGKCIGEECKCVPY |
| 182 | Tamapin L10M | AFCNLRRCEMSCRSLGLLGKCIGEECKCVPY |
| 183 | Tamapin L10N | AFCNLRRCENSCRSLGLLGKCIGEECKCVPY |
| 184 | Tamapin L10P | AFCNLRRCEPSCRSLGLLGKCIGEECKCVPY |
| 185 | Tamapin L10Q | AFCNLRRCEQSCRSLGLLGKCIGEECKCVPY |
| 186 | Tamapin L10R | AFCNLRRCERSCRSLGLLGKCIGEECKCVPY |
| 187 | Tamapin L10S | AFCNLRRCESSCRSLGLLGKCIGEECKCVPY |
| 188 | Tamapin L10T | AFCNLRRCETSCRSLGLLGKCIGEECKCVPY |
| 189 | Tamapin L10V | AFCNLRRCEVSCRSLGLLGKCIGEECKCVPY |
| 190 | Tamapin L10W | AFCNLRRCEWSCRSLGLLGKCIGEECKCVPY |
| 191 | Tamapin L10Y | AFCNLRRCEYSCRSLGLLGKCIGEECKCVPY |
| 192 | Tamapin S11A | AFCNLRRCELACRSLGLLGKCIGEECKCVPY |
| 193 | Tamapin S11C | AFCNLRRCELCCRSLGLLGKCIGEECKCVPY |
| 194 | Tamapin S11D | AFCNLRRCELDCRSLGLLGKCIGEECKCVPY |
| 195 | Tamapin S11E | AFCNLRRCELECRSLGLLGKCIGEECKCVPY |
| 196 | Tamapin S11F | AFCNLRRCELFCRSLGLLGKCIGEECKCVPY |
| 197 | Tamapin S11G | AFCNLRRCELGCRSLGLLGKCIGEECKCVPY |
| 198 | Tamapin S11H | AFCNLRRCELHCRSLGLLGKCIGEECKCVPY |
| 199 | Tamapin S11I | AFCNLRRCELICRSLGLLGKCIGEECKCVPY |
| 200 | Tamapin S11K | AFCNLRRCELKCRSLGLLGKCIGEECKCVPY |
| 201 | Tamapin S11L | AFCNLRRCELLCRSLGLLGKCIGEECKCVPY |
| 202 | Tamapin S11M | AFCNLRRCELMCRSLGLLGKCIGEECKCVPY |
| 203 | Tamapin S11N | AFCNLRRCELNCRSLGLLGKCIGEECKCVPY |
| 204 | Tamapin S11P | AFCNLRRCELPCRSLGLLGKCIGEECKCVPY |
| 205 | Tamapin S11Q | AFCNLRRCELQCRSLGLLGKCIGEECKCVPY |
| 206 | Tamapin S11R | AFCNLRRCELRCRSLGLLGKCIGEECKCVPY |
| 207 | Tamapin S11T | AFCNLRRCELTCRSLGLLGKCIGEECKCVPY |
| 208 | Tamapin S11V | AFCNLRRCELVCRSLGLLGKCIGEECKCVPY |
| 209 | Tamapin S11W | AFCNLRRCELWCRSLGLLGKCIGEECKCVPY |
| 210 | Tamapin S11Y | AFCNLRRCELYCRSLGLLGKCIGEECKCVPY |
| 211 | Tamapin C12A | AFCNLRRCELSARSLGLLGKCIGEECKCVPY |
| 212 | Tamapin C12D | AFCNLRRCELSDRSLGLLGKCIGEECKCVPY |
| 213 | Tamapin C12E | AFCNLRRCELSERSLGLLGKCIGEECKCVPY |
| 214 | Tamapin C12F | AFCNLRRCELSFRSLGLLGKCIGEECKCVPY |
| 215 | Tamapin C12G | AFCNLRRCELSGRSLGLLGKCIGEECKCVPY |
| 216 | Tamapin C12H | AFCNLRRCELSHRSLGLLGKCIGEECKCVPY |

TABLE 1-continued

| Item | Designation | Sequence |
|---|---|---|
| 217 | Tamapin C12I | AFCNLRRCELSIRSLGLLGKCIGEECKCVPY |
| 218 | Tamapin C12K | AFCNLRRCELSKRSLGLLGKCIGEECKCVPY |
| 219 | Tamapin C12L | AFCNLRRCELSLRSLGLLGKCIGEECKCVPY |
| 220 | Tamapin C12M | AFCNLRRCELSMRSLGLLGKCIGEECKCVPY |
| 221 | Tamapin C12N | AFCNLRRCELSNRSLGLLGKCIGEECKCVPY |
| 222 | Tamapin C12P | AFCNLRRCELSPRSLGLLGKCIGEECKCVPY |
| 223 | Tamapin C12Q | AFCNLRRCELSQRSLGLLGKCIGEECKCVPY |
| 224 | Tamapin C12R | AFCNLRRCELSRRSLGLLGKCIGEECKCVPY |
| 225 | Tamapin C12S | AFCNLRRCELSSRSLGLLGKCIGEECKCVPY |
| 226 | Tamapin C12T | AFCNLRRCELSTRSLGLLGKCIGEECKCVPY |
| 227 | Tamapin C12V | AFCNLRRCELSVRSLGLLGKCIGEECKCVPY |
| 228 | Tamapin C12W | AFCNLRRCELSWRSLGLLGKCIGEECKCVPY |
| 229 | Tamapin C12Y | AFCNLRRCELSYRSLGLLGKCIGEECKCVPY |
| 230 | Tamapin R13A | AFCNLRRCELSCASLGLLGKCIGEECKCVPY |
| 231 | Tamapin R13C | AFCNLRRCELSCCSLGLLGKCIGEECKCVPY |
| 232 | Tamapin R13D | AFCNLRRCELSCDSLGLLGKCIGEECKCVPY |
| 233 | Tamapin R13E | AFCNLRRCELSCESLGLLGKCIGEECKCVPY |
| 234 | Tamapin R13F | AFCNLRRCELSCFSLGLLGKCIGEECKCVPY |
| 235 | Tamapin R13G | AFCNLRRCELSCGSLGLLGKCIGEECKCVPY |
| 236 | Tamapin R13H | AFCNLRRCELSCHSLGLLGKCIGEECKCVPY |
| 237 | Tamapin R13I | AFCNLRRCELSCISLGLLGKCIGEECKCVPY |
| 238 | Tamapin R13K | AFCNLRRCELSCKSLGLLGKCIGEECKCVPY |
| 239 | Tamapin R13L | AFCNLRRCELSCLSLGLLGKCIGEECKCVPY |
| 240 | Tamapin R13M | AFCNLRRCELSCMSLGLLGKCIGEECKCVPY |
| 241 | Tamapin R13N | AFCNLRRCELSCNSLGLLGKCIGEECKCVPY |
| 242 | Tamapin R13P | AFCNLRRCELSCPSLGLLGKCIGEECKCVPY |
| 243 | Tamapin R13Q | AFCNLRRCELSCQSLGLLGKCIGEECKCVPY |
| 244 | Tamapin R13S | AFCNLRRCELSCSSLGLLGKCIGEECKCVPY |
| 245 | Tamapin R13T | AFCNLRRCELSCTSLGLLGKCIGEECKCVPY |
| 246 | Tamapin R13V | AFCNLRRCELSCVSLGLLGKCIGEECKCVPY |
| 247 | Tamapin R13W | AFCNLRRCELSCWSLGLLGKCIGEECKCVPY |
| 248 | Tamapin R13Y | AFCNLRRCELSCYSLGLLGKCIGEECKCVPY |
| 249 | Tamapin S14A | AFCNLRRCELSCRALGLLGKCIGEECKCVPY |
| 250 | Tamapin S14C | AFCNLRRCELSCRCLGLLGKCIGEECKCVPY |
| 251 | Tamapin S14D | AFCNLRRCELSCRDLGLLGKCIGEECKCVPY |
| 252 | Tamapin S14E | AFCNLRRCELSCRELGLLGKCIGEECKCVPY |
| 253 | Tamapin S14F | AFCNLRRCELSCRFLGLLGKCIGEECKCVPY |
| 254 | Tamapin S14G | AFCNLRRCELSCRGLGLLGKCIGEECKCVPY |
| 255 | Tamapin S14H | AFCNLRRCELSCRHLGLLGKCIGEECKCVPY |
| 256 | Tamapin S14I | AFCNLRRCELSCRILGLLGKCIGEECKCVPY |
| 257 | Tamapin S14K | AFCNLRRCELSCRKLGLLGKCIGEECKCVPY |
| 258 | Tamapin S14L | AFCNLRRCELSCRLLGLLGKCIGEECKCVPY |
| 259 | Tamapin S14M | AFCNLRRCELSCRMLGLLGKCIGEECKCVPY |
| 260 | Tamapin S14N | AFCNLRRCELSCRNLGLLGKCIGEECKCVPY |
| 261 | Tamapin S14P | AFCNLRRCELSCRPLGLLGKCIGEECKCVPY |
| 262 | Tamapin S14Q | AFCNLRRCELSCRQLGLLGKCIGEECKCVPY |
| 263 | Tamapin S14R | AFCNLRRCELSCRRLGLLGKCIGEECKCVPY |
| 264 | Tamapin S14T | AFCNLRRCELSCRTLGLLGKCIGEECKCVPY |
| 265 | Tamapin S14V | AFCNLRRCELSCRVLGLLGKCIGEECKCVPY |
| 266 | Tamapin S14V | AFCNLRRCELSCRWLGLLGKCIGEECKCVPY |
| 267 | Tamapin S14Y | AFCNLRRCELSCRYLGLLGKCIGEECKCVPY |
| 268 | Tamapin L15A | AFCNLRRCELSCRSAGLLGKCIGEECKCVPY |
| 269 | Tamapin L15C | AFCNLRRCELSCRSCGLLGKCIGEECKCVPY |
| 270 | Tamapin L15D | AFCNLRRCELSCRSDGLLGKCIGEECKCVPY |
| 271 | Tamapin L15E | AFCNLRRCELSCRSEGLLGKCIGEECKCVPY |
| 272 | Tamapin L15F | AFCNLRRCELSCRSFGLLGKCIGEECKCVPY |
| 273 | Tamapin L15G | AFCNLRRCELSCRSGGLLGKCIGEECKCVPY |
| 274 | Tamapin L15H | AFCNLRRCELSCRSHGLLGKCIGEECKCVPY |
| 275 | Tamapin L15I | AFCNLRRCELSCRSIGLLGKCIGEECKCVPY |
| 276 | Tamapin L15K | AFCNLRRCELSCRSKGLLGKCIGEECKCVPY |
| 277 | Tamapin L15M | AFCNLRRCELSCRSMGLLGKCIGEECKCVPY |
| 278 | Tamapin L15N | AFCNLRRCELSCRSNGLLGKCIGEECKCVPY |
| 279 | Tamapin L15P | AFCNLRRCELSCRSPGLLGKCIGEECKCVPY |
| 280 | Tamapin L15Q | AFCNLRRCELSCRSQGLLGKCIGEECKCVPY |
| 281 | Tamapin L15R | AFCNLRRCELSCRSRGLLGKCIGEECKCVPY |
| 282 | Tamapin L15S | AFCNLRRCELSCRSSGLLGKCIGEECKCVPY |
| 283 | Tamapin L15T | AFCNLRRCELSCRSTGLLGKCIGEECKCVPY |
| 284 | Tamapin L15V | AFCNLRRCELSCRSVGLLGKCIGEECKCVPY |
| 285 | Tamapin L15W | AFCNLRRCELSCRSWGLLGKCIGEECKCVPY |
| 286 | Tamapin L15Y | AFCNLRRCELSCRSYGLLGKCIGEECKCVPY |
| 287 | Tamapin G16A | AFCNLRRCELSCRSLALLGKCIGEECKCVPY |
| 288 | Tamapin G16C | AFCNLRRCELSCRSLCLLGKCIGEECKCVPY |
| 289 | Tamapin G16D | AFCNLRRCELSCRSLDLLGKCIGEECKCVPY |
| 290 | Tamapin G16E | AFCNLRRCELSCRSLELLGKCIGEECKCVPY |
| 291 | Tamapin G16F | AFCNLRRCELSCRSLFLLGKCIGEECKCVPY |
| 292 | Tamapin G16H | AFCNLRRCELSCRSLHLLGKCIGEECKCVPY |
| 293 | Tamapin G16I | AFCNLRRCELSCRSLILLGKCIGEECKCVPY |
| 294 | Tamapin G16K | AFCNLRRCELSCRSLKLLGKCIGEECKCVPY |

TABLE 1-continued

| Item | Designation | Sequence |
|------|-------------|----------|
| 295 | Tamapin G16L | AFCNLRRCELSCRSLLLLGKCIGEECKCVPY |
| 296 | Tamapin G16M | AFCNLRRCELSCRSLMLLGKCIGEECKCVPY |
| 297 | Tamapin G16N | AFCNLRRCELSCRSLNLLGKCIGEECKCVPY |
| 298 | Tamapin G16P | AFCNLRRCELSCRSLPLLGKCIGEECKCVPY |
| 299 | Tamapin G16Q | AFCNLRRCELSCRSLQLLGKCIGEECKCVPY |
| 300 | Tamapin G16R | AFCNLRRCELSCRSLRLLGKCIGEECKCVPY |
| 301 | Tamapin G16S | AFCNLRRCELSCRSLSLLGKCIGEECKCVPY |
| 302 | Tamapin G16T | AFCNLRRCELSCRSLTLLGKCIGEECKCVPY |
| 303 | Tamapin G16V | AFCNLRRCELSCRSLVLLGKCIGEECKCVPY |
| 304 | Tamapin G16W | AFCNLRRCELSCRSLWLLGKCIGEECKCVPY |
| 305 | Tamapin G16Y | AFCNLRRCELSCRSLYLLGKCIGEECKCVPY |
| 306 | Tamapin L17A | AFCNLRRCELSCRSLGALGKCIGEECKCVPY |
| 307 | Tamapin L17C | AFCNLRRCELSCRSLGCLGKCIGEECKCVPY |
| 308 | Tamapin L17D | AFCNLRRCELSCRSLGDLGKCIGEECKCVPY |
| 309 | Tamapin L17E | AFCNLRRCELSCRSLGELGKCIGEECKCVPY |
| 310 | Tamapin L17F | AFCNLRRCELSCRSLGFLGKCIGEECKCVPY |
| 311 | Tamapin L17G | AFCNLRRCELSCRSLGGLGKCIGEECKCVPY |
| 312 | Tamapin L17H | AFCNLRRCELSCRSLGHLGKCIGEECKCVPY |
| 313 | Tamapin L17I | AFCNLRRCELSCRSLGILGKCIGEECKCVPY |
| 314 | Tamapin L17K | AFCNLRRCELSCRSLGKLGKCIGEECKCVPY |
| 315 | Tamapin L17M | AFCNLRRCELSCRSLGMLGKCIGEECKCVPY |
| 316 | Tamapin L17N | AFCNLRRCELSCRSLGNLGKCIGEECKCVPY |
| 317 | Tamapin L17P | AFCNLRRCELSCRSLGPLGKCIGEECKCVPY |
| 318 | Tamapin L17Q | AFCNLRRCELSCRSLGQLGKCIGEECKCVPY |
| 319 | Tamapin L17R | AFCNLRRCELSCRSLGRLGKCIGEECKCVPY |
| 320 | Tamapin L17S | AFCNLRRCELSCRSLGSLGKCIGEECKCVPY |
| 321 | Tamapin L17T | AFCNLRRCELSCRSLGTLGKCIGEECKCVPY |
| 322 | Tamapin L17V | AFCNLRRCELSCRSLGVLGKCIGEECKCVPY |
| 323 | Tamapin L17W | AFCNLRRCELSCRSLGWLGKCIGEECKCVPY |
| 324 | Tamapin L17Y | AFCNLRRCELSCRSLGYLGKCIGEECKCVPY |
| 325 | Tamapin L18A | AFCNLRRCELSCRSLGLAGKCIGEECKCVPY |
| 326 | Tamapin L18C | AFCNLRRCELSCRSLGLCGKCIGEECKCVPY |
| 327 | Tamapin L18D | AFCNLRRCELSCRSLGLDGKCIGEECKCVPY |
| 328 | Tamapin L18E | AFCNLRRCELSCRSLGLEGKCIGEECKCVPY |
| 329 | Tamapin L18F | AFCNLRRCELSCRSLGLFGKCIGEECKCVPY |
| 330 | Tamapin L18G | AFCNLRRCELSCRSLGLGGKCIGEECKCVPY |
| 331 | Tamapin L18H | AFCNLRRCELSCRSLGLHGKCIGEECKCVPY |
| 332 | Tamapin L18I | AFCNLRRCELSCRSLGLIGKCIGEECKCVPY |
| 333 | Tamapin L18K | AFCNLRRCELSCRSLGLKGKCIGEECKCVPY |
| 334 | Tamapin L18M | AFCNLRRCELSCRSLGLMGKCIGEECKCVPY |
| 335 | Tamapin L18N | AFCNLRRCELSCRSLGLNGKCIGEECKCVPY |
| 336 | Tamapin L18M | AFCNLRRCELSCRSLGLPGKCIGEECKCVPY |
| 337 | Tamapin L18Q | AFCNLRRCELSCRSLGLQGKCIGEECKCVPY |
| 338 | Tamapin L18R | AFCNLRRCELSCRSLGLRGKCIGEECKCVPY |
| 339 | Tamapin L18S | AFCNLRRCELSCRSLGLSGKCIGEECKCVPY |
| 340 | Tamapin L18T | AFCNLRRCELSCRSLGLTGKCIGEECKCVPY |
| 341 | Tamapin L18V | AFCNLRRCELSCRSLGLVGKCIGEECKCVPY |
| 342 | Tamapin L18W | AFCNLRRCELSCRSLGLWGKCIGEECKCVPY |
| 343 | Tamapin L18Y | AFCNLRRCELSCRSLGLYGKCIGEECKCVPY |
| 344 | Tamapin G19A | AFCNLRRCELSCRSLGLLAKCIGEECKCVPY |
| 345 | Tamapin G19C | AFCNLRRCELSCRSLGLLCKCIGEECKCVPY |
| 346 | Tamapin G19D | AFCNLRRCELSCRSLGLLDKCIGEECKCVPY |
| 347 | Tamapin G19E | AFCNIRRCELSCRSLGLLEKCIGEECKCVPY |
| 348 | Tamapin G19F | AFCNLRRCELSCRSLGLLFKCIGEECKCVPY |
| 349 | Tamapin G19H | AFCNLRRCELSCRSLGLLHKCIGEECKCVPY |
| 350 | Tamapin G19I | AFCNLRRCELSCRSLGLLIKCIGEECKCAPY |
| 351 | Tamapin G19K | AFCNLRRCELSCRSLGLLKKCIGEECKCVPY |
| 352 | Tamapin G19L | AFCNLRRCELSCRSLGLLLKCIGEECKCVPY |
| 353 | Tamapin G19M | AFCNLRRCELSCRSLGLLMKCIGEECKCAPY |
| 354 | Tamapin G19N | AFCNLRRCELSCRSLGLLNKCIGEECKCAPY |
| 355 | Tamapin G19P | AFCNLRRCELSCRSLGLITKCIGEECKCAPY |
| 356 | Tamapin G19Q | AFCNLRRCELSCRSLGLLQKCIGEECKCVPY |
| 357 | Tamapin G19R | AFCNLRRCELSCRSLGLLRKCIGEECKCVPY |
| 358 | Tamapin G19S | AFCNLRRCELSCRSLGLLSKCIGEECKCVPY |
| 359 | Tamapin G19T | AFCNLRRCELSCRSLGLLTKCIGEECKCVPY |
| 360 | Tamapin G19V | AFCNLRRCELSCRSLGLLVKCIGEECKCVPY |
| 361 | Tamapin G19W | AFCNLRRCELSCRSLGLLWKCIGEECKCVPY |
| 362 | Tamapin G19Y | AFCNLRRCELSCRSLGLLYKCIGEECKCVPY |
| 363 | Tamapin K20A | AFCNLRRCELSCRSLGLLGACIGEECKCVPY |
| 364 | Tamapin K20C | AFCNLRRCELSCRSLGLLGCCIGEECKCVPY |
| 365 | Tamapin K20D | AFCNLRRCELSCRSLGLLGDCIGEECKCVPY |
| 366 | Tamapin K20E | AFCNLRRCELSCRSLGLLGECIGEECKCVPY |
| 367 | Tamapin K20F | AFCNLRRCELSCRSLGLLGFCIGEECKCVPY |
| 368 | Tamapin K20G | AFCNLRRCELSCRSLGLLGGCIGEECKCVPY |
| 369 | Tamapin K20H | AFCNLRRCELSCRSLGLLGHCIGEECKCVPY |
| 370 | Tamapin K20I | AFCNLRRCELSCRSLGLLGICIGEECKCVPY |
| 371 | Tamapin K20L | AFCNLRRCELSCRSLGLLGLCIGEECKCVPY |
| 372 | Tamapin K20M | AFCNLRRCELSCRSLGLLGMCIGEECKCVPY |

TABLE 1-continued

| Item | Designation | Sequence |
|---|---|---|
| 373 | Tamapin K20N | AFCNLRRCELSCRSLGLLGNCIGEECKCVPY |
| 374 | Tamapin K20P | AFCNLRRCELSCRSLGLLGPCIGEECKCVPY |
| 375 | Tamapin K20Q | AFCNLRRCELSCRSLGLLGQCIGEECKCVPY |
| 376 | Tamapin K20R | AFCNLRRCELSCRSLGLLGRCIGEECKCVPY |
| 377 | Tamapin K20S | AFCNLRRCELSCRSLGLLGSCIGEECKCVPY |
| 378 | Tamapin K20T | AFCNLRRCELSCRSLGLLGTCIGEECKCVPY |
| 379 | Tamapin K20V | AFCNLRRCELSCRSLGLLGVCIGEECKCVPY |
| 380 | Tamapin K20W | AFCNLRRCELSCRSLGLLGWCIGEECKCVPY |
| 381 | Tamapin K20Y | AFCNLRRCELSCRSLGLLGYCIGEECKCVPY |
| 382 | Tamapin C21A | AFCNLRRCELSCRSLGLLGKAIGEECKCVPY |
| 383 | Tamapin C21D | AFCNLRRCELSCRSLGLLGKDIGEECKCVPY |
| 384 | Tamapin C21E | AFCNLRRCELSCRSLGLLGKEIGEECKCVPY |
| 385 | Tamapin C21F | AFCNLRRCELSCRSLGLLGKFIGEECKCVPY |
| 386 | Tamapin C21G | AFCNLRRCELSCRSLGLLGKGIGEECKCVPY |
| 387 | Tamapin C21H | AFCNLRRCELSCRSLGLLGKIIGEECKCVPY |
| 388 | Tamapin C21I | AFCNLRRCELSCRSLGLLGKIIGEECKCVPY |
| 389 | Tamapin C21K | AFCNLRRCELSCRSLGLLGKKIGEECKCVPY |
| 390 | Tamapin C21L | AFCNLRRCELSCRSLGLLGKIIGEECKCVPY |
| 391 | Tamapin C21M | AFCNLRRCELSCRSLGLLGKMIGEECKCVPY |
| 392 | Tamapin C21N | AFCNLRRCELSCRSLGLLGKNIGEECKCVPY |
| 393 | Tamapin C21P | AFCNLRRCELSCRSLGLLGKPIGEECKCVPY |
| 394 | Tamapin C21Q | AFCNLRRCELSCRSLGLLGKQIGEECKCVPY |
| 395 | Tamapin C21R | AFCNLRRCELSCRSLGLLGKRIGEECKCVPY |
| 396 | Tamapin C21S | AFCNLRRCELSCRSLGLLGKSIGEECKCVPY |
| 397 | Tamapin C21T | AFCNLRRCELSCRSLGLLGKTIGEECKCVPY |
| 398 | Tamapin C21V | AFCNLRRCELSCRSLGLLGKVIGEECKCVPY |
| 399 | Tamapin C21W | AFCNLRRCELSCRSLGLLGKWIGEECKCVPY |
| 400 | Tamapin C21Y | AFCNLRRCELSCRSLGLLGKYIGEECKCVPY |
| 401 | Tamapin I22A | AFCNLRRCELSCRSLGLLGKCAGEECKCVPY |
| 402 | Tamapin I22C | AFCNLRRCELSCRSLGLLGKCCGEECKCVPY |
| 403 | Tamapin I22D | AFCNLRRCELSCRSLGLLGKCDGEECKCVPY |
| 404 | Tamapin I22E | AFCNLRRCELSCRSLGLLGKCEGEECKCVPY |
| 405 | Tamapin I22F | AFCNLRRCELSCRSLGLLGKCFGEECKCVPY |
| 406 | Tamapin I22G | AFCNLRRCELSCRSLGLLGKCGGEECKCVPY |
| 407 | Tamapin I22H | AFCNLRRCELSCRSLGLLGKCHGEECKCVPY |
| 408 | Tamapin I22K | AFCNLRRCELSCRSLGLLGKCKGEECKCVPY |
| 409 | Tamapin I22L | AFCNLRRCELSCRSLGLLGKCLGEECKCVPY |
| 410 | Tamapin I22M | AFCNLRRCELSCRSLGLLGKCMGEECKCVPY |
| 411 | Tamapin I22N | AFCNLRRCELSCRSLGLLGKCNGEECKCVPY |
| 412 | Tamapin I22P | AFCNLRRCELSCRSLGLLGKCPGEECKCVPY |
| 413 | Tamapin I22Q | AFCNLRRCELSCRSLGLLGKCQGEECKCVPY |
| 414 | Tamapin I22R | AFCNLRRCELSCRSLGLLGKCRGEECKCVPY |
| 415 | Tamapin I22S | AFCNLRRCELSCRSLGLLGKCSGEECKCVPY |
| 416 | Tamapin I22T | AFCNLRRCELSCRSLGLLGKCTGEECKCVPY |
| 417 | Tamapin I22V | AFCNLRRCELSCRSLGLLGKCVGEECKCVPY |
| 418 | Tamapin I22W | AFCNLRRCELSCRSLGLLGKCWGEECKCVPY |
| 419 | Tamapin I22Y | AFCNLRRCELSCRSLGLLGKCYGEECKCVPY |
| 420 | Tamapin G23A | AFCNLRRCELSCRSLGIIGKCIAEECKCVPY |
| 421 | Tamapin G23C | AFCNLRRCELSCRSLGIIGKCICEECKCVPY |
| 422 | Tamapin G23D | AFCNLRRCELSCRSLGLLGKCIDEECKCVPY |
| 423 | Tamapin G23E | AFCNLRRCELSCRSLGLLGKCIEEECKCVPY |
| 424 | Tamapin G23F | AFCNLRRCELSCRSLGIIGKCIFEECKCVPY |
| 425 | Tamapin G23H | AFCNLRRCELSCRSLGIIGKCIHEECKCVPY |
| 426 | Tamapin G23I | AFCNLRRCELSCRSLGIIGKCIIEECKCVPY |
| 427 | Tamapin G23K | AFCNLRRCELSCRSLGLLGKCIKEECKCVPY |
| 428 | Tamapin G23L | AFCNLRRCELSCRSLGLLGKCILEECKCVPY |
| 429 | Tamapin G23M | AFCNLRRCELSCRSLGLLGKCIMEECKCVPY |
| 430 | Tamapin G23N | AFCNLRRCELSCRSLGLLGKCINEECKCVPY |
| 431 | Tamapin G23P | AFCNLRRCELSCRSLGLLGKCIPEECKCVPY |
| 432 | Tamapin G23Q | AFCNLRRCELSCRSLGLLGKCIQEECKCVPY |
| 433 | Tamapin G23R | AFCNLRRCELSCRSLGLLGKCIREECKCVPY |
| 434 | Tamapin G23S | AFCNLRRCELSCRSLGLLGKCISEECKCVPY |
| 435 | Tamapin G23T | AFCNLRRCELSCRSLGLLGKCITEECKCVPY |
| 436 | Tamapin G23V | AFCNLRRCELSCRSLGLLGKCIVEECKCVPY |
| 437 | Tamapin G23W | AFCNLRRCELSCRSLGLLGKCIWEECKCVPY |
| 438 | Tamapin G23Y | AFCNLRRCELSCRSLGLLGKCIYEECKCVPY |
| 439 | Tamapin E24A | AFCNLRRCELSCRSLGLLGKCIGAECKCVPY |
| 440 | Tamapin E24C | AFCNLRRCELSCRSLGLLGKCIGCECKCVPY |
| 441 | Tamapin E24D | AFCNLRRCELSCRSLGLLGKCIGDECKCVPY |
| 442 | Tamapin E24F | AFCNLRRCELSCRSLGLLGKCIGFECKCVPY |
| 443 | Tamapin E24G | AFCNLRRCELSCRSLGLLGKCIGGECKCVPY |
| 444 | Tamapin E24H | AFCNLRRCELSCRSLGLLGKCIGHECKCVPY |
| 445 | Tamapin E24I | AFCNLRRCELSCRSLGLLGKCIGLECKCVPY |
| 446 | Tamapin E24K | AFCNLRRCELSCRSLGLLGKCIGKECKCVPY |
| 447 | Tamapin E24L | AFCNLRRCELSCRSLGLLGKCIGLECKCVPY |
| 448 | Tamapin E24M | AFCNLRRCELSCRSLGLLGKCIGMECKCVPY |
| 449 | Tamapin E24N | AFCNLRRCELSCRSLGLLGKCIGNECKCVPY |
| 450 | Tamapin E24P | AFCNLRRCELSCRSLGLLGKCIGPECKCVPY |

TABLE 1-continued

| Item | Designation | Sequence |
|---|---|---|
| 451 | Tamapin E24Q | AFCNLRRCELSCRSLGLLGKCIGQECKCVPY |
| 452 | Tamapin E24R | AFCNLRRCELSCRSLGLLGKCIGRECKCVPY |
| 453 | Tamapin E24S | AFCNLRRCELSCRSLGLLGKCIGSECKCVPY |
| 454 | Tamapin E24T | AFCNLRRCELSCRSLGLLGKCIGTECKCVPY |
| 455 | Tamapin E24V | AFCNLRRCELSCRSLGLLGKCIGVECKCVPY |
| 456 | Tamapin E24W | AFCNLRRCELSCRSLGLLGKCIGWECKCVPY |
| 457 | Tamapin E24Y | AFCNLRRCELSCRSLGLLGKCIGYECKCVPY |
| 458 | Tamapin E25A | AFCNLRRCELSCRSLGLLGKCIGEACKCVPY |
| 459 | Tamapin E25C | AFCNLRRCELSCRSLGLLGKCIGECCKCVPY |
| 460 | Tamapin E25D | AFCNLRRCELSCRSLGLLGKCIGEDCKCVPY |
| 461 | Tamapin E25F | AFCNLRRCELSCRSLGLLGKCIGEFCKCVPY |
| 462 | Tamapin E25G | AFCNLRRCELSCRSLGLLGKCIGEGCKCVPY |
| 463 | Tamapin E25H | AFCNLRRCELSCRSLGLLGKCIGEHCKCVPY |
| 464 | Tamapin E25I | AFCNLRRCELSCRSLGLLGKCIGEICKCVPY |
| 465 | Tamapin E25K | AFCNLRRCELSCRSLGLLGKCIGEKCKCVPY |
| 466 | Tamapin E25L | AFCNLRRCELSCRSLGLLGKCIGELCKCVPY |
| 467 | Tamapin E25M | AFCNLRRCELSCRSLGLLGKCIGEMCKCVPY |
| 468 | Tamapin E25N | AFCNLRRCELSCRSLGLLGKCIGENCKCVPY |
| 469 | Tamapin E25P | AFCNLRRCELSCRSLGLLGKCIGEPCKCVPY |
| 470 | Tamapin E25Q | AFCNLRRCELSCRSLGLLGKCIGEQCKCVPY |
| 471 | Tamapin E25R | AFCNLRRCELSCRSLGLLGKCIGERCKCVPY |
| 472 | Tamapin E25S | AFCNLRRCELSCRSLGLLGKCIGESCKCVPY |
| 473 | Tamapin E25T | AFCNLRRCELSCRSLGLLGKCIGETCKCVPY |
| 474 | Tamapin E25V | AFCNLRRCELSCRSLGLLGKCIGEVCKCVPY |
| 475 | Tamapin E25W | AFCNLRRCELSCRSLGLLGKCIGEWCKCVPY |
| 476 | Tamapin E25Y | AFCNLRRCELSCRSLGLLGKCIGEYCKCVPY |
| 477 | Tamapin C26A | AFCNLRRCELSCRSLGLLGKCIGEEAKCVPY |
| 478 | Tamapin C26D | AFCNLRRCELSCRSLGLLGKCIGEEDKCVPY |
| 479 | Tamapin C26E | AFCNLRRCELSCRSLGLLGKCIGEEEKCVPY |
| 480 | Tamapin C26F | AFCNLRRCELSCRSLGLLGKCIGEEFKCVPY |
| 481 | Tamapin C26G | AFCNLRRCELSCRSLGLLGKCIGEEGKCVPY |
| 482 | Tamapin C26H | AFCNLRRCELSCRSLGLLGKCIGEEHKCVPY |
| 483 | Tamapin C26I | AFCNLRRCELSCRSLGLLGKCIGEEIKCVPY |
| 484 | Tamapin C26K | AFCNLRRCELSCRSLGLLGKCIGEEKKCVPY |
| 485 | Tamapin C26L | AFCNLRRCELSCRSLGLLGKCIGEELKCVPY |
| 486 | Tamapin C26M | AFCNLRRCELSCRSLGLLGKCIGEEMKCVPY |
| 487 | Tamapin C26N | AFCNLRRCELSCRSLGLLGKCIGEENKCVPY |
| 488 | Tamapin C26P | AFCNLRRCELSCRSLGLLGKCIGEEPKCVPY |
| 489 | Tamapin C26Q | AFCNLRRCELSCRSLGLLGKCIGEEQKCVPY |

TABLE 1-continued

| Item | Designation | Sequence |
|---|---|---|
| 490 | Tamapin C26R | AFCNLRRCELSCRSLGLLGKCIGEERKCVPY |
| 491 | Tamapin C26S | AFCNLRRCELSCRSLGLLGKCIGEESKCVPY |
| 492 | Tamapin C26T | AFCNLRRCELSCRSLGLLGKCIGEETKCVPY |
| 493 | Tamapin C26V | AFCNLRRCELSCRSLGLLGKCIGEEVKCVPY |
| 494 | Tamapin C26W | AFCNLRRCELSCRSLGLLGKCIGEEWKCVPY |
| 495 | Tamapin C26Y | AFCNLRRCELSCRSLGLLGKCIGEEYKCVPY |
| 496 | Tamapin K27A | AFCNLRRCELSCRSLGLLGKCIGEECACVPY |
| 497 | Tamapin K27C | AFCNLRRCELSCRSLGLLGKCIGEECCCVPY |
| 498 | Tamapin K27D | AFCNLRRCELSCRSLGLLGKCIGEECDCVPY |
| 499 | Tamapin K27E | AFCNLRRCELSCRSLGLLGKCIGEECECVPY |
| 500 | Tamapin K27F | AFCNLRRCELSCRSLGLLGKCIGEECFCVPY |
| 501 | Tamapin K27G | AFCNLRRCELSCRSLGLLGKCIGEECGCVPY |
| 502 | Tamapin K27H | AFCNLRRCELSCRSLGLLGKCIGEECHCVPY |
| 503 | Tamapin K27I | AFCNLRRCELSCRSLGLLGKCIGEECICVPY |
| 504 | Tamapin K27L | AFCNLRRCELSCRSLGLLGKCIGEECLCVPY |
| 505 | Tamapin K27M | AFCNLRRCELSCRSLGLLGKCIGEECMCVPY |
| 506 | Tamapin K27N | AFCNLRRCELSCRSLGLLGKCIGEECNCVPY |
| 507 | Tamapin K27P | AFCNLRRCELSCRSLGLLGKCIGEECPCVPY |
| 508 | Tamapin K27Q | AFCNLRRCELSCRSLGLLGKCIGEECQCVPY |
| 509 | Tamapin K27R | AFCNLRRCELSCRSLGLLGKCIGEECRCVPY |
| 510 | Tamapin K27S | AFCNLRRCELSCRSLGLLGKCIGEECSCVPY |
| 511 | Tamapin K27T | AFCNLRRCELSCRSLGLLGKCIGEECTCVPY |
| 512 | Tamapin K27V | AFCNLRRCELSCRSLGLLGKCIGEECVCVPY |
| 513 | Tamapin K27W | AFCNLRRCELSCRSLGLLGKCIGEECWCVPY |
| 514 | Tamapin K27Y | AFCNLRRCELSCRSLGLLGKCIGEECYCVPY |
| 515 | Tamapin C28A | AFCNLRRCELSCRSLGLLGKCIGEECKAVPY |
| 516 | Tamapin C28D | AFCNLRRCELSCRSLGLLGKCIGEECKDVPY |
| 517 | Tamapin C28E | AFCNLRRCELSCRSLGLLGKCIGEECKEVPY |
| 518 | Tamapin C28F | AFCNLRRCELSCRSLGLLGKCIGEECKFVPY |
| 519 | Tamapin C28G | AFCNLRRCELSCRSLGLLGKCIGEECKGVPY |
| 520 | Tamapin C28H | AFCNLRRCELSCRSLGLLGKCIGEECKHVPY |
| 521 | Tamapin C28I | AFCNLRRCELSCRSLGLLGKCIGEECKINPY |
| 522 | Tamapin C28K | AFCNLRRCELSCRSLGLLGKCIGEECKKVPY |
| 523 | Tamapin C28L | AFCNLRRCELSCRSLGLLGKCIGEECKLVPY |
| 524 | Tamapin C28M | AFCNLRRCELSCRSLGLLGKCIGEECKMVPY |
| 525 | Tamapin C28N | AFCNLRRCELSCRSLGLLGKCIGEECKNVPY |
| 526 | Tamapin C28P | AFCNLRRCELSCRSLGLLGKCIGEECKPVPY |
| 527 | Tamapin C28Q | AFCNLRRCELSCRSLGLLGKCIGEECKQVPY |
| 528 | Tamapin C28R | AFCNLRRCELSCRSLGLLGKCIGEECKRVPY |

TABLE 1-continued

| Item | Designation | Sequence |
|---|---|---|
| 529 | Tamapin C28S | AFCNLRRCELSCRSLGLLGKCIGEECKSVPY |
| 530 | Tamapin C28T | AFCNLRRCELSCRSLGLLGKCIGEECKTVPY |
| 531 | Tamapin C28V | AFCNLRRCELSCRSLGLLGKCIGEECKVVPY |
| 532 | Tamapin C28W | AFCNLRRCELSCRSLGLLGKCIGEECKWVPY |
| 533 | Tamapin C28Y | AFCNLRRCELSCRSLGLLGKCIGEECKYVPY |
| 534 | Tamapin V29A | AFCNLRRCELSCRSLGLLGKCIGEECKCAPY |
| 535 | Tamapin V29C | AFCNLRRCELSCRSLGLLGKCIGEECKCCPY |
| 536 | Tamapin V29D | AFCNLRRCELSCRSLGLLGKCIGEECKCDPY |
| 537 | Tamapin V29E | AFCNLRRCELSCRSLGLLGKCIGEECKCEPY |
| 538 | Tamapin V29F | AFCNLRRCELSCRSLGLLGKCIGEECKCFPY |
| 539 | Tamapin V29G | AFCNLRRCELSCRSLGLLGKCIGEECKCGPY |
| 540 | Tamapin V29H | AFCNLRRCELSCRSLGLLGKCIGEECKCHPY |
| 541 | Tamapin V29I | AFCNLRRCELSCRSLGLLGKCIGEECKCIPY |
| 542 | Tamapin V29K | AFCNLRRCELSCRSLGLLGKCIGEECKCKPY |
| 543 | Tamapin V29L | ARCNLRRCELSCRSLGLLGKCIGEECKCLPY |
| 544 | Tamapin V29M | AFCNLRRCELSCRSLGLLGKCIGEECKCMPY |
| 545 | Tamapin V29N | AFCNLRRCELSCRSLGLLGKCIGEECKCNPY |
| 546 | Tamapin V29P | AFCNLRRCELSCRSLGLLGKCIGEECKCPPY |
| 547 | Tamapin V29Q | AFCNLRRCELSCRSLGLLGKCIGEECKCQPY |
| 548 | Tamapin V29R | AFCNLRRCELSCRSLGLLGKCIGEECKCRPY |
| 549 | Tamapin V29S | AFCNLRRCELSCRSLGLLGKCIGEECKCSPY |
| 550 | Tamapin V29T | AFCNLRRCELSCRSLGLLGKC1GEECKCTPY |
| 551 | Tamapin V29W | AFCNLRRCELSCRSLGLLGKC1GEECKCWPY |
| 552 | Tamapin V29Y | AFCNLRRCELSCRSLGLLGKC1GEECKCYPY |
| 553 | Tamapin P30A | AFCNLRRCELSCRSLGLLGKCIGEECKCVAY |
| 554 | Tamapin P30C | AFCNLRRCELSCRSLGLLGKCIGEECKCVCY |
| 555 | Tamapin P30D | AFCNLRRCELSCRSLGLLGKCIGEECKCVDY |
| 556 | Tamapin P30E | AFCNLRRCELSCRSLGLLGKCIGEECKCVEY |
| 557 | Tamapin P30F | AFCNLRRCELSCRSLGLLGKCIGEECKCVFY |
| 558 | Tamapin P30G | AFCNLRRCELSCRSLGLLGKCIGEECKCVGY |
| 559 | Tamapin P30H | AFCNLRRCELSCRSLGLLGKCIGEECKCVHY |

TABLE 1-continued

| Item | Designation | Sequence |
|---|---|---|
| 560 | Tamapin P30I | AFCNLRRCELSCRSLGLLGKCIGEECKCVIY |
| 561 | Tamapin P30K | AFCNLRRCELSCRSLGLLGKCIGEECKCVKY |
| 562 | Tamapin P30L | AFCNLRRCELSCRSLGLLGKCIGEECKCVLY |
| 563 | Tamapin P30M | AFCNLRRCELSCRSLGLLGKCIGEECKCVMY |
| 564 | Tamapin P30N | AFCNLRRCELSCRSLGLLGKCIGEECKCVNY |
| 565 | Tamapin P30Q | AFCNLRRCELSCRSLGLLGKCIGEECKCVQY |
| 566 | Tamapin P30R | AFCNLRRCELSCRSLGLLGKCIGEECKCVRY |
| 567 | Tamapin P30S | AFCNLRRCELSCRSLGLLGKCIGEECKCVSY |
| 568 | Tamapin P30T | AFCNLRRCELSCRSLGLLGKCIGEECKCNTY |
| 569 | Tamapin P30V | AFCNLRRCELSCRSLGLLGKCIGEECKCVVY |
| 570 | Tamapin P30W | AFCNLRRCELSCRSLGLLGKCIGEECKCVWY |
| 571 | Tamapin P30Y | AFCNLRRCELSCRSLGLLGKCIGEECKCVYY |
| 572 | Tamapin Y31A | AFCNLRRCELSCRSLGLLGKCIGEECKCVPA |
| 573 | Tamapin Y31C | AFCNLRRCELSCRSLGLLGKCIGEECKCVPC |
| 574 | Tamapin Y31D | AFCNLRRCELSCRSLGLLGKCIGEECKCVPD |
| 575 | Tamapin Y31E | AFCNLRRCELSCRSLGLLGKCIGEECKCVPE |
| 576 | Tamapin Y31F | AFCNLRRCELSCRSLGLLGKCIGEECKCVPF |
| 577 | Tamapin Y31G | AFCNLRRCELSCRSLGLLGKCIGEECKCVPG |
| 578 | Tamapin Y31H | AFCNLRRCELSCRSLGLLGKCIGEECKCVPH |
| 579 | Tamapin Y31I | AFCNLRRCELSCRSLGLLGKCIGEECKCVPI |
| 580 | Tamapin Y31K | AFCNLRRCELSCRSLGLLGKCIGEECKCVPK |
| 581 | Tamapin Y31L | AFCNLRRCELSCRSLGLLGKCIGEECKCVPL |
| 582 | Tamapin Y31M | AFCNLRRCELSCRSLGLLGKCIGEECKCVPM |
| 583 | Tamapin Y31N | AFCNLRRCELSCRSLGLLGKCIGEECKCVPN |
| 584 | Tamapin Y31P | AFCNLRRCELSCRSLGLLGKCIGEECKCVPP |
| 585 | Tamapin Y31Q | AFCNLRRCELSCRSLGLLGKCIGEECKCVPQ |
| 586 | Tamapin Y31R | AFCNLRRCELSCRSLGLLGKCIGEECKCVPR |
| 587 | Tamapin Y31S | AFCNLRRCELSCRSLGLLGKCIGEECKCVPS |
| 588 | Tamapin Y31T | AFCNLRRCELSCRSLGLLGKCIGEECKCVPT |
| 589 | Tamapin Y31V | AFCNLRRCELSCRSLGLLGKCIGEECKCNPV |
| 590 | Tamapin Y31W | AFCNLRRCELSCRSLGLLGKCIGEECKCVPW |

The invention claimed is:

1. A method for treating a learning disability in a subject exposed to alcohol in utero or in a subject having fetal alcohol syndrome comprising administering tamapin or a tamapin analog to a subject in need thereof.

2. The method of claim 1, wherein the tamapin or tamapin analog has an amino acid sequence described by any one of SEQ ID NOS: 1-590.

3. The method of claim 1, wherein said subject has a learning disability selected from the group consisting of cognitive dysfunction, intellectual disability, dyspraxia, and mental retardation.

4. The method of claim 1, wherein the subject is a fetus.

5. The method of claim 1, wherein the subject-has been exposed to alcohol in utero.

6. The method of claim 1, wherein the subject has fetal alcohol syndrome.

7. The method of claim 1 that comprises administering the tamapin to the subject.

8. The method of claim 1 that comprises administering the tamapin analog to the subject.

9. The method of claim 1, wherein the subject is a fetus who has been exposed to alcohol and wherein the subject is administered tamapin.

10. The method of claim 1, wherein the subject has been exposed to ischemia.

* * * * *

SEQUENCE LISTING

<160> NUMBER OF SEQ ID NOS: 590

<210> SEQ ID NO 1
<211> LENGTH: 31
<212> TYPE: PRT
<213> ORGANISM: Mesobuthus tamalus

```
<400> SEQUENCE: 1

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Tamapin A1C

<400> SEQUENCE: 2

Cys Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Tamapin A1D

<400> SEQUENCE: 3

Asp Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 4
<211> LENGTH: 31
<212> TYPE: PRT
<213> ORGANISM: Artificial Sequence
<220> FEATURE:
<223> OTHER INFORMATION: Tamapin A1E

<400> SEQUENCE: 4

Glu Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 5
<211> LENGTH: 31
<212> TYPE: PRT
<213> ORGANISM: Artificial Sequence
<220> FEATURE:
<223> OTHER INFORMATION: Tamapin A1F

<400> SEQUENCE: 5

Phe Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 6
<211> LENGTH: 31
<212> TYPE: PRT
<213> ORGANISM: Artificial Sequence
<220> FEATURE:
<223> OTHER INFORMATION: Tamapin A1G
```

<400> SEQUENCE: 6

Gly Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 7
<211> LENGTH: 31
<212> TYPE: PRT
<213> ORGANISM: Artificial Sequence
<220> FEATURE:
<223> OTHER INFORMATION: Tamapin A1I

<400> SEQUENCE: 7

His Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Tamapin A1I

<400> SEQUENCE: 8

Ile Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 9
<211> LENGTH: 31
<212> TYPE: PRT
<213> ORGANISM: Artificial Sequence
<220> FEATURE:
<223> OTHER INFORMATION: Tamapin A1K

<400> SEQUENCE: 9

Lys Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 10
<211> LENGTH: 31
<212> TYPE: PRT
<213> ORGANISM: Artificial Sequence
<220> FEATURE:
<223> OTHER INFORMATION: Tamapin A1L

<400> SEQUENCE: 10

Leu Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 11
<211> LENGTH: 31
<212> TYPE: PRT
<213> ORGANISM: Artificial Sequence
<220> FEATURE:

<223> OTHER INFORMATION: Tamapin A1M

<400> SEQUENCE: 11

Met Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Tamapin A1N

<400> SEQUENCE: 12

Asn Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: Tamapin A1P

<400> SEQUENCE: 13

Pro Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: Tamapin A1Q

<400> SEQUENCE: 14

Gln Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: Tamapin A1R

<400> SEQUENCE: 15

Arg Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 16
<211> LENGTH: 31
<212> TYPE: PRT
<213> ORGANISM: Artificial Sequence -continued

```
<220> FEATURE:
<223> OTHER INFORMATION: Tamapin A1S

<400> SEQUENCE: 16

Ser Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Tamapin A1T

<400> SEQUENCE: 17

Thr Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Tamapin A1V

<400> SEQUENCE: 18

Val Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Tamapin A1W

<400> SEQUENCE: 19

Trp Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 20
<211> LENGTH: 31
<212> TYPE: PRT
<213> ORGANISM: Artificial Sequence
<220> FEATURE:
<223> OTHER INFORMATION: Tamapin A1Y

<400> SEQUENCE: 20

Tyr Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 21
<211> LENGTH: 31
<212> TYPE: PRT
```

```
<213> ORGANISM: Artificial Sequence
<220> FEATURE:
<223> OTHER INFORMATION: Tamapin F2A

<400> SEQUENCE: 21

Ala Ala Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 22
<211> LENGTH: 31
<212> TYPE: PRT
<213> ORGANISM: Artificial Sequence
<220> FEATURE:
<223> OTHER INFORMATION: Tamapin F2C

<400> SEQUENCE: 22

Ala Cys Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 23
<211> LENGTH: 31
<212> TYPE: PRT
<213> ORGANISM: Artificial Sequence
<220> FEATURE:
<223> OTHER INFORMATION: Tamapin F2D

<400> SEQUENCE: 23

Ala Asp Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 24
<211> LENGTH: 31
<212> TYPE: PRT
<213> ORGANISM: Artificial Sequence
<220> FEATURE:
<223> OTHER INFORMATION: Tamapin F2E

<400> SEQUENCE: 24

Ala Glu Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Tamapin F2G

<400> SEQUENCE: 25

Ala Gly Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 26
<211> LENGTH: 31
```

<212> TYPE: PRT
<213> ORGANISM: Artificial Sequence
<220> FEATURE:
<223> OTHER INFORMATION: Tamapin F2H

<400> SEQUENCE: 26

Ala His Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Tamapin F2I

<400> SEQUENCE: 27

Ala Ile Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Tamapin F2K

<400> SEQUENCE: 28

Ala Lys Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Tamapin F2L

<400> SEQUENCE: 29

Ala Leu Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Tamapin F2M

<400> SEQUENCE: 30

Ala Met Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 31

```
<211> LENGTH: 31
<212> TYPE: PRT
<213> ORGANISM: Artificial Sequence
<220> FEATURE:
<223> OTHER INFORMATION: Tamapin F2N

<400> SEQUENCE: 31

Ala Asn Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Tamapin F2P

<400> SEQUENCE: 32

Ala Pro Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Tamapin F2Q

<400> SEQUENCE: 33

Ala Gln Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Tamapin F2R

<400> SEQUENCE: 34

Ala Arg Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Tamapin F2S

<400> SEQUENCE: 35

Ala Ser Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

```
<210> SEQ ID NO 36
<211> LENGTH: 31
<212> TYPE: PRT
<213> ORGANISM: Artificial Sequence
<220> FEATURE:
<223> OTHER INFORMATION: Tamapin F2T

<400> SEQUENCE: 36

Ala Thr Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 37
<211> LENGTH: 31
<212> TYPE: PRT
<213> ORGANISM: Artificial Sequence
<220> FEATURE:
<223> OTHER INFORMATION: Tamapin F2V

<400> SEQUENCE: 37

Ala Val Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 38
<211> LENGTH: 31
<212> TYPE: PRT
<213> ORGANISM: Artificial Sequence
<220> FEATURE:
<223> OTHER INFORMATION: Tamapin F2W

<400> SEQUENCE: 38

Ala Trp Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 39
<211> LENGTH: 31
<212> TYPE: PRT
<213> ORGANISM: Artificial Sequence
<220> FEATURE:
<223> OTHER INFORMATION: Tamapin F2Y

<400> SEQUENCE: 39

Ala Tyr Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Tamapin C3A

<400> SEQUENCE: 40

Ala Phe Ala Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

```
<210> SEQ ID NO 41
<211> LENGTH: 31
<212> TYPE: PRT
<213> ORGANISM: Artificial Sequence
<220> FEATURE:
<223> OTHER INFORMATION: Tamapin C3D

<400> SEQUENCE: 41

Ala Phe Asp Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 42
<211> LENGTH: 31
<212> TYPE: PRT
<213> ORGANISM: Artificial Sequence
<220> FEATURE:
<223> OTHER INFORMATION: Tamapin C3E

<400> SEQUENCE: 42

Ala Phe Glu Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 43
<211> LENGTH: 31
<212> TYPE: PRT
<213> ORGANISM: Artificial Sequence
<220> FEATURE:
<223> OTHER INFORMATION: Tamapin C3F

<400> SEQUENCE: 43

Ala Phe Phe Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: Tamapin C3G

<400> SEQUENCE: 44

Ala Phe Gly Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: Tamapin C3H

<400> SEQUENCE: 45

Ala Phe His Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

```
<210> SEQ ID NO 46
<211> LENGTH: 31
<212> TYPE: PRT
<213> ORGANISM: Artificial Sequence
<220> FEATURE:
<223> OTHER INFORMATION: Tamapin C3I

<400> SEQUENCE: 46

Ala Phe Ile Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: Tamapin C3K

<400> SEQUENCE: 47

Ala Phe Lys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Tamapin C3L

<400> SEQUENCE: 48

Ala Phe Leu Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Tamapin C3M

<400> SEQUENCE: 49

Ala Phe Met Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: Tamapin analog

<400> SEQUENCE: 50

Ala Phe Pro Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
```

-continued

```
                 20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Tamapin C3P

<400> SEQUENCE: 51

Ala Phe Pro Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Tamapin C3Q

<400> SEQUENCE: 52

Ala Phe Gln Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Tamapin C3R

<400> SEQUENCE: 53

Ala Phe Arg Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Tamapin C3S

<400> SEQUENCE: 54

Ala Phe Ser Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Tamapin C3T

<400> SEQUENCE: 55

Ala Phe Thr Asn Leu Arg Arg Cys Glu Leu Ser Cys Arg Ser Leu Gly
1               5                   10                  15
```

Leu Leu Gly Lys Cys Ile Gly Glu Glu Cys Lys Cys Val Pro Tyr
        20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Tamapin C3V

<400> SEQUENCE: 56

Ala Phe Val Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
        20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Tamapin C3W

<400> SEQUENCE: 57

Ala Phe Trp Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
        20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Tamapin C3Y

<400> SEQUENCE: 58

Ala Phe Tyr Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
        20                  25                  30

<210> SEQ ID NO 59
<211> LENGTH: 31
<212> TYPE: PRT
<213> ORGANISM: Artificial Sequence
<220> FEATURE:
<223> OTHER INFORMATION: Tamapin N4A

<400> SEQUENCE: 59

Ala Phe Cys Ala Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
        20                  25                  30

<210> SEQ ID NO 60
<211> LENGTH: 31
<212> TYPE: PRT
<213> ORGANISM: Artificial Sequence
<220> FEATURE:
<223> OTHER INFORMATION: Tamapin N4C

<400> SEQUENCE: 60

Ala Phe Cys Cys Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: Tamapin N4D

<400> SEQUENCE: 61

Ala Phe Cys Asp Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: Tamapin N4E

<400> SEQUENCE: 62

Ala Phe Cys Glu Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: Tamapin N4F

<400> SEQUENCE: 63

Ala Phe Cys Phe Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Tamapin N4G

<400> SEQUENCE: 64

Ala Phe Cys Gly Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 65
<211> LENGTH: 31
<212> TYPE: PRT
<213> ORGANISM: Artificial Sequence
<220> FEATURE:
<223> OTHER INFORMATION: Tamapin N4H

<400> SEQUENCE: 65

Ala Phe Cys His Leu Arg Arg Cys Glu Leu Ser Cys Arg Ser Leu Gly

```
                1               5                   10                  15
Leu Leu Gly Lys Cys Ile Gly Glu Glu Cys Lys Cys Val Pro Tyr
                20                  25                  30
```

<210> SEQ ID NO 66
<211> LENGTH: 31
<212> TYPE: PRT
<213> ORGANISM: Artificial Sequence
<220> FEATURE:
<223> OTHER INFORMATION: Tamapin N4I

<400> SEQUENCE: 66

```
Ala Phe Cys Ile Leu Arg Arg Cys Glu Leu Ser Cys Arg Ser Leu Gly
1               5                   10                  15
Leu Leu Gly Lys Cys Ile Gly Glu Glu Cys Lys Cys Val Pro Tyr
                20                  25                  30
```

<210> SEQ ID NO 67
<211> LENGTH: 31
<212> TYPE: PRT
<213> ORGANISM: Artificial Sequence
<220> FEATURE:
<223> OTHER INFORMATION: Tamapin N4K

<400> SEQUENCE: 67

```
Ala Phe Cys Lys Leu Arg Arg Cys Glu Leu Ser Cys Arg Ser Leu Gly
1               5                   10                  15
Leu Leu Gly Lys Cys Ile Gly Glu Glu Cys Lys Cys Val Pro Tyr
                20                  25                  30
```

<210> SEQ ID NO 68
<211> LENGTH: 31
<212> TYPE: PRT
<213> ORGANISM: Artificial Sequence
<220> FEATURE:
<223> OTHER INFORMATION: Tamapin N4L

<400> SEQUENCE: 68

```
Ala Phe Cys Leu Leu Arg Arg Cys Glu Leu Ser Cys Arg Ser Leu Gly
1               5                   10                  15
Leu Leu Gly Lys Cys Ile Gly Glu Glu Cys Lys Cys Val Pro Tyr
                20                  25                  30
```

<210> SEQ ID NO 69
<211> LENGTH: 31
<212> TYPE: PRT
<213> ORGANISM: Artificial Sequence
<220> FEATURE:
<223> OTHER INFORMATION: Tamapin N4M

<400> SEQUENCE: 69

```
Ala Phe Cys Met Leu Arg Arg Cys Glu Leu Ser Cys Arg Ser Leu Gly
1               5                   10                  15
Leu Leu Gly Lys Cys Ile Gly Glu Glu Cys Lys Cys Val Pro Tyr
                20                  25                  30
```

<210> SEQ ID NO 70
<211> LENGTH: 31
<212> TYPE: PRT
<213> ORGANISM: Artificial Sequence
<220> FEATURE:
<223> OTHER INFORMATION: Tamapin N4P

<400> SEQUENCE: 70

```
Ala Phe Cys Pro Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 71
<211> LENGTH: 31
<212> TYPE: PRT
<213> ORGANISM: Artificial Sequence
<220> FEATURE:
<223> OTHER INFORMATION: Tamapin N4Q

<400> SEQUENCE: 71

Ala Phe Cys Gln Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 72
<211> LENGTH: 31
<212> TYPE: PRT
<213> ORGANISM: Artificial Sequence
<220> FEATURE:
<223> OTHER INFORMATION: Tamapin N4R

<400> SEQUENCE: 72

Ala Phe Cys Arg Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 73
<211> LENGTH: 31
<212> TYPE: PRT
<213> ORGANISM: Artificial Sequence
<220> FEATURE:
<223> OTHER INFORMATION: Tamapin N4S

<400> SEQUENCE: 73

Ala Phe Cys Ser Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 74
<211> LENGTH: 31
<212> TYPE: PRT
<213> ORGANISM: Artificial Sequence
<220> FEATURE:
<223> OTHER INFORMATION: Tamapin N4T

<400> SEQUENCE: 74

Ala Phe Cys Thr Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 75
<211> LENGTH: 31
<212> TYPE: PRT
<213> ORGANISM: Artificial Sequence
<220> FEATURE:
<223> OTHER INFORMATION: Tamapin N4V

<400> SEQUENCE: 75
```

```
Ala Phe Cys Val Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 76
<211> LENGTH: 31
<212> TYPE: PRT
<213> ORGANISM: Artificial Sequence
<220> FEATURE:
<223> OTHER INFORMATION: Tamapin N4W

<400> SEQUENCE: 76

```
Ala Phe Cys Trp Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 77
<211> LENGTH: 31
<212> TYPE: PRT
<213> ORGANISM: Artificial Sequence
<220> FEATURE:
<223> OTHER INFORMATION: Tamapin N4Y

<400> SEQUENCE: 77

```
Ala Phe Cys Tyr Leu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 78
<211> LENGTH: 31
<212> TYPE: PRT
<213> ORGANISM: Artificial Sequence
<220> FEATURE:
<223> OTHER INFORMATION: Tamapin L5A

<400> SEQUENCE: 78

```
Ala Phe Cys Asn Ala Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 79
<211> LENGTH: 31
<212> TYPE: PRT
<213> ORGANISM: Artificial Sequence
<220> FEATURE:
<223> OTHER INFORMATION: Tamapin L5C

<400> SEQUENCE: 79

```
Ala Phe Cys Asn Cys Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 80
<211> LENGTH: 31
<212> TYPE: PRT
<213> ORGANISM: Artificial Sequence
<220> FEATURE:
<223> OTHER INFORMATION: Tamapin L5D

```
<400> SEQUENCE: 80

Ala Phe Cys Asn Asp Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 81
<211> LENGTH: 31
<212> TYPE: PRT
<213> ORGANISM: Artificial Sequence
<220> FEATURE:
<223> OTHER INFORMATION: Tamapin L5E

<400> SEQUENCE: 81

Ala Phe Cys Asn Glu Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 82
<211> LENGTH: 31
<212> TYPE: PRT
<213> ORGANISM: Artificial Sequence
<220> FEATURE:
<223> OTHER INFORMATION: Tamapin L5F

<400> SEQUENCE: 82

Ala Phe Cys Asn Phe Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Tamapin L5G

<400> SEQUENCE: 83

Ala Phe Cys Asn Gly Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 84
<211> LENGTH: 31
<212> TYPE: PRT
<213> ORGANISM: Artificial Sequence
<220> FEATURE:
<223> OTHER INFORMATION: Tamapin L5H

<400> SEQUENCE: 84

Ala Phe Cys Asn His Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 85
<211> LENGTH: 31
<212> TYPE: PRT
<213> ORGANISM: Artificial Sequence
<220> FEATURE:
<223> OTHER INFORMATION: Tamapin L5I
```

<400> SEQUENCE: 85

Ala Phe Cys Asn Ile Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Tamapin L5K

<400> SEQUENCE: 86

Ala Phe Cys Asn Lys Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 87
<211> LENGTH: 31
<212> TYPE: PRT
<213> ORGANISM: Artificial Sequence
<220> FEATURE:
<223> OTHER INFORMATION: Tamapin L5M

<400> SEQUENCE: 87

Ala Phe Cys Asn Met Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 88
<211> LENGTH: 31
<212> TYPE: PRT
<213> ORGANISM: Artificial Sequence
<220> FEATURE:
<223> OTHER INFORMATION: Tamapin L5N

<400> SEQUENCE: 88

Ala Phe Cys Asn Asn Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Tamapin L5P

<400> SEQUENCE: 89

Ala Phe Cys Asn Pro Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 90
<211> LENGTH: 31
<212> TYPE: PRT
<213> ORGANISM: Artificial Sequence
<220> FEATURE:

<223> OTHER INFORMATION: Tamapin L5Q

<400> SEQUENCE: 90

Ala Phe Cys Asn Gln Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 91
<211> LENGTH: 31
<212> TYPE: PRT
<213> ORGANISM: Artificial Sequence
<220> FEATURE:
<223> OTHER INFORMATION: Tamapin L5R

<400> SEQUENCE: 91

Ala Phe Cys Asn Arg Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Tamapin L5S

<400> SEQUENCE: 92

Ala Phe Cys Asn Ser Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Tamapin L5T

<400> SEQUENCE: 93

Ala Phe Cys Asn Thr Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 94
<211> LENGTH: 31
<212> TYPE: PRT
<213> ORGANISM: Artificial Sequence
<220> FEATURE:
<223> OTHER INFORMATION: Tamapin L5V

<400> SEQUENCE: 94

Ala Phe Cys Asn Val Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 95
<211> LENGTH: 31
<212> TYPE: PRT
<213> ORGANISM: Artificial Sequence

```
<220> FEATURE:
<223> OTHER INFORMATION: Tamapin L5W

<400> SEQUENCE: 95

Ala Phe Cys Asn Trp Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Tamapin L5Y

<400> SEQUENCE: 96

Ala Phe Cys Asn Tyr Arg Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: Tamapin R6A

<400> SEQUENCE: 97

Ala Phe Cys Asn Leu Ala Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: Tamapin R6C

<400> SEQUENCE: 98

Ala Phe Cys Asn Leu Cys Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Tamapin R6D

<400> SEQUENCE: 99

Ala Phe Cys Asn Leu Asp Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 100
<211> LENGTH: 31
<212> TYPE: PRT
```

```
<213> ORGANISM: Artificial Sequence
<220> FEATURE:
<223> OTHER INFORMATION: Tamapin R6E

<400> SEQUENCE: 100

Ala Phe Cys Asn Leu Glu Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 101
<211> LENGTH: 31
<212> TYPE: PRT
<213> ORGANISM: Artificial Sequence
<220> FEATURE:
<223> OTHER INFORMATION: Tamapin R6F

<400> SEQUENCE: 101

Ala Phe Cys Asn Leu Phe Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 102
<211> LENGTH: 31
<212> TYPE: PRT
<213> ORGANISM: Artificial Sequence
<220> FEATURE:
<223> OTHER INFORMATION: Tamapin R6G

<400> SEQUENCE: 102

Ala Phe Cys Asn Leu Gly Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 103
<211> LENGTH: 31
<212> TYPE: PRT
<213> ORGANISM: Artificial Sequence
<220> FEATURE:
<223> OTHER INFORMATION: Tamapin R6H

<400> SEQUENCE: 103

Ala Phe Cys Asn Leu His Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 104
<211> LENGTH: 31
<212> TYPE: PRT
<213> ORGANISM: Artificial Sequence
<220> FEATURE:
<223> OTHER INFORMATION: Tamapin R6I

<400> SEQUENCE: 104

Ala Phe Cys Asn Leu Ile Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 105
<211> LENGTH: 31
```

```
<212> TYPE: PRT
<213> ORGANISM: Artificial Sequence
<220> FEATURE:
<223> OTHER INFORMATION: Tamapin R6K

<400> SEQUENCE: 105

Ala Phe Cys Asn Leu Lys Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 106
<211> LENGTH: 31
<212> TYPE: PRT
<213> ORGANISM: Artificial Sequence
<220> FEATURE:
<223> OTHER INFORMATION: Tamapin R6L

<400> SEQUENCE: 106

Ala Phe Cys Asn Leu Leu Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 107
<211> LENGTH: 31
<212> TYPE: PRT
<213> ORGANISM: Artificial Sequence
<220> FEATURE:
<223> OTHER INFORMATION: Tamapin R6M

<400> SEQUENCE: 107

Ala Phe Cys Asn Leu Met Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 108
<211> LENGTH: 31
<212> TYPE: PRT
<213> ORGANISM: Artificial Sequence
<220> FEATURE:
<223> OTHER INFORMATION: Tamapin R6N

<400> SEQUENCE: 108

Ala Phe Cys Asn Leu Asn Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 109
<211> LENGTH: 31
<212> TYPE: PRT
<213> ORGANISM: Artificial Sequence
<220> FEATURE:
<223> OTHER INFORMATION: Tamapin R6P

<400> SEQUENCE: 109

Ala Phe Cys Asn Leu Pro Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 110
```

-continued

```
<211> LENGTH: 31
<212> TYPE: PRT
<213> ORGANISM: Artificial Sequence
<220> FEATURE:
<223> OTHER INFORMATION: Tamapin R6Q

<400> SEQUENCE: 110

Ala Phe Cys Asn Leu Gln Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: Tamapin R6S

<400> SEQUENCE: 111

Ala Phe Cys Asn Leu Ser Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 112
<211> LENGTH: 31
<212> TYPE: PRT
<213> ORGANISM: Artificial Sequence
<220> FEATURE:
<223> OTHER INFORMATION: Tamapin R6T

<400> SEQUENCE: 112

Ala Phe Cys Asn Leu Thr Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 113
<211> LENGTH: 31
<212> TYPE: PRT
<213> ORGANISM: Artificial Sequence
<220> FEATURE:
<223> OTHER INFORMATION: Tamapin R6V

<400> SEQUENCE: 113

Ala Phe Cys Asn Leu Val Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 114
<211> LENGTH: 31
<212> TYPE: PRT
<213> ORGANISM: Artificial Sequence
<220> FEATURE:
<223> OTHER INFORMATION: Tamapin R6W

<400> SEQUENCE: 114

Ala Phe Cys Asn Leu Trp Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

```
<210> SEQ ID NO 115
<211> LENGTH: 31
<212> TYPE: PRT
<213> ORGANISM: Artificial Sequence
<220> FEATURE:
<223> OTHER INFORMATION: Tamapin R6Y

<400> SEQUENCE: 115

Ala Phe Cys Asn Leu Tyr Arg Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 116
<211> LENGTH: 31
<212> TYPE: PRT
<213> ORGANISM: Artificial Sequence
<220> FEATURE:
<223> OTHER INFORMATION: Tamapin R7A

<400> SEQUENCE: 116

Ala Phe Cys Asn Leu Arg Ala Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 117
<211> LENGTH: 31
<212> TYPE: PRT
<213> ORGANISM: Artificial Sequence
<220> FEATURE:
<223> OTHER INFORMATION: Tamapin R7C

<400> SEQUENCE: 117

Ala Phe Cys Asn Leu Arg Cys Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 118
<211> LENGTH: 31
<212> TYPE: PRT
<213> ORGANISM: Artificial Sequence
<220> FEATURE:
<223> OTHER INFORMATION: Tamapin R7D

<400> SEQUENCE: 118

Ala Phe Cys Asn Leu Arg Asp Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 119
<211> LENGTH: 31
<212> TYPE: PRT
<213> ORGANISM: Artificial Sequence
<220> FEATURE:
<223> OTHER INFORMATION: Tamapin R7E

<400> SEQUENCE: 119

Ala Phe Cys Asn Leu Arg Glu Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 120
<211> LENGTH: 31
<212> TYPE: PRT
<213> ORGANISM: Artificial Sequence
<220> FEATURE:
<223> OTHER INFORMATION: Tamapin R7F

<400> SEQUENCE: 120

Ala Phe Cys Asn Leu Arg Phe Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 121
<211> LENGTH: 31
<212> TYPE: PRT
<213> ORGANISM: Artificial Sequence
<220> FEATURE:
<223> OTHER INFORMATION: Tamapin R7G

<400> SEQUENCE: 121

Ala Phe Cys Asn Leu Arg Gly Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 122
<211> LENGTH: 31
<212> TYPE: PRT
<213> ORGANISM: Artificial Sequence
<220> FEATURE:
<223> OTHER INFORMATION: Tamapin R7H

<400> SEQUENCE: 122

Ala Phe Cys Asn Leu Arg His Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 123
<211> LENGTH: 31
<212> TYPE: PRT
<213> ORGANISM: Artificial Sequence
<220> FEATURE:
<223> OTHER INFORMATION: Tamapin R7I

<400> SEQUENCE: 123

Ala Phe Cys Asn Leu Arg Ile Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 124
<211> LENGTH: 31
<212> TYPE: PRT
<213> ORGANISM: Artificial Sequence
<220> FEATURE:
<223> OTHER INFORMATION: Tamapin R7K

<400> SEQUENCE: 124

Ala Phe Cys Asn Leu Arg Lys Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 125
<211> LENGTH: 31
<212> TYPE: PRT
<213> ORGANISM: Artificial Sequence
<220> FEATURE:
<223> OTHER INFORMATION: Tamapin R7L

<400> SEQUENCE: 125

Ala Phe Cys Asn Leu Arg Leu Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 126
<211> LENGTH: 31
<212> TYPE: PRT
<213> ORGANISM: Artificial Sequence
<220> FEATURE:
<223> OTHER INFORMATION: Tamapin R7M

<400> SEQUENCE: 126

Ala Phe Cys Asn Leu Arg Met Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 127
<211> LENGTH: 31
<212> TYPE: PRT
<213> ORGANISM: Artificial Sequence
<220> FEATURE:
<223> OTHER INFORMATION: Tamapin R7N

<400> SEQUENCE: 127

Ala Phe Cys Asn Leu Arg Asn Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 128
<211> LENGTH: 31
<212> TYPE: PRT
<213> ORGANISM: Artificial Sequence
<220> FEATURE:
<223> OTHER INFORMATION: Tamapin R7P

<400> SEQUENCE: 128

Ala Phe Cys Asn Leu Arg Pro Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 129
<211> LENGTH: 31
<212> TYPE: PRT
<213> ORGANISM: Artificial Sequence
<220> FEATURE:
<223> OTHER INFORMATION: Tamapin R7Q

<400> SEQUENCE: 129

Ala Phe Cys Asn Leu Arg Gln Cys Glu Leu Ser Cys Arg Ser Leu Gly
1               5                   10                  15

Leu Leu Gly Lys Cys Ile Gly Glu Glu Cys Lys Cys Val Pro Tyr

-continued

```
                20                  25                  30
```

<210> SEQ ID NO 130
<211> LENGTH: 31
<212> TYPE: PRT
<213> ORGANISM: Artificial Sequence
<220> FEATURE:
<223> OTHER INFORMATION: Tamapin R7S

<400> SEQUENCE: 130

```
Ala Phe Cys Asn Leu Arg Ser Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 131
<211> LENGTH: 31
<212> TYPE: PRT
<213> ORGANISM: Artificial Sequence
<220> FEATURE:
<223> OTHER INFORMATION: Tamapin R7T

<400> SEQUENCE: 131

```
Ala Phe Cys Asn Leu Arg Thr Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 132
<211> LENGTH: 31
<212> TYPE: PRT
<213> ORGANISM: Artificial Sequence
<220> FEATURE:
<223> OTHER INFORMATION: Tamapin R7V

<400> SEQUENCE: 132

```
Ala Phe Cys Asn Leu Arg Val Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 133
<211> LENGTH: 31
<212> TYPE: PRT
<213> ORGANISM: Artificial Sequence
<220> FEATURE:
<223> OTHER INFORMATION: Tamapin R7W

<400> SEQUENCE: 133

```
Ala Phe Cys Asn Leu Arg Trp Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 134
<211> LENGTH: 31
<212> TYPE: PRT
<213> ORGANISM: Artificial Sequence
<220> FEATURE:
<223> OTHER INFORMATION: Tamapin R7Y

<400> SEQUENCE: 134

```
Ala Phe Cys Asn Leu Arg Tyr Cys Glu Leu Ser Cys Arg Ser Leu Gly
1               5                   10                  15
```

Leu Leu Gly Lys Cys Ile Gly Glu Glu Cys Lys Cys Val Pro Tyr
            20                  25                  30

<210> SEQ ID NO 135
<211> LENGTH: 31
<212> TYPE: PRT
<213> ORGANISM: Artificial Sequence
<220> FEATURE:
<223> OTHER INFORMATION: Tamapin C8A

<400> SEQUENCE: 135

Ala Phe Cys Asn Leu Arg Arg Ala Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 136
<211> LENGTH: 31
<212> TYPE: PRT
<213> ORGANISM: Artificial Sequence
<220> FEATURE:
<223> OTHER INFORMATION: Tamapin C8D

<400> SEQUENCE: 136

Ala Phe Cys Asn Leu Arg Arg Asp Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 137
<211> LENGTH: 31
<212> TYPE: PRT
<213> ORGANISM: Artificial Sequence
<220> FEATURE:
<223> OTHER INFORMATION: Tamapin C8E

<400> SEQUENCE: 137

Ala Phe Cys Asn Leu Arg Arg Glu Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Tamapin C8F

<400> SEQUENCE: 138

Ala Phe Cys Asn Leu Arg Arg Phe Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Tamapin C8G

<400> SEQUENCE: 139

Ala Phe Cys Asn Leu Arg Arg Gly Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 140
<211> LENGTH: 31
<212> TYPE: PRT
<213> ORGANISM: Artificial Sequence
<220> FEATURE:
<223> OTHER INFORMATION: Tamapin C8H

<400> SEQUENCE: 140

Ala Phe Cys Asn Leu Arg Arg His Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 141
<211> LENGTH: 31
<212> TYPE: PRT
<213> ORGANISM: Artificial Sequence
<220> FEATURE:
<223> OTHER INFORMATION: Tamapin C8I

<400> SEQUENCE: 141

Ala Phe Cys Asn Leu Arg Arg Ile Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 142
<211> LENGTH: 31
<212> TYPE: PRT
<213> ORGANISM: Artificial Sequence
<220> FEATURE:
<223> OTHER INFORMATION: Tamapin C8K

<400> SEQUENCE: 142

Ala Phe Cys Asn Leu Arg Arg Lys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 143
<211> LENGTH: 31
<212> TYPE: PRT
<213> ORGANISM: Artificial Sequence
<220> FEATURE:
<223> OTHER INFORMATION: Tamapin C8L

<400> SEQUENCE: 143

Ala Phe Cys Asn Leu Arg Arg Leu Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 144
<211> LENGTH: 31
<212> TYPE: PRT
<213> ORGANISM: Artificial Sequence
<220> FEATURE:
<223> OTHER INFORMATION: Tamapin C8M

<400> SEQUENCE: 144

Ala Phe Cys Asn Leu Arg Arg Met Glu Leu Ser Cys Arg Ser Leu Gly

```
                1               5                  10                  15
Leu Leu Gly Lys Cys Ile Gly Glu Glu Cys Lys Cys Val Pro Tyr
                20                  25                  30

<210> SEQ ID NO 145
<211> LENGTH: 31
<212> TYPE: PRT
<213> ORGANISM: Artificial Sequence
<220> FEATURE:
<223> OTHER INFORMATION: Tamapin C8N

<400> SEQUENCE: 145

Ala Phe Cys Asn Leu Arg Arg Asn Glu Leu Ser Cys Arg Ser Leu Gly
1               5                  10                  15

Leu Leu Gly Lys Cys Ile Gly Glu Glu Cys Lys Cys Val Pro Tyr
                20                  25                  30

<210> SEQ ID NO 146
<211> LENGTH: 31
<212> TYPE: PRT
<213> ORGANISM: Artificial Sequence
<220> FEATURE:
<223> OTHER INFORMATION: Tamapin C8P

<400> SEQUENCE: 146

Ala Phe Cys Asn Leu Arg Arg Pro Glu Leu Ser Cys Arg Ser Leu Gly
1               5                  10                  15

Leu Leu Gly Lys Cys Ile Gly Glu Glu Cys Lys Cys Val Pro Tyr
                20                  25                  30

<210> SEQ ID NO 147
<211> LENGTH: 31
<212> TYPE: PRT
<213> ORGANISM: Artificial Sequence
<220> FEATURE:
<223> OTHER INFORMATION: Tamapin C8Q

<400> SEQUENCE: 147

Ala Phe Cys Asn Leu Arg Arg Gln Glu Leu Ser Cys Arg Ser Leu Gly
1               5                  10                  15

Leu Leu Gly Lys Cys Ile Gly Glu Glu Cys Lys Cys Val Pro Tyr
                20                  25                  30

<210> SEQ ID NO 148
<211> LENGTH: 31
<212> TYPE: PRT
<213> ORGANISM: Artificial Sequence
<220> FEATURE:
<223> OTHER INFORMATION: Tamapin C8R

<400> SEQUENCE: 148

Ala Phe Cys Asn Leu Arg Arg Arg Glu Leu Ser Cys Arg Ser Leu Gly
1               5                  10                  15

Leu Leu Gly Lys Cys Ile Gly Glu Glu Cys Lys Cys Val Pro Tyr
                20                  25                  30

<210> SEQ ID NO 149
<211> LENGTH: 31
<212> TYPE: PRT
<213> ORGANISM: Artificial Sequence
<220> FEATURE:
<223> OTHER INFORMATION: Tamapin C8S

<400> SEQUENCE: 149
```

Ala Phe Cys Asn Leu Arg Arg Ser Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 150
<211> LENGTH: 31
<212> TYPE: PRT
<213> ORGANISM: Artificial Sequence
<220> FEATURE:
<223> OTHER INFORMATION: Tamapin C8T

<400> SEQUENCE: 150

Ala Phe Cys Asn Leu Arg Arg Thr Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 151
<211> LENGTH: 31
<212> TYPE: PRT
<213> ORGANISM: Artificial Sequence
<220> FEATURE:
<223> OTHER INFORMATION: Tamapin C8V

<400> SEQUENCE: 151

Ala Phe Cys Asn Leu Arg Arg Val Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 152
<211> LENGTH: 31
<212> TYPE: PRT
<213> ORGANISM: Artificial Sequence
<220> FEATURE:
<223> OTHER INFORMATION: Tamapin C8W

<400> SEQUENCE: 152

Ala Phe Cys Asn Leu Arg Leu Cys Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 153
<211> LENGTH: 31
<212> TYPE: PRT
<213> ORGANISM: Artificial Sequence
<220> FEATURE:
<223> OTHER INFORMATION: Tamapin C8Y

<400> SEQUENCE: 153

Ala Phe Cys Asn Leu Arg Arg Tyr Glu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 154
<211> LENGTH: 31
<212> TYPE: PRT
<213> ORGANISM: Artificial Sequence
<220> FEATURE:
<223> OTHER INFORMATION: Tamapin E9A

<400> SEQUENCE: 154

Ala Phe Cys Asn Leu Arg Arg Cys Ala Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 155
<211> LENGTH: 31
<212> TYPE: PRT
<213> ORGANISM: Artificial Sequence
<220> FEATURE:
<223> OTHER INFORMATION: Tamapin E9C

<400> SEQUENCE: 155

Ala Phe Cys Asn Leu Arg Arg Cys Cys Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 156
<211> LENGTH: 31
<212> TYPE: PRT
<213> ORGANISM: Artificial Sequence
<220> FEATURE:
<223> OTHER INFORMATION: Tamapin E9D

<400> SEQUENCE: 156

Ala Phe Cys Asn Leu Arg Arg Cys Asp Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 157
<211> LENGTH: 31
<212> TYPE: PRT
<213> ORGANISM: Artificial Sequence
<220> FEATURE:
<223> OTHER INFORMATION: Tamapin E9F

<400> SEQUENCE: 157

Ala Phe Cys Asn Leu Arg Arg Cys Phe Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 158
<211> LENGTH: 31
<212> TYPE: PRT
<213> ORGANISM: Artificial Sequence
<220> FEATURE:
<223> OTHER INFORMATION: Tamapin E9G

<400> SEQUENCE: 158

Ala Phe Cys Asn Leu Arg Arg Cys Gly Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 159
<211> LENGTH: 31
<212> TYPE: PRT
<213> ORGANISM: Artificial Sequence
<220> FEATURE:
<223> OTHER INFORMATION: Tamapin E9H

```
<400> SEQUENCE: 159

Ala Phe Cys Asn Leu Arg Arg Cys His Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 160
<211> LENGTH: 31
<212> TYPE: PRT
<213> ORGANISM: Artificial Sequence
<220> FEATURE:
<223> OTHER INFORMATION: Tamapin E9I

<400> SEQUENCE: 160

Ala Phe Cys Asn Leu Arg Arg Cys Ile Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 161
<211> LENGTH: 31
<212> TYPE: PRT
<213> ORGANISM: Artificial Sequence
<220> FEATURE:
<223> OTHER INFORMATION: Tamapin E9K

<400> SEQUENCE: 161

Ala Phe Cys Asn Leu Arg Arg Cys Lys Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 162
<211> LENGTH: 31
<212> TYPE: PRT
<213> ORGANISM: Artificial Sequence
<220> FEATURE:
<223> OTHER INFORMATION: Tamapin E9L

<400> SEQUENCE: 162

Ala Phe Cys Asn Leu Arg Arg Cys Leu Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 163
<211> LENGTH: 31
<212> TYPE: PRT
<213> ORGANISM: Artificial Sequence
<220> FEATURE:
<223> OTHER INFORMATION: Tamapin E9M

<400> SEQUENCE: 163

Ala Phe Cys Asn Leu Arg Arg Cys Met Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 164
<211> LENGTH: 31
<212> TYPE: PRT
<213> ORGANISM: Artificial Sequence
<220> FEATURE:
<223> OTHER INFORMATION: Tamapin E9N
```

```
<400> SEQUENCE: 164

Ala Phe Cys Asn Leu Arg Arg Cys Asn Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 165
<211> LENGTH: 31
<212> TYPE: PRT
<213> ORGANISM: Artificial Sequence
<220> FEATURE:
<223> OTHER INFORMATION: Tamapin E9P

<400> SEQUENCE: 165

Ala Phe Cys Asn Leu Arg Arg Cys Pro Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 166
<211> LENGTH: 31
<212> TYPE: PRT
<213> ORGANISM: Artificial Sequence
<220> FEATURE:
<223> OTHER INFORMATION: Tamapin E9Q

<400> SEQUENCE: 166

Ala Phe Cys Asn Leu Arg Arg Cys Gln Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 167
<211> LENGTH: 31
<212> TYPE: PRT
<213> ORGANISM: Artificial Sequence
<220> FEATURE:
<223> OTHER INFORMATION: Tamapin E9R

<400> SEQUENCE: 167

Ala Phe Cys Asn Leu Arg Arg Cys Arg Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 168
<211> LENGTH: 31
<212> TYPE: PRT
<213> ORGANISM: Artificial Sequence
<220> FEATURE:
<223> OTHER INFORMATION: Tamapin E9S

<400> SEQUENCE: 168

Ala Phe Cys Asn Leu Arg Arg Cys Ser Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 169
<211> LENGTH: 31
<212> TYPE: PRT
<213> ORGANISM: Artificial Sequence
<220> FEATURE:
```

<223> OTHER INFORMATION: Tamapin E9T

<400> SEQUENCE: 169

Ala Phe Cys Asn Leu Arg Arg Cys Thr Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 170
<211> LENGTH: 31
<212> TYPE: PRT
<213> ORGANISM: Artificial Sequence
<220> FEATURE:
<223> OTHER INFORMATION: Tamapin E9V

<400> SEQUENCE: 170

Ala Phe Cys Asn Leu Arg Arg Cys Val Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 171
<211> LENGTH: 31
<212> TYPE: PRT
<213> ORGANISM: Artificial Sequence
<220> FEATURE:
<223> OTHER INFORMATION: Tamapin E9W

<400> SEQUENCE: 171

Ala Phe Cys Asn Leu Arg Arg Cys Trp Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 172
<211> LENGTH: 31
<212> TYPE: PRT
<213> ORGANISM: Artificial Sequence
<220> FEATURE:
<223> OTHER INFORMATION: Tamapin E9Y

<400> SEQUENCE: 172

Ala Phe Cys Asn Leu Arg Arg Cys Tyr Leu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 173
<211> LENGTH: 31
<212> TYPE: PRT
<213> ORGANISM: Artificial Sequence
<220> FEATURE:
<223> OTHER INFORMATION: Tamapin L10A

<400> SEQUENCE: 173

Ala Phe Cys Asn Leu Arg Arg Cys Glu Ala Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 174
<211> LENGTH: 31
<212> TYPE: PRT
<213> ORGANISM: Artificial Sequence

```
<220> FEATURE:
<223> OTHER INFORMATION: Tamapin L10C

<400> SEQUENCE: 174

Ala Phe Cys Asn Leu Arg Arg Cys Glu Cys Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 175
<211> LENGTH: 31
<212> TYPE: PRT
<213> ORGANISM: Artificial Sequence
<220> FEATURE:
<223> OTHER INFORMATION: Tamapin L10D

<400> SEQUENCE: 175

Ala Phe Cys Asn Leu Arg Arg Cys Glu Asp Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 176
<211> LENGTH: 31
<212> TYPE: PRT
<213> ORGANISM: Artificial Sequence
<220> FEATURE:
<223> OTHER INFORMATION: Tamapin L10E

<400> SEQUENCE: 176

Ala Phe Cys Asn Leu Arg Arg Cys Glu Glu Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 177
<211> LENGTH: 31
<212> TYPE: PRT
<213> ORGANISM: Artificial Sequence
<220> FEATURE:
<223> OTHER INFORMATION: Tamapin L10F

<400> SEQUENCE: 177

Ala Phe Cys Asn Leu Arg Arg Cys Glu Phe Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 178
<211> LENGTH: 31
<212> TYPE: PRT
<213> ORGANISM: Artificial Sequence
<220> FEATURE:
<223> OTHER INFORMATION: Tamapin L10G

<400> SEQUENCE: 178

Ala Phe Cys Asn Leu Arg Arg Cys Glu Gly Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 179
<211> LENGTH: 31
<212> TYPE: PRT
```

<213> ORGANISM: Artificial Sequence
<220> FEATURE:
<223> OTHER INFORMATION: Tamapin L10H

<400> SEQUENCE: 179

Ala Phe Cys Asn Leu Arg Arg Cys Glu His Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 180
<211> LENGTH: 31
<212> TYPE: PRT
<213> ORGANISM: Artificial Sequence
<220> FEATURE:
<223> OTHER INFORMATION: Tamapin L10I

<400> SEQUENCE: 180

Ala Phe Cys Asn Leu Arg Arg Cys Glu Ile Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 181
<211> LENGTH: 31
<212> TYPE: PRT
<213> ORGANISM: Artificial Sequence
<220> FEATURE:
<223> OTHER INFORMATION: Tamapin L10K

<400> SEQUENCE: 181

Ala Phe Cys Asn Leu Arg Arg Cys Glu Lys Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 182
<211> LENGTH: 31
<212> TYPE: PRT
<213> ORGANISM: Artificial Sequence
<220> FEATURE:
<223> OTHER INFORMATION: Tamapin L10M

<400> SEQUENCE: 182

Ala Phe Cys Asn Leu Arg Arg Cys Glu Met Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 183
<211> LENGTH: 31
<212> TYPE: PRT
<213> ORGANISM: Artificial Sequence
<220> FEATURE:
<223> OTHER INFORMATION: Tamapin L10N

<400> SEQUENCE: 183

Ala Phe Cys Asn Leu Arg Arg Cys Glu Asn Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 184
<211> LENGTH: 31

```
<212> TYPE: PRT
<213> ORGANISM: Artificial Sequence
<220> FEATURE:
<223> OTHER INFORMATION: Tamapin L10P

<400> SEQUENCE: 184

Ala Phe Cys Asn Leu Arg Arg Cys Glu Pro Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 185
<211> LENGTH: 31
<212> TYPE: PRT
<213> ORGANISM: Artificial Sequence
<220> FEATURE:
<223> OTHER INFORMATION: Tamapin L10Q

<400> SEQUENCE: 185

Ala Phe Cys Asn Leu Arg Arg Cys Glu Gln Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 186
<211> LENGTH: 31
<212> TYPE: PRT
<213> ORGANISM: Artificial Sequence
<220> FEATURE:
<223> OTHER INFORMATION: Tamapin L10R

<400> SEQUENCE: 186

Ala Phe Cys Asn Leu Arg Arg Cys Glu Arg Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 187
<211> LENGTH: 31
<212> TYPE: PRT
<213> ORGANISM: Artificial Sequence
<220> FEATURE:
<223> OTHER INFORMATION: Tamapin L10S

<400> SEQUENCE: 187

Ala Phe Cys Asn Leu Arg Arg Cys Glu Ser Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 188
<211> LENGTH: 31
<212> TYPE: PRT
<213> ORGANISM: Artificial Sequence
<220> FEATURE:
<223> OTHER INFORMATION: Tamapin L10T

<400> SEQUENCE: 188

Ala Phe Cys Asn Leu Arg Arg Cys Glu Thr Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 189
```

-continued

```
<211> LENGTH: 31
<212> TYPE: PRT
<213> ORGANISM: Artificial Sequence
<220> FEATURE:
<223> OTHER INFORMATION: Tamapin L10V

<400> SEQUENCE: 189

Ala Phe Cys Asn Leu Arg Arg Cys Glu Val Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 190
<211> LENGTH: 31
<212> TYPE: PRT
<213> ORGANISM: Artificial Sequence
<220> FEATURE:
<223> OTHER INFORMATION: Tamapin L10W

<400> SEQUENCE: 190

Ala Phe Cys Asn Leu Arg Arg Cys Glu Trp Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 191
<211> LENGTH: 31
<212> TYPE: PRT
<213> ORGANISM: Artificial Sequence
<220> FEATURE:
<223> OTHER INFORMATION: Tamapin L10Y

<400> SEQUENCE: 191

Ala Phe Cys Asn Leu Arg Arg Cys Glu Tyr Ser Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 192
<211> LENGTH: 31
<212> TYPE: PRT
<213> ORGANISM: Artificial Sequence
<220> FEATURE:
<223> OTHER INFORMATION: Tamapin S11A

<400> SEQUENCE: 192

Ala Phe Cys Asn Leu Arg Arg Cys Glu Leu Ala Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 193
<211> LENGTH: 31
<212> TYPE: PRT
<213> ORGANISM: Artificial Sequence
<220> FEATURE:
<223> OTHER INFORMATION: Tamapin S11C

<400> SEQUENCE: 193

Ala Phe Cys Asn Leu Arg Arg Cys Glu Leu Cys Cys Arg Ser Leu Gly
1               5                   10                  15

Leu Leu Gly Lys Cys Ile Gly Glu Glu Cys Lys Cys Val Pro Tyr
            20                  25                  30
```

```
<210> SEQ ID NO 194
<211> LENGTH: 31
<212> TYPE: PRT
<213> ORGANISM: Artificial Sequence
<220> FEATURE:
<223> OTHER INFORMATION: Tamapin S11D

<400> SEQUENCE: 194

Ala Phe Cys Asn Leu Arg Arg Cys Glu Leu Asp Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 195
<211> LENGTH: 31
<212> TYPE: PRT
<213> ORGANISM: Artificial Sequence
<220> FEATURE:
<223> OTHER INFORMATION: Tamapin S11E

<400> SEQUENCE: 195

Ala Phe Cys Asn Leu Arg Arg Cys Glu Leu Glu Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 196
<211> LENGTH: 31
<212> TYPE: PRT
<213> ORGANISM: Artificial Sequence
<220> FEATURE:
<223> OTHER INFORMATION: Tamapin S11F

<400> SEQUENCE: 196

Ala Phe Cys Asn Leu Arg Arg Cys Glu Leu Phe Cys Arg Ser Leu Gly
1               5                   10                  15

Leu Leu Gly Lys Cys Ile Gly Glu Cys Lys Cys Val Pro Tyr
            20                  25                  30

<210> SEQ ID NO 197
<211> LENGTH: 31
<212> TYPE: PRT
<213> ORGANISM: Artificial Sequence
<220> FEATURE:
<223> OTHER INFORMATION: Tamapin S11G

<400> SEQUENCE: 197

Ala Phe Cys Asn Leu Arg Arg Cys Glu Leu Gly Cys Arg Ser Leu Gly
1               5                   10                  15

Leu Leu Gly Lys Cys Ile Gly Glu Cys Lys Cys Val Pro Tyr
            20                  25                  30

<210> SEQ ID NO 198
<211> LENGTH: 31
<212> TYPE: PRT
<213> ORGANISM: Artificial Sequence
<220> FEATURE:
<223> OTHER INFORMATION: Tamapin S11H

<400> SEQUENCE: 198

Ala Phe Cys Asn Leu Arg Arg Cys Glu Leu His Cys Arg Ser Leu Gly
1               5                   10                  15

Leu Leu Gly Lys Cys Ile Gly Glu Glu Cys Lys Cys Val Pro Tyr
            20                  25                  30
```

<210> SEQ ID NO 199
<211> LENGTH: 31
<212> TYPE: PRT
<213> ORGANISM: Artificial Sequence
<220> FEATURE:
<223> OTHER INFORMATION: Tamapin S11I

<400> SEQUENCE: 199

Ala Phe Cys Asn Leu Arg Arg Cys Glu Leu Ile Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 200
<211> LENGTH: 31
<212> TYPE: PRT
<213> ORGANISM: Artificial Sequence
<220> FEATURE:
<223> OTHER INFORMATION: Tamapin S11K

<400> SEQUENCE: 200

Ala Phe Cys Asn Leu Arg Arg Cys Glu Leu Lys Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 201
<211> LENGTH: 31
<212> TYPE: PRT
<213> ORGANISM: Artificial Sequence
<220> FEATURE:
<223> OTHER INFORMATION: Tamapin S11L

<400> SEQUENCE: 201

Ala Phe Cys Asn Leu Arg Arg Cys Glu Leu Leu Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 202
<211> LENGTH: 31
<212> TYPE: PRT
<213> ORGANISM: Artificial Sequence
<220> FEATURE:
<223> OTHER INFORMATION: Tamapin S11M

<400> SEQUENCE: 202

Ala Phe Cys Asn Leu Arg Arg Cys Glu Leu Met Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 203
<211> LENGTH: 31
<212> TYPE: PRT
<213> ORGANISM: Artificial Sequence
<220> FEATURE:
<223> OTHER INFORMATION: Tamapin S11N

<400> SEQUENCE: 203

Ala Phe Cys Asn Leu Arg Arg Cys Glu Leu Asn Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 204
<211> LENGTH: 31
<212> TYPE: PRT
<213> ORGANISM: Artificial Sequence
<220> FEATURE:
<223> OTHER INFORMATION: Tamapin S11P

<400> SEQUENCE: 204

Ala Phe Cys Asn Leu Arg Arg Cys Glu Leu Pro Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 205
<211> LENGTH: 31
<212> TYPE: PRT
<213> ORGANISM: Artificial Sequence
<220> FEATURE:
<223> OTHER INFORMATION: Tamapin S11Q

<400> SEQUENCE: 205

Ala Phe Cys Asn Leu Arg Arg Cys Glu Leu Gln Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 206
<211> LENGTH: 31
<212> TYPE: PRT
<213> ORGANISM: Artificial Sequence
<220> FEATURE:
<223> OTHER INFORMATION: Tamapin S11R

<400> SEQUENCE: 206

Ala Phe Cys Asn Leu Arg Arg Cys Glu Leu Arg Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 207
<211> LENGTH: 31
<212> TYPE: PRT
<213> ORGANISM: Artificial Sequence
<220> FEATURE:
<223> OTHER INFORMATION: Tamapin S11T

<400> SEQUENCE: 207

Ala Phe Cys Asn Leu Arg Arg Cys Glu Leu Thr Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 208
<211> LENGTH: 31
<212> TYPE: PRT
<213> ORGANISM: Artificial Sequence
<220> FEATURE:
<223> OTHER INFORMATION: Tamapin S11V

<400> SEQUENCE: 208

Ala Phe Cys Asn Leu Arg Arg Cys Glu Leu Val Cys Arg Ser Leu Gly
1               5                   10                  15

Leu Leu Gly Lys Cys Ile Gly Glu Glu Cys Lys Cys Val Pro Tyr

<210> SEQ ID NO 209
<211> LENGTH: 31
<212> TYPE: PRT
<213> ORGANISM: Artificial Sequence
<220> FEATURE:
<223> OTHER INFORMATION: Tamapin S11W

<400> SEQUENCE: 209

Ala Phe Cys Asn Leu Arg Arg Cys Glu Leu Trp Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 210
<211> LENGTH: 31
<212> TYPE: PRT
<213> ORGANISM: Artificial Sequence
<220> FEATURE:
<223> OTHER INFORMATION: Tamapin S11Y

<400> SEQUENCE: 210

Ala Phe Cys Asn Leu Arg Arg Cys Glu Leu Tyr Cys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 211
<211> LENGTH: 31
<212> TYPE: PRT
<213> ORGANISM: Artificial Sequence
<220> FEATURE:
<223> OTHER INFORMATION: Tamapin C12A

<400> SEQUENCE: 211

Ala Phe Cys Asn Leu Arg Arg Cys Glu Leu Ser Ala Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 212
<211> LENGTH: 31
<212> TYPE: PRT
<213> ORGANISM: Artificial Sequence
<220> FEATURE:
<223> OTHER INFORMATION: Tamapin C12D

<400> SEQUENCE: 212

Ala Phe Cys Asn Leu Arg Arg Cys Glu Leu Ser Asp Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 213
<211> LENGTH: 31
<212> TYPE: PRT
<213> ORGANISM: Artificial Sequence
<220> FEATURE:
<223> OTHER INFORMATION: Tamapin C12E

<400> SEQUENCE: 213

Ala Phe Cys Asn Leu Arg Arg Cys Glu Leu Ser Glu Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 214
<211> LENGTH: 31
<212> TYPE: PRT
<213> ORGANISM: Artificial Sequence
<220> FEATURE:
<223> OTHER INFORMATION: Tamapin C12F

<400> SEQUENCE: 214

Ala Phe Cys Asn Leu Arg Arg Cys Glu Leu Ser Phe Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 215
<211> LENGTH: 31
<212> TYPE: PRT
<213> ORGANISM: Artificial Sequence
<220> FEATURE:
<223> OTHER INFORMATION: Tamapin C12G

<400> SEQUENCE: 215

Ala Phe Cys Asn Leu Arg Arg Cys Glu Leu Ser Gly Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 216
<211> LENGTH: 31
<212> TYPE: PRT
<213> ORGANISM: Artificial Sequence
<220> FEATURE:
<223> OTHER INFORMATION: Tamapin C12H

<400> SEQUENCE: 216

Ala Phe Cys Asn Leu Arg Arg Cys Glu Leu Ser His Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 217
<211> LENGTH: 31
<212> TYPE: PRT
<213> ORGANISM: Artificial Sequence
<220> FEATURE:
<223> OTHER INFORMATION: Tamapin C12I

<400> SEQUENCE: 217

Ala Phe Cys Asn Leu Arg Arg Cys Glu Leu Ser Ile Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 218
<211> LENGTH: 31
<212> TYPE: PRT
<213> ORGANISM: Artificial Sequence
<220> FEATURE:
<223> OTHER INFORMATION: Tamapin C12K

<400> SEQUENCE: 218

Ala Phe Cys Asn Leu Arg Arg Cys Glu Leu Ser Lys Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 219
<211> LENGTH: 31
<212> TYPE: PRT
<213> ORGANISM: Artificial Sequence
<220> FEATURE:
<223> OTHER INFORMATION: Tamapin C12L

<400> SEQUENCE: 219

Ala Phe Cys Asn Leu Arg Arg Cys Glu Leu Ser Leu Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 220
<211> LENGTH: 31
<212> TYPE: PRT
<213> ORGANISM: Artificial Sequence
<220> FEATURE:
<223> OTHER INFORMATION: Tamapin C12M

<400> SEQUENCE: 220

Ala Phe Cys Asn Leu Arg Arg Cys Glu Leu Ser Met Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 221
<211> LENGTH: 31
<212> TYPE: PRT
<213> ORGANISM: Artificial Sequence
<220> FEATURE:
<223> OTHER INFORMATION: Tamapin C12N

<400> SEQUENCE: 221

Ala Phe Cys Asn Leu Arg Arg Cys Glu Leu Ser Asn Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 222
<211> LENGTH: 31
<212> TYPE: PRT
<213> ORGANISM: Artificial Sequence
<220> FEATURE:
<223> OTHER INFORMATION: Tamapin C12P

<400> SEQUENCE: 222

Ala Phe Cys Asn Leu Arg Arg Cys Glu Leu Ser Pro Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 223
<211> LENGTH: 31
<212> TYPE: PRT
<213> ORGANISM: Artificial Sequence
<220> FEATURE:
<223> OTHER INFORMATION: Tamapin C12Q

<400> SEQUENCE: 223

Ala Phe Cys Asn Leu Arg Arg Cys Glu Leu Ser Gln Arg Ser Leu Gly

```
                1               5                  10                  15
Leu Leu Gly Lys Cys Ile Gly Glu Glu Cys Lys Cys Val Pro Tyr
                20                  25                  30
```

<210> SEQ ID NO 224
<211> LENGTH: 31
<212> TYPE: PRT
<213> ORGANISM: Artificial Sequence
<220> FEATURE:
<223> OTHER INFORMATION: Tamapin C12R

<400> SEQUENCE: 224

```
Ala Phe Cys Asn Leu Arg Arg Cys Glu Leu Ser Arg Arg Ser Leu Gly
1               5                  10                  15
Leu Leu Gly Lys Cys Ile Gly Glu Glu Cys Lys Cys Val Pro Tyr
                20                  25                  30
```

<210> SEQ ID NO 225
<211> LENGTH: 31
<212> TYPE: PRT
<213> ORGANISM: Artificial Sequence
<220> FEATURE:
<223> OTHER INFORMATION: Tamapin C12S

<400> SEQUENCE: 225

```
Ala Phe Cys Asn Leu Arg Arg Cys Glu Leu Ser Ser Arg Ser Leu Gly
1               5                  10                  15
Leu Leu Gly Lys Cys Ile Gly Glu Glu Cys Lys Cys Val Pro Tyr
                20                  25                  30
```

<210> SEQ ID NO 226
<211> LENGTH: 31
<212> TYPE: PRT
<213> ORGANISM: Artificial Sequence
<220> FEATURE:
<223> OTHER INFORMATION: Tamapin C12T

<400> SEQUENCE: 226

```
Ala Phe Cys Asn Leu Arg Arg Cys Glu Leu Ser Thr Arg Ser Leu Gly
1               5                  10                  15
Leu Leu Gly Lys Cys Ile Gly Glu Glu Cys Lys Cys Val Pro Tyr
                20                  25                  30
```

<210> SEQ ID NO 227
<211> LENGTH: 31
<212> TYPE: PRT
<213> ORGANISM: Artificial Sequence
<220> FEATURE:
<223> OTHER INFORMATION: Tamapin C12V

<400> SEQUENCE: 227

```
Ala Phe Cys Asn Leu Arg Arg Cys Glu Leu Ser Val Arg Ser Leu Gly
1               5                  10                  15
Leu Leu Gly Lys Cys Ile Gly Glu Glu Cys Lys Cys Val Pro Tyr
                20                  25                  30
```

<210> SEQ ID NO 228
<211> LENGTH: 31
<212> TYPE: PRT
<213> ORGANISM: Artificial Sequence
<220> FEATURE:
<223> OTHER INFORMATION: Tamapin C12W

<400> SEQUENCE: 228

```
Ala Phe Cys Asn Leu Arg Arg Cys Glu Leu Ser Trp Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 229
<211> LENGTH: 31
<212> TYPE: PRT
<213> ORGANISM: Artificial Sequence
<220> FEATURE:
<223> OTHER INFORMATION: Tamapin C12Y

<400> SEQUENCE: 229

Ala Phe Cys Asn Leu Arg Arg Cys Glu Leu Ser Tyr Arg Ser Leu Gly
1               5                   10                  15

Leu Leu Gly Lys Cys Ile Gly Glu Glu Cys Lys Cys Val Pro Tyr
            20                  25                  30

<210> SEQ ID NO 230
<211> LENGTH: 31
<212> TYPE: PRT
<213> ORGANISM: Artificial Sequence
<220> FEATURE:
<223> OTHER INFORMATION: Tamapin R13A

<400> SEQUENCE: 230

Ala Phe Cys Asn Leu Arg Arg Cys Glu Leu Ser Cys Ala Ser Leu Gly
1               5                   10                  15

Leu Leu Gly Lys Cys Ile Gly Glu Glu Cys Lys Cys Val Pro Tyr
            20                  25                  30

<210> SEQ ID NO 231
<211> LENGTH: 31
<212> TYPE: PRT
<213> ORGANISM: Artificial Sequence
<220> FEATURE:
<223> OTHER INFORMATION: Tamapin R13C

<400> SEQUENCE: 231

Ala Phe Cys Asn Leu Arg Arg Cys Glu Leu Ser Cys Cys Ser Leu Gly
1               5                   10                  15

Leu Leu Gly Lys Cys Ile Gly Glu Glu Cys Lys Cys Val Pro Tyr
            20                  25                  30

<210> SEQ ID NO 232
<211> LENGTH: 31
<212> TYPE: PRT
<213> ORGANISM: Artificial Sequence
<220> FEATURE:
<223> OTHER INFORMATION: Tamapin R13D

<400> SEQUENCE: 232

Ala Phe Cys Asn Leu Arg Arg Cys Glu Leu Ser Cys Asp Ser Leu Gly
1               5                   10                  15

Leu Leu Gly Lys Cys Ile Gly Glu Glu Cys Lys Cys Val Pro Tyr
            20                  25                  30

<210> SEQ ID NO 233
<211> LENGTH: 31
<212> TYPE: PRT
<213> ORGANISM: Artificial Sequence
<220> FEATURE:
<223> OTHER INFORMATION: Tamapin R13E

<400> SEQUENCE: 233
```

Ala Phe Cys Asn Leu Arg Arg Cys Glu Leu Ser Cys Glu Ser Leu Gly
1               5                   10                  15

Leu Leu Gly Lys Cys Ile Gly Glu Glu Cys Lys Cys Val Pro Tyr
            20                  25                  30

<210> SEQ ID NO 234
<211> LENGTH: 31
<212> TYPE: PRT
<213> ORGANISM: Artificial Sequence
<220> FEATURE:
<223> OTHER INFORMATION: Tamapin R13F

<400> SEQUENCE: 234

Ala Phe Cys Asn Leu Arg Arg Cys Glu Leu Ser Cys Phe Ser Leu Gly
1               5                   10                  15

Leu Leu Gly Lys Cys Ile Gly Glu Glu Cys Lys Cys Val Pro Tyr
            20                  25                  30

<210> SEQ ID NO 235
<211> LENGTH: 31
<212> TYPE: PRT
<213> ORGANISM: Artificial Sequence
<220> FEATURE:
<223> OTHER INFORMATION: Tamapin R13G

<400> SEQUENCE: 235

Ala Phe Cys Asn Leu Arg Arg Cys Glu Leu Ser Cys Gly Ser Leu Gly
1               5                   10                  15

Leu Leu Gly Lys Cys Ile Gly Glu Glu Cys Lys Cys Val Pro Tyr
            20                  25                  30

<210> SEQ ID NO 236
<211> LENGTH: 31
<212> TYPE: PRT
<213> ORGANISM: Artificial Sequence
<220> FEATURE:
<223> OTHER INFORMATION: Tamapin R13H

<400> SEQUENCE: 236

Ala Phe Cys Asn Leu Arg Arg Cys Glu Leu Ser Cys His Ser Leu Gly
1               5                   10                  15

Leu Leu Gly Lys Cys Ile Gly Glu Glu Cys Lys Cys Val Pro Tyr
            20                  25                  30

<210> SEQ ID NO 237
<211> LENGTH: 31
<212> TYPE: PRT
<213> ORGANISM: Artificial Sequence
<220> FEATURE:
<223> OTHER INFORMATION: Tamapin R13I

<400> SEQUENCE: 237

Ala Phe Cys Asn Leu Arg Arg Cys Glu Leu Ser Cys Ile Ser Leu Gly
1               5                   10                  15

Leu Leu Gly Lys Cys Ile Gly Glu Glu Cys Lys Cys Val Pro Tyr
            20                  25                  30

<210> SEQ ID NO 238
<211> LENGTH: 31
<212> TYPE: PRT
<213> ORGANISM: Artificial Sequence
<220> FEATURE:
<223> OTHER INFORMATION: Tamapin R13K

<400> SEQUENCE: 238

Ala Phe Cys Asn Leu Arg Arg Cys Glu Leu Ser Cys Lys Ser Leu Gly
1               5                   10                  15

Leu Leu Gly Lys Cys Ile Gly Glu Glu Cys Lys Cys Val Pro Tyr
            20                  25                  30

<210> SEQ ID NO 239
<211> LENGTH: 31
<212> TYPE: PRT
<213> ORGANISM: Artificial Sequence
<220> FEATURE:
<223> OTHER INFORMATION: Tamapin R13L

<400> SEQUENCE: 239

Ala Phe Cys Asn Leu Arg Arg Cys Glu Leu Ser Cys Leu Ser Leu Gly
1               5                   10                  15

Leu Leu Gly Lys Cys Ile Gly Glu Glu Cys Lys Cys Val Pro Tyr
            20                  25                  30

<210> SEQ ID NO 240
<211> LENGTH: 31
<212> TYPE: PRT
<213> ORGANISM: Artificial Sequence
<220> FEATURE:
<223> OTHER INFORMATION: Tamapin R13M

<400> SEQUENCE: 240

Ala Phe Cys Asn Leu Arg Arg Cys Glu Leu Ser Cys Met Ser Leu Gly
1               5                   10                  15

Leu Leu Gly Lys Cys Ile Gly Glu Glu Cys Lys Cys Val Pro Tyr
            20                  25                  30

<210> SEQ ID NO 241
<211> LENGTH: 31
<212> TYPE: PRT
<213> ORGANISM: Artificial Sequence
<220> FEATURE:
<223> OTHER INFORMATION: Tamapin R13N

<400> SEQUENCE: 241

Ala Phe Cys Asn Leu Arg Arg Cys Glu Leu Ser Cys Asn Ser Leu Gly
1               5                   10                  15

Leu Leu Gly Lys Cys Ile Gly Glu Glu Cys Lys Cys Val Pro Tyr
            20                  25                  30

<210> SEQ ID NO 242
<211> LENGTH: 31
<212> TYPE: PRT
<213> ORGANISM: Artificial Sequence
<220> FEATURE:
<223> OTHER INFORMATION: Tamapin R13P

<400> SEQUENCE: 242

Ala Phe Cys Asn Leu Arg Arg Cys Glu Leu Ser Cys Pro Ser Leu Gly
1               5                   10                  15

Leu Leu Gly Lys Cys Ile Gly Glu Glu Cys Lys Cys Val Pro Tyr
            20                  25                  30

<210> SEQ ID NO 243
<211> LENGTH: 31
<212> TYPE: PRT
<213> ORGANISM: Artificial Sequence
<220> FEATURE:
<223> OTHER INFORMATION: Tamapin R13Q

<400> SEQUENCE: 243

Ala Phe Cys Asn Leu Arg Arg Cys Glu Leu Ser Cys Gln Ser Leu Gly
1               5                   10                  15

Leu Leu Gly Lys Cys Ile Gly Glu Glu Cys Lys Cys Val Pro Tyr
            20                  25                  30

<210> SEQ ID NO 244
<211> LENGTH: 31
<212> TYPE: PRT
<213> ORGANISM: Artificial Sequence
<220> FEATURE:
<223> OTHER INFORMATION: Tamapin R13S

<400> SEQUENCE: 244

Ala Phe Cys Asn Leu Arg Arg Cys Glu Leu Ser Cys Ser Ser Leu Gly
1               5                   10                  15

Leu Leu Gly Lys Cys Ile Gly Glu Glu Cys Lys Cys Val Pro Tyr
            20                  25                  30

<210> SEQ ID NO 245
<211> LENGTH: 31
<212> TYPE: PRT
<213> ORGANISM: Artificial Sequence
<220> FEATURE:
<223> OTHER INFORMATION: Tamapin R13T

<400> SEQUENCE: 245

Ala Phe Cys Asn Leu Arg Arg Cys Glu Leu Ser Cys Thr Ser Leu Gly
1               5                   10                  15

Leu Leu Gly Lys Cys Ile Gly Glu Glu Cys Lys Cys Val Pro Tyr
            20                  25                  30

<210> SEQ ID NO 246
<211> LENGTH: 31
<212> TYPE: PRT
<213> ORGANISM: Artificial Sequence
<220> FEATURE:
<223> OTHER INFORMATION: Tamapin R13V

<400> SEQUENCE: 246

Ala Phe Cys Asn Leu Arg Arg Cys Glu Leu Ser Cys Val Ser Leu Gly
1               5                   10                  15

Leu Leu Gly Lys Cys Ile Gly Glu Glu Cys Lys Cys Val Pro Tyr
            20                  25                  30

<210> SEQ ID NO 247
<211> LENGTH: 31
<212> TYPE: PRT
<213> ORGANISM: Artificial Sequence
<220> FEATURE:
<223> OTHER INFORMATION: Tamapin R13W

<400> SEQUENCE: 247

Ala Phe Cys Asn Leu Arg Arg Cys Glu Leu Ser Cys Trp Ser Leu Gly
1               5                   10                  15

Leu Leu Gly Lys Cys Ile Gly Glu Glu Cys Lys Cys Val Pro Tyr
            20                  25                  30

<210> SEQ ID NO 248
<211> LENGTH: 31
<212> TYPE: PRT
<213> ORGANISM: Artificial Sequence
<220> FEATURE:

<223> OTHER INFORMATION: Tamapin R13Y

<400> SEQUENCE: 248

Ala Phe Cys Asn Leu Arg Arg Cys Glu Leu Ser Cys Tyr Ser Leu Gly
1               5                   10                  15

Leu Leu Gly Lys Cys Ile Gly Glu Glu Cys Lys Cys Val Pro Tyr
            20                  25                  30

<210> SEQ ID NO 249
<211> LENGTH: 31
<212> TYPE: PRT
<213> ORGANISM: Artificial Sequence
<220> FEATURE:
<223> OTHER INFORMATION: Tamapin S14A

<400> SEQUENCE: 249

Ala Phe Cys Asn Leu Arg Arg Cys Glu Leu Ser Cys Arg Ala Leu Gly
1               5                   10                  15

Leu Leu Gly Lys Cys Ile Gly Glu Glu Cys Lys Cys Val Pro Tyr
            20                  25                  30

<210> SEQ ID NO 250
<211> LENGTH: 31
<212> TYPE: PRT
<213> ORGANISM: Artificial Sequence
<220> FEATURE:
<223> OTHER INFORMATION: Tamapin analog

<400> SEQUENCE: 250

Ala Phe Cys Asn Leu Arg Arg Cys Glu Leu Ser Cys Arg Cys Leu Gly
1               5                   10                  15

Leu Leu Gly Lys Cys Ile Gly Glu Glu Cys Lys Cys Val Pro Tyr
            20                  25                  30

<210> SEQ ID NO 251
<211> LENGTH: 31
<212> TYPE: PRT
<213> ORGANISM: Artificial Sequence
<220> FEATURE:
<223> OTHER INFORMATION: Tamapin S14D

<400> SEQUENCE: 251

Ala Phe Cys Asn Leu Arg Arg Cys Glu Leu Ser Cys Arg Asp Leu Gly
1               5                   10                  15

Leu Leu Gly Lys Cys Ile Gly Glu Glu Cys Lys Cys Val Pro Tyr
            20                  25                  30

<210> SEQ ID NO 252
<211> LENGTH: 31
<212> TYPE: PRT
<213> ORGANISM: Artificial Sequence
<220> FEATURE:
<223> OTHER INFORMATION: Tamapin S14E

<400> SEQUENCE: 252

Ala Phe Cys Asn Leu Arg Arg Cys Glu Leu Ser Cys Arg Glu Leu Gly
1               5                   10                  15

Leu Leu Gly Lys Cys Ile Gly Glu Glu Cys Lys Cys Val Pro Tyr
            20                  25                  30

<210> SEQ ID NO 253
<211> LENGTH: 31
<212> TYPE: PRT
<213> ORGANISM: Artificial Sequence

```
<220> FEATURE:
<223> OTHER INFORMATION: Tamapin S14F

<400> SEQUENCE: 253

Ala Phe Cys Asn Leu Arg Arg Cys Glu Leu Ser Cys Arg Phe Leu Gly
1               5                   10                  15
Leu Leu Gly Lys Cys Ile Gly Glu Glu Cys Lys Cys Val Pro Tyr
            20                  25                  30

<210> SEQ ID NO 254
<211> LENGTH: 31
<212> TYPE: PRT
<213> ORGANISM: Artificial Sequence
<220> FEATURE:
<223> OTHER INFORMATION: Tamapin S14G

<400> SEQUENCE: 254

Ala Phe Cys Asn Leu Arg Arg Cys Glu Leu Ser Cys Arg Gly Leu Gly
1               5                   10                  15
Leu Leu Gly Lys Cys Ile Gly Glu Glu Cys Lys Cys Val Pro Tyr
            20                  25                  30

<210> SEQ ID NO 255
<211> LENGTH: 31
<212> TYPE: PRT
<213> ORGANISM: Artificial Sequence
<220> FEATURE:
<223> OTHER INFORMATION: Tamapin S14H

<400> SEQUENCE: 255

Ala Phe Cys Asn Leu Arg Arg Cys Glu Leu Ser Cys Arg His Leu Gly
1               5                   10                  15
Leu Leu Gly Lys Cys Ile Gly Glu Glu Cys Lys Cys Val Pro Tyr
            20                  25                  30

<210> SEQ ID NO 256
<211> LENGTH: 31
<212> TYPE: PRT
<213> ORGANISM: Artificial Sequence
<220> FEATURE:
<223> OTHER INFORMATION: Tamapin S14I

<400> SEQUENCE: 256

Ala Phe Cys Asn Leu Arg Arg Cys Glu Leu Ser Cys Arg Ile Leu Gly
1               5                   10                  15
Leu Leu Gly Lys Cys Ile Gly Glu Glu Cys Lys Cys Val Pro Tyr
            20                  25                  30

<210> SEQ ID NO 257
<211> LENGTH: 31
<212> TYPE: PRT
<213> ORGANISM: Artificial Sequence
<220> FEATURE:
<223> OTHER INFORMATION: Tamapin S14K

<400> SEQUENCE: 257

Ala Phe Cys Asn Leu Arg Arg Cys Glu Leu Ser Cys Arg Lys Leu Gly
1               5                   10                  15
Leu Leu Gly Lys Cys Ile Gly Glu Glu Cys Lys Cys Val Pro Tyr
            20                  25                  30

<210> SEQ ID NO 258
<211> LENGTH: 31
<212> TYPE: PRT
```

<213> ORGANISM: Artificial Sequence
<220> FEATURE:
<223> OTHER INFORMATION: Tamapin S14L

<400> SEQUENCE: 258

Ala Phe Cys Asn Leu Arg Arg Cys Glu Leu Ser Cys Arg Leu Leu Gly
1               5                   10                  15

Leu Leu Gly Lys Cys Ile Gly Glu Glu Cys Lys Cys Val Pro Tyr
            20                  25                  30

<210> SEQ ID NO 259
<211> LENGTH: 31
<212> TYPE: PRT
<213> ORGANISM: Artificial Sequence
<220> FEATURE:
<223> OTHER INFORMATION: Tamapin S14M

<400> SEQUENCE: 259

Ala Phe Cys Asn Leu Arg Arg Cys Glu Leu Ser Cys Arg Met Leu Gly
1               5                   10                  15

Leu Leu Gly Lys Cys Ile Gly Glu Glu Cys Lys Cys Val Pro Tyr
            20                  25                  30

<210> SEQ ID NO 260
<211> LENGTH: 31
<212> TYPE: PRT
<213> ORGANISM: Artificial Sequence
<220> FEATURE:
<223> OTHER INFORMATION: Tamapin S14N

<400> SEQUENCE: 260

Ala Phe Cys Asn Leu Arg Arg Cys Glu Leu Ser Cys Arg Asn Leu Gly
1               5                   10                  15

Leu Leu Gly Lys Cys Ile Gly Glu Glu Cys Lys Cys Val Pro Tyr
            20                  25                  30

<210> SEQ ID NO 261
<211> LENGTH: 31
<212> TYPE: PRT
<213> ORGANISM: Artificial Sequence
<220> FEATURE:
<223> OTHER INFORMATION: Tamapin S14P

<400> SEQUENCE: 261

Ala Phe Cys Asn Leu Arg Arg Cys Glu Leu Ser Cys Arg Pro Leu Gly
1               5                   10                  15

Leu Leu Gly Lys Cys Ile Gly Glu Glu Cys Lys Cys Val Pro Tyr
            20                  25                  30

<210> SEQ ID NO 262
<211> LENGTH: 31
<212> TYPE: PRT
<213> ORGANISM: Artificial Sequence
<220> FEATURE:
<223> OTHER INFORMATION: Tamapin S14Q

<400> SEQUENCE: 262

Ala Phe Cys Asn Leu Arg Arg Cys Glu Leu Ser Cys Arg Gln Leu Gly
1               5                   10                  15

Leu Leu Gly Lys Cys Ile Gly Glu Glu Cys Lys Cys Val Pro Tyr
            20                  25                  30

<210> SEQ ID NO 263
<211> LENGTH: 31

```
<212> TYPE: PRT
<213> ORGANISM: Artificial Sequence
<220> FEATURE:
<223> OTHER INFORMATION: Tamapin S14R

<400> SEQUENCE: 263

Ala Phe Cys Asn Leu Arg Arg Cys Glu Leu Ser Cys Arg Arg Leu Gly
1               5                   10                  15

Leu Leu Gly Lys Cys Ile Gly Glu Glu Cys Lys Cys Val Pro Tyr
            20                  25                  30

<210> SEQ ID NO 264
<211> LENGTH: 31
<212> TYPE: PRT
<213> ORGANISM: Artificial Sequence
<220> FEATURE:
<223> OTHER INFORMATION: Tamapin S14T

<400> SEQUENCE: 264

Ala Phe Cys Asn Leu Arg Arg Cys Glu Leu Ser Cys Arg Thr Leu Gly
1               5                   10                  15

Leu Leu Gly Lys Cys Ile Gly Glu Glu Cys Lys Cys Val Pro Tyr
            20                  25                  30

<210> SEQ ID NO 265
<211> LENGTH: 31
<212> TYPE: PRT
<213> ORGANISM: Artificial Sequence
<220> FEATURE:
<223> OTHER INFORMATION: Tamapin S14V

<400> SEQUENCE: 265

Ala Phe Cys Asn Leu Arg Arg Cys Glu Leu Ser Cys Arg Val Leu Gly
1               5                   10                  15

Leu Leu Gly Lys Cys Ile Gly Glu Glu Cys Lys Cys Val Pro Tyr
            20                  25                  30

<210> SEQ ID NO 266
<211> LENGTH: 31
<212> TYPE: PRT
<213> ORGANISM: Artificial Sequence
<220> FEATURE:
<223> OTHER INFORMATION: Tamapin S14W

<400> SEQUENCE: 266

Ala Phe Cys Asn Leu Arg Arg Cys Glu Leu Ser Cys Arg Trp Leu Gly
1               5                   10                  15

Leu Leu Gly Lys Cys Ile Gly Glu Glu Cys Lys Cys Val Pro Tyr
            20                  25                  30

<210> SEQ ID NO 267
<211> LENGTH: 31
<212> TYPE: PRT
<213> ORGANISM: Artificial Sequence
<220> FEATURE:
<223> OTHER INFORMATION: Tamapin S14Y

<400> SEQUENCE: 267

Ala Phe Cys Asn Leu Arg Arg Cys Glu Leu Ser Cys Arg Tyr Leu Gly
1               5                   10                  15

Leu Leu Gly Lys Cys Ile Gly Glu Glu Cys Lys Cys Val Pro Tyr
            20                  25                  30

<210> SEQ ID NO 268
```

```
<211> LENGTH: 31
<212> TYPE: PRT
<213> ORGANISM: Artificial Sequence
<220> FEATURE:
<223> OTHER INFORMATION: Tamapin L15A

<400> SEQUENCE: 268

Ala Phe Cys Asn Leu Arg Arg Cys Glu Leu Ser Cys Arg Ser Ala Gly
1               5                   10                  15
Leu Leu Gly Lys Cys Ile Gly Glu Glu Cys Lys Cys Val Pro Tyr
            20                  25                  30

<210> SEQ ID NO 269
<211> LENGTH: 31
<212> TYPE: PRT
<213> ORGANISM: Artificial Sequence
<220> FEATURE:
<223> OTHER INFORMATION: Tamapin L15C

<400> SEQUENCE: 269

Ala Phe Cys Asn Leu Arg Arg Cys Glu Leu Ser Cys Arg Ser Cys Gly
1               5                   10                  15
Leu Leu Gly Lys Cys Ile Gly Glu Glu Cys Lys Cys Val Pro Tyr
            20                  25                  30

<210> SEQ ID NO 270
<211> LENGTH: 31
<212> TYPE: PRT
<213> ORGANISM: Artificial Sequence
<220> FEATURE:
<223> OTHER INFORMATION: Tamapin L15D

<400> SEQUENCE: 270

Ala Phe Cys Asn Leu Arg Arg Cys Glu Leu Ser Cys Arg Ser Asp Gly
1               5                   10                  15
Leu Leu Gly Lys Cys Ile Gly Glu Glu Cys Lys Cys Val Pro Tyr
            20                  25                  30

<210> SEQ ID NO 271
<211> LENGTH: 31
<212> TYPE: PRT
<213> ORGANISM: Artificial Sequence
<220> FEATURE:
<223> OTHER INFORMATION: Tamapin L15E

<400> SEQUENCE: 271

Ala Phe Cys Asn Leu Arg Arg Cys Glu Leu Ser Cys Arg Ser Glu Gly
1               5                   10                  15
Leu Leu Gly Lys Cys Ile Gly Glu Glu Cys Lys Cys Val Pro Tyr
            20                  25                  30

<210> SEQ ID NO 272
<211> LENGTH: 31
<212> TYPE: PRT
<213> ORGANISM: Artificial Sequence
<220> FEATURE:
<223> OTHER INFORMATION: Tamapin L15F

<400> SEQUENCE: 272

Ala Phe Cys Asn Leu Arg Arg Cys Glu Leu Ser Cys Arg Ser Phe Gly
1               5                   10                  15
Leu Leu Gly Lys Cys Ile Gly Glu Glu Cys Lys Cys Val Pro Tyr
            20                  25                  30
```

-continued

<210> SEQ ID NO 273
<211> LENGTH: 31
<212> TYPE: PRT
<213> ORGANISM: Artificial Sequence
<220> FEATURE:
<223> OTHER INFORMATION: Tamapin L15G

<400> SEQUENCE: 273

Ala Phe Cys Asn Leu Arg Arg Cys Glu Leu Ser Cys Arg Ser Gly Gly
1               5                   10                  15

Leu Leu Gly Lys Cys Ile Gly Glu Glu Cys Lys Cys Val Pro Tyr
            20                  25                  30

<210> SEQ ID NO 274
<211> LENGTH: 31
<212> TYPE: PRT
<213> ORGANISM: Artificial Sequence
<220> FEATURE:
<223> OTHER INFORMATION: Tamapin L15H

<400> SEQUENCE: 274

Ala Phe Cys Asn Leu Arg Arg Cys Glu Leu Ser Cys Arg Ser His Gly
1               5                   10                  15

Leu Leu Gly Lys Cys Ile Gly Glu Glu Cys Lys Cys Val Pro Tyr
            20                  25                  30

<210> SEQ ID NO 275
<211> LENGTH: 31
<212> TYPE: PRT
<213> ORGANISM: Artificial Sequence
<220> FEATURE:
<223> OTHER INFORMATION: Tamapin L15I

<400> SEQUENCE: 275

Ala Phe Cys Asn Leu Arg Arg Cys Glu Leu Ser Cys Arg Ser Ile Gly
1               5                   10                  15

Leu Leu Gly Lys Cys Ile Gly Glu Glu Cys Lys Cys Val Pro Tyr
            20                  25                  30

<210> SEQ ID NO 276
<211> LENGTH: 31
<212> TYPE: PRT
<213> ORGANISM: Artificial Sequence
<220> FEATURE:
<223> OTHER INFORMATION: Tamapin L15K

<400> SEQUENCE: 276

Ala Phe Cys Asn Leu Arg Arg Cys Glu Leu Ser Cys Arg Ser Lys Gly
1               5                   10                  15

Leu Leu Gly Lys Cys Ile Gly Glu Glu Cys Lys Cys Val Pro Tyr
            20                  25                  30

<210> SEQ ID NO 277
<211> LENGTH: 31
<212> TYPE: PRT
<213> ORGANISM: Artificial Sequence
<220> FEATURE:
<223> OTHER INFORMATION: Tamapin L15M

<400> SEQUENCE: 277

Ala Phe Cys Asn Leu Arg Arg Cys Glu Leu Ser Cys Arg Ser Met Gly
1               5                   10                  15

Leu Leu Gly Lys Cys Ile Gly Glu Glu Cys Lys Cys Val Pro Tyr
            20                  25                  30

<210> SEQ ID NO 278
<211> LENGTH: 31
<212> TYPE: PRT
<213> ORGANISM: Artificial Sequence
<220> FEATURE:
<223> OTHER INFORMATION: Tamapin L15N

<400> SEQUENCE: 278

Ala Phe Cys Asn Leu Arg Arg Cys Glu Leu Ser Cys Arg Ser Asn Gly
1               5                   10                  15

Leu Leu Gly Lys Cys Ile Gly Glu Glu Cys Lys Cys Val Pro Tyr
            20                  25                  30

<210> SEQ ID NO 279
<211> LENGTH: 31
<212> TYPE: PRT
<213> ORGANISM: Artificial Sequence
<220> FEATURE:
<223> OTHER INFORMATION: Tamapin L15P

<400> SEQUENCE: 279

Ala Phe Cys Asn Leu Arg Arg Cys Glu Leu Ser Cys Arg Ser Pro Gly
1               5                   10                  15

Leu Leu Gly Lys Cys Ile Gly Glu Glu Cys Lys Cys Val Pro Tyr
            20                  25                  30

<210> SEQ ID NO 280
<211> LENGTH: 31
<212> TYPE: PRT
<213> ORGANISM: Artificial Sequence
<220> FEATURE:
<223> OTHER INFORMATION: Tamapin L15Q

<400> SEQUENCE: 280

Ala Phe Cys Asn Leu Arg Arg Cys Glu Leu Ser Cys Arg Ser Gln Gly
1               5                   10                  15

Leu Leu Gly Lys Cys Ile Gly Glu Glu Cys Lys Cys Val Pro Tyr
            20                  25                  30

<210> SEQ ID NO 281
<211> LENGTH: 31
<212> TYPE: PRT
<213> ORGANISM: Artificial Sequence
<220> FEATURE:
<223> OTHER INFORMATION: Tamapin L15R

<400> SEQUENCE: 281

Ala Phe Cys Asn Leu Arg Arg Cys Glu Leu Ser Cys Arg Ser Arg Gly
1               5                   10                  15

Leu Leu Gly Lys Cys Ile Gly Glu Glu Cys Lys Cys Val Pro Tyr
            20                  25                  30

<210> SEQ ID NO 282
<211> LENGTH: 31
<212> TYPE: PRT
<213> ORGANISM: Artificial Sequence
<220> FEATURE:
<223> OTHER INFORMATION: Tamapin L15S

<400> SEQUENCE: 282

Ala Phe Cys Asn Leu Arg Arg Cys Glu Leu Ser Cys Arg Ser Ser Gly
1               5                   10                  15

Leu Leu Gly Lys Cys Ile Gly Glu Glu Cys Lys Cys Val Pro Tyr
            20                  25                  30

```
<210> SEQ ID NO 283
<211> LENGTH: 31
<212> TYPE: PRT
<213> ORGANISM: Artificial Sequence
<220> FEATURE:
<223> OTHER INFORMATION: Tamapin L15T

<400> SEQUENCE: 283

Ala Phe Cys Asn Leu Arg Arg Cys Glu Leu Ser Cys Arg Ser Thr Gly
1               5                   10                  15

Leu Leu Gly Lys Cys Ile Gly Glu Glu Cys Lys Cys Val Pro Tyr
            20                  25                  30

<210> SEQ ID NO 284
<211> LENGTH: 31
<212> TYPE: PRT
<213> ORGANISM: Artificial Sequence
<220> FEATURE:
<223> OTHER INFORMATION: Tamapin L15V

<400> SEQUENCE: 284

Ala Phe Cys Asn Leu Arg Arg Cys Glu Leu Ser Cys Arg Ser Val Gly
1               5                   10                  15

Leu Leu Gly Lys Cys Ile Gly Glu Glu Cys Lys Cys Val Pro Tyr
            20                  25                  30

<210> SEQ ID NO 285
<211> LENGTH: 31
<212> TYPE: PRT
<213> ORGANISM: Artificial Sequence
<220> FEATURE:
<223> OTHER INFORMATION: Tamapin L15W

<400> SEQUENCE: 285

Ala Phe Cys Asn Leu Arg Arg Cys Glu Leu Ser Cys Arg Ser Trp Gly
1               5                   10                  15

Leu Leu Gly Lys Cys Ile Gly Glu Glu Cys Lys Cys Val Pro Tyr
            20                  25                  30

<210> SEQ ID NO 286
<211> LENGTH: 31
<212> TYPE: PRT
<213> ORGANISM: Artificial Sequence
<220> FEATURE:
<223> OTHER INFORMATION: Tamapin L15Y

<400> SEQUENCE: 286

Ala Phe Cys Asn Leu Arg Arg Cys Glu Leu Ser Cys Arg Ser Tyr Gly
1               5                   10                  15

Leu Leu Gly Lys Cys Ile Gly Glu Glu Cys Lys Cys Val Pro Tyr
            20                  25                  30

<210> SEQ ID NO 287
<211> LENGTH: 31
<212> TYPE: PRT
<213> ORGANISM: Artificial Sequence
<220> FEATURE:
<223> OTHER INFORMATION: Tamapin G16A

<400> SEQUENCE: 287

Ala Phe Cys Asn Leu Arg Arg Cys Glu Leu Ser Cys Arg Ser Leu Ala
1               5                   10                  15

Leu Leu Gly Lys Cys Ile Gly Glu Glu Cys Lys Cys Val Pro Tyr
```

-continued

```
                 20                  25                  30

<210> SEQ ID NO 288
<211> LENGTH: 31
<212> TYPE: PRT
<213> ORGANISM: Artificial Sequence
<220> FEATURE:
<223> OTHER INFORMATION: Tamapin G16C

<400> SEQUENCE: 288

Ala Phe Cys Asn Leu Arg Arg Cys Glu Leu Ser Cys Arg Ser Leu Cys
1               5                   10                  15

Leu Leu Gly Lys Cys Ile Gly Glu Glu Cys Lys Cys Val Pro Tyr
            20                  25                  30

<210> SEQ ID NO 289
<211> LENGTH: 31
<212> TYPE: PRT
<213> ORGANISM: Artificial Sequence
<220> FEATURE:
<223> OTHER INFORMATION: Tamapin G16D

<400> SEQUENCE: 289

Ala Phe Cys Asn Leu Arg Arg Cys Glu Leu Ser Cys Arg Ser Leu Asp
1               5                   10                  15

Leu Leu Gly Lys Cys Ile Gly Glu Glu Cys Lys Cys Val Pro Tyr
            20                  25                  30

<210> SEQ ID NO 290
<211> LENGTH: 31
<212> TYPE: PRT
<213> ORGANISM: Artificial Sequence
<220> FEATURE:
<223> OTHER INFORMATION: Tamapin G16E

<400> SEQUENCE: 290

Ala Phe Cys Asn Leu Arg Arg Cys Glu Leu Ser Cys Arg Ser Leu Glu
1               5                   10                  15

Leu Leu Gly Lys Cys Ile Gly Glu Glu Cys Lys Cys Val Pro Tyr
            20                  25                  30

<210> SEQ ID NO 291
<211> LENGTH: 31
<212> TYPE: PRT
<213> ORGANISM: Artificial Sequence
<220> FEATURE:
<223> OTHER INFORMATION: Tamapin G16F

<400> SEQUENCE: 291

Ala Phe Cys Asn Leu Arg Arg Cys Glu Leu Ser Cys Arg Ser Leu Phe
1               5                   10                  15

Leu Leu Gly Lys Cys Ile Gly Glu Glu Cys Lys Cys Val Pro Tyr
            20                  25                  30

<210> SEQ ID NO 292
<211> LENGTH: 31
<212> TYPE: PRT
<213> ORGANISM: Artificial Sequence
<220> FEATURE:
<223> OTHER INFORMATION: Tamapin G16H

<400> SEQUENCE: 292

Ala Phe Cys Asn Leu Arg Arg Cys Glu Leu Ser Cys Arg Ser Leu His
1               5                   10                  15
```

Leu Leu Gly Lys Cys Ile Gly Glu Glu Cys Lys Cys Val Pro Tyr
            20                  25                  30

<210> SEQ ID NO 293
<211> LENGTH: 31
<212> TYPE: PRT
<213> ORGANISM: Artificial Sequence
<220> FEATURE:
<223> OTHER INFORMATION: Tamapin G16I

<400> SEQUENCE: 293

Ala Phe Cys Asn Leu Arg Arg Cys Glu Leu Ser Cys Arg Ser Leu Ile
1               5                   10                  15

Leu Leu Gly Lys Cys Ile Gly Glu Glu Cys Lys Cys Val Pro Tyr
            20                  25                  30

<210> SEQ ID NO 294
<211> LENGTH: 31
<212> TYPE: PRT
<213> ORGANISM: Artificial Sequence
<220> FEATURE:
<223> OTHER INFORMATION: Tamapin G16K

<400> SEQUENCE: 294

Ala Phe Cys Asn Leu Arg Arg Cys Glu Leu Ser Cys Arg Ser Leu Lys
1               5                   10                  15

Leu Leu Gly Lys Cys Ile Gly Glu Glu Cys Lys Cys Val Pro Tyr
            20                  25                  30

<210> SEQ ID NO 295
<211> LENGTH: 31
<212> TYPE: PRT
<213> ORGANISM: Artificial Sequence
<220> FEATURE:
<223> OTHER INFORMATION: Tamapin G16L

<400> SEQUENCE: 295

Ala Phe Cys Asn Leu Arg Arg Cys Glu Leu Ser Cys Arg Ser Leu Leu
1               5                   10                  15

Leu Leu Gly Lys Cys Ile Gly Glu Glu Cys Lys Cys Val Pro Tyr
            20                  25                  30

<210> SEQ ID NO 296
<211> LENGTH: 31
<212> TYPE: PRT
<213> ORGANISM: Artificial Sequence
<220> FEATURE:
<223> OTHER INFORMATION: Tamapin G16M

<400> SEQUENCE: 296

Ala Phe Cys Asn Leu Arg Arg Cys Glu Leu Ser Cys Arg Ser Leu Met
1               5                   10                  15

Leu Leu Gly Lys Cys Ile Gly Glu Glu Cys Lys Cys Val Pro Tyr
            20                  25                  30

<210> SEQ ID NO 297
<211> LENGTH: 31
<212> TYPE: PRT
<213> ORGANISM: Artificial Sequence
<220> FEATURE:
<223> OTHER INFORMATION: Tamapin G16N

<400> SEQUENCE: 297

Ala Phe Cys Asn Leu Arg Arg Cys Glu Leu Ser Cys Arg Ser Leu Asn
1               5                   10                  15

```
Leu Leu Gly Lys Cys Ile Gly Glu Glu Cys Lys Cys Val Pro Tyr
            20                  25                  30
```

<210> SEQ ID NO 298
<211> LENGTH: 31
<212> TYPE: PRT
<213> ORGANISM: Artificial Sequence
<220> FEATURE:
<223> OTHER INFORMATION: Tamapin G16P

<400> SEQUENCE: 298

```
Ala Phe Cys Asn Leu Arg Arg Cys Glu Leu Ser Cys Arg Ser Leu Pro
1               5                   10                  15

Leu Leu Gly Lys Cys Ile Gly Glu Glu Cys Lys Cys Val Pro Tyr
            20                  25                  30
```

<210> SEQ ID NO 299
<211> LENGTH: 31
<212> TYPE: PRT
<213> ORGANISM: Artificial Sequence
<220> FEATURE:
<223> OTHER INFORMATION: Tamapin G16Q

<400> SEQUENCE: 299

```
Ala Phe Cys Asn Leu Arg Arg Cys Glu Leu Ser Cys Arg Ser Leu Gln
1               5                   10                  15

Leu Leu Gly Lys Cys Ile Gly Glu Glu Cys Lys Cys Val Pro Tyr
            20                  25                  30
```

<210> SEQ ID NO 300
<211> LENGTH: 31
<212> TYPE: PRT
<213> ORGANISM: Artificial Sequence
<220> FEATURE:
<223> OTHER INFORMATION: Tamapin G16R

<400> SEQUENCE: 300

```
Ala Phe Cys Asn Leu Arg Arg Cys Glu Leu Ser Cys Arg Ser Leu Arg
1               5                   10                  15

Leu Leu Gly Lys Cys Ile Gly Glu Glu Cys Lys Cys Val Pro Tyr
            20                  25                  30
```

<210> SEQ ID NO 301
<211> LENGTH: 31
<212> TYPE: PRT
<213> ORGANISM: Artificial Sequence
<220> FEATURE:
<223> OTHER INFORMATION: Tamapin G16S

<400> SEQUENCE: 301

```
Ala Phe Cys Asn Leu Arg Arg Cys Glu Leu Ser Cys Arg Ser Leu Ser
1               5                   10                  15

Leu Leu Gly Lys Cys Ile Gly Glu Glu Cys Lys Cys Val Pro Tyr
            20                  25                  30
```

<210> SEQ ID NO 302
<211> LENGTH: 31
<212> TYPE: PRT
<213> ORGANISM: Artificial Sequence
<220> FEATURE:
<223> OTHER INFORMATION: Tamapin G16T

<400> SEQUENCE: 302

```
Ala Phe Cys Asn Leu Arg Arg Cys Glu Leu Ser Cys Arg Ser Leu Thr
```

```
                1               5                  10                  15
Leu Leu Gly Lys Cys Ile Gly Glu Glu Cys Lys Cys Val Pro Tyr
                20                  25                  30
```

<210> SEQ ID NO 303
<211> LENGTH: 31
<212> TYPE: PRT
<213> ORGANISM: Artificial Sequence
<220> FEATURE:
<223> OTHER INFORMATION: Tamapin G16V

<400> SEQUENCE: 303

```
Ala Phe Cys Asn Leu Arg Arg Cys Glu Leu Ser Cys Arg Ser Leu Val
1               5                  10                  15
Leu Leu Gly Lys Cys Ile Gly Glu Glu Cys Lys Cys Val Pro Tyr
                20                  25                  30
```

<210> SEQ ID NO 304
<211> LENGTH: 31
<212> TYPE: PRT
<213> ORGANISM: Artificial Sequence
<220> FEATURE:
<223> OTHER INFORMATION: Tamapin G16W

<400> SEQUENCE: 304

```
Ala Phe Cys Asn Leu Arg Arg Cys Glu Leu Ser Cys Arg Ser Leu Trp
1               5                  10                  15
Leu Leu Gly Lys Cys Ile Gly Glu Glu Cys Lys Cys Val Pro Tyr
                20                  25                  30
```

<210> SEQ ID NO 305
<211> LENGTH: 31
<212> TYPE: PRT
<213> ORGANISM: Artificial Sequence
<220> FEATURE:
<223> OTHER INFORMATION: Tamapin G16Y

<400> SEQUENCE: 305

```
Ala Phe Cys Asn Leu Arg Arg Cys Glu Leu Ser Cys Arg Ser Leu Tyr
1               5                  10                  15
Leu Leu Gly Lys Cys Ile Gly Glu Glu Cys Lys Cys Val Pro Tyr
                20                  25                  30
```

<210> SEQ ID NO 306
<211> LENGTH: 31
<212> TYPE: PRT
<213> ORGANISM: Artificial Sequence
<220> FEATURE:
<223> OTHER INFORMATION: Tamapin L17A

<400> SEQUENCE: 306

```
Ala Phe Cys Asn Leu Arg Arg Cys Glu Leu Ser Cys Arg Ser Leu Gly
1               5                  10                  15
Ala Leu Gly Lys Cys Ile Gly Glu Glu Cys Lys Cys Val Pro Tyr
                20                  25                  30
```

<210> SEQ ID NO 307
<211> LENGTH: 31
<212> TYPE: PRT
<213> ORGANISM: Artificial Sequence
<220> FEATURE:
<223> OTHER INFORMATION: Tamapin L17C

<400> SEQUENCE: 307

```
Ala Phe Cys Asn Leu Arg Arg Cys Glu Leu Ser Cys Arg Ser Leu Gly
  1               5                  10                  15

Cys Leu Gly Lys Cys Ile Gly Glu Glu Cys Lys Cys Val Pro Tyr
             20                  25                  30

<210> SEQ ID NO 308
<211> LENGTH: 31
<212> TYPE: PRT
<213> ORGANISM: Artificial Sequence
<220> FEATURE:
<223> OTHER INFORMATION: Tamapin L17D

<400> SEQUENCE: 308

Ala Phe Cys Asn Leu Arg Arg Cys Glu Leu Ser Cys Arg Ser Leu Gly
  1               5                  10                  15

Asp Leu Gly Lys Cys Ile Gly Glu Glu Cys Lys Cys Val Pro Tyr
             20                  25                  30

<210> SEQ ID NO 309
<211> LENGTH: 31
<212> TYPE: PRT
<213> ORGANISM: Artificial Sequence
<220> FEATURE:
<223> OTHER INFORMATION: Tamapin L17E

<400> SEQUENCE: 309

Ala Phe Cys Asn Leu Arg Arg Cys Glu Leu Ser Cys Arg Ser Leu Gly
  1               5                  10                  15

Glu Leu Gly Lys Cys Ile Gly Glu Glu Cys Lys Cys Val Pro Tyr
             20                  25                  30

<210> SEQ ID NO 310
<211> LENGTH: 31
<212> TYPE: PRT
<213> ORGANISM: Artificial Sequence
<220> FEATURE:
<223> OTHER INFORMATION: Tamapin L17F

<400> SEQUENCE: 310

Ala Phe Cys Asn Leu Arg Arg Cys Glu Leu Ser Cys Arg Ser Leu Gly
  1               5                  10                  15

Phe Leu Gly Lys Cys Ile Gly Glu Glu Cys Lys Cys Val Pro Tyr
             20                  25                  30

<210> SEQ ID NO 311
<211> LENGTH: 31
<212> TYPE: PRT
<213> ORGANISM: Artificial Sequence
<220> FEATURE:
<223> OTHER INFORMATION: Tamapin L17G

<400> SEQUENCE: 311

Ala Phe Cys Asn Leu Arg Arg Cys Glu Leu Ser Cys Arg Ser Leu Gly
  1               5                  10                  15

Gly Leu Gly Lys Cys Ile Gly Glu Glu Cys Lys Cys Val Pro Tyr
             20                  25                  30

<210> SEQ ID NO 312
<211> LENGTH: 31
<212> TYPE: PRT
<213> ORGANISM: Artificial Sequence
<220> FEATURE:
<223> OTHER INFORMATION: Tamapin L17H

<400> SEQUENCE: 312
```

Ala Phe Cys Asn Leu Arg Arg Cys Glu Leu Ser Cys Arg Ser Leu Gly
1               5                   10                  15

His Leu Gly Lys Cys Ile Gly Glu Glu Cys Lys Cys Val Pro Tyr
            20                  25                  30

<210> SEQ ID NO 313
<211> LENGTH: 31
<212> TYPE: PRT
<213> ORGANISM: Artificial Sequence
<220> FEATURE:
<223> OTHER INFORMATION: Tamapin L17I

<400> SEQUENCE: 313

Ala Phe Cys Asn Leu Arg Arg Cys Glu Leu Ser Cys Arg Ser Leu Gly
1               5                   10                  15

Ile Leu Gly Lys Cys Ile Gly Glu Glu Cys Lys Cys Val Pro Tyr
            20                  25                  30

<210> SEQ ID NO 314
<211> LENGTH: 31
<212> TYPE: PRT
<213> ORGANISM: Artificial Sequence
<220> FEATURE:
<223> OTHER INFORMATION: Tamapin L17K

<400> SEQUENCE: 314

Ala Phe Cys Asn Leu Arg Arg Cys Glu Leu Ser Cys Arg Ser Leu Gly
1               5                   10                  15

Lys Leu Gly Lys Cys Ile Gly Glu Glu Cys Lys Cys Val Pro Tyr
            20                  25                  30

<210> SEQ ID NO 315
<211> LENGTH: 31
<212> TYPE: PRT
<213> ORGANISM: Artificial Sequence
<220> FEATURE:
<223> OTHER INFORMATION: Tamapin L17M

<400> SEQUENCE: 315

Ala Phe Cys Asn Leu Arg Arg Cys Glu Leu Ser Cys Arg Ser Leu Gly
1               5                   10                  15

Met Leu Gly Lys Cys Ile Gly Glu Glu Cys Lys Cys Val Pro Tyr
            20                  25                  30

<210> SEQ ID NO 316
<211> LENGTH: 31
<212> TYPE: PRT
<213> ORGANISM: Artificial Sequence
<220> FEATURE:
<223> OTHER INFORMATION: Tamapin L17N

<400> SEQUENCE: 316

Ala Phe Cys Asn Leu Arg Arg Cys Glu Leu Ser Cys Arg Ser Leu Gly
1               5                   10                  15

Asn Leu Gly Lys Cys Ile Gly Glu Glu Cys Lys Cys Val Pro Tyr
            20                  25                  30

<210> SEQ ID NO 317
<211> LENGTH: 31
<212> TYPE: PRT
<213> ORGANISM: Artificial Sequence
<220> FEATURE:
<223> OTHER INFORMATION: Tamapin L17P

```
<400> SEQUENCE: 317

Ala Phe Cys Asn Leu Arg Arg Cys Glu Leu Ser Cys Arg Ser Leu Gly
1               5                   10                  15

Pro Leu Gly Lys Cys Ile Gly Glu Glu Cys Lys Cys Val Pro Tyr
            20                  25                  30

<210> SEQ ID NO 318
<211> LENGTH: 31
<212> TYPE: PRT
<213> ORGANISM: Artificial Sequence
<220> FEATURE:
<223> OTHER INFORMATION: Tamapin L17Q

<400> SEQUENCE: 318

Ala Phe Cys Asn Leu Arg Arg Cys Glu Leu Ser Cys Arg Ser Leu Gly
1               5                   10                  15

Gln Leu Gly Lys Cys Ile Gly Glu Glu Cys Lys Cys Val Pro Tyr
            20                  25                  30

<210> SEQ ID NO 319
<211> LENGTH: 31
<212> TYPE: PRT
<213> ORGANISM: Artificial Sequence
<220> FEATURE:
<223> OTHER INFORMATION: Tamapin L17R

<400> SEQUENCE: 319

Ala Phe Cys Asn Leu Arg Arg Cys Glu Leu Ser Cys Arg Ser Leu Gly
1               5                   10                  15

Arg Leu Gly Lys Cys Ile Gly Glu Glu Cys Lys Cys Val Pro Tyr
            20                  25                  30

<210> SEQ ID NO 320
<211> LENGTH: 31
<212> TYPE: PRT
<213> ORGANISM: Artificial Sequence
<220> FEATURE:
<223> OTHER INFORMATION: Tamapin L17S

<400> SEQUENCE: 320

Ala Phe Cys Asn Leu Arg Arg Cys Glu Leu Ser Cys Arg Ser Leu Gly
1               5                   10                  15

Ser Leu Gly Lys Cys Ile Gly Glu Glu Cys Lys Cys Val Pro Tyr
            20                  25                  30

<210> SEQ ID NO 321
<211> LENGTH: 31
<212> TYPE: PRT
<213> ORGANISM: Artificial Sequence
<220> FEATURE:
<223> OTHER INFORMATION: Tamapin L17T

<400> SEQUENCE: 321

Ala Phe Cys Asn Leu Arg Arg Cys Glu Leu Ser Cys Arg Ser Leu Gly
1               5                   10                  15

Thr Leu Gly Lys Cys Ile Gly Glu Glu Cys Lys Cys Val Pro Tyr
            20                  25                  30

<210> SEQ ID NO 322
<211> LENGTH: 31
<212> TYPE: PRT
<213> ORGANISM: Artificial Sequence
<220> FEATURE:
<223> OTHER INFORMATION: Tamapin L17V
```

```
<400> SEQUENCE: 322

Ala Phe Cys Asn Leu Arg Arg Cys Glu Leu Ser Cys Arg Ser Leu Gly
1               5                   10                  15

Val Leu Gly Lys Cys Ile Gly Glu Glu Cys Lys Cys Val Pro Tyr
            20                  25                  30

<210> SEQ ID NO 323
<211> LENGTH: 31
<212> TYPE: PRT
<213> ORGANISM: Artificial Sequence
<220> FEATURE:
<223> OTHER INFORMATION: Tamapin L17W

<400> SEQUENCE: 323

Ala Phe Cys Asn Leu Arg Arg Cys Glu Leu Ser Cys Arg Ser Leu Gly
1               5                   10                  15

Trp Leu Gly Lys Cys Ile Gly Glu Glu Cys Lys Cys Val Pro Tyr
            20                  25                  30

<210> SEQ ID NO 324
<211> LENGTH: 31
<212> TYPE: PRT
<213> ORGANISM: Artificial Sequence
<220> FEATURE:
<223> OTHER INFORMATION: Tamapin L17Y

<400> SEQUENCE: 324

Ala Phe Cys Asn Leu Arg Arg Cys Glu Leu Ser Cys Arg Ser Leu Gly
1               5                   10                  15

Tyr Leu Gly Lys Cys Ile Gly Glu Glu Cys Lys Cys Val Pro Tyr
            20                  25                  30

<210> SEQ ID NO 325
<211> LENGTH: 31
<212> TYPE: PRT
<213> ORGANISM: Artificial Sequence
<220> FEATURE:
<223> OTHER INFORMATION: Tamapin L18A

<400> SEQUENCE: 325

Ala Phe Cys Asn Leu Arg Arg Cys Glu Leu Ser Cys Arg Ser Leu Gly
1               5                   10                  15

Leu Ala Gly Lys Cys Ile Gly Glu Glu Cys Lys Cys Val Pro Tyr
            20                  25                  30

<210> SEQ ID NO 326
<211> LENGTH: 31
<212> TYPE: PRT
<213> ORGANISM: Artificial Sequence
<220> FEATURE:
<223> OTHER INFORMATION: Tamapin L18C

<400> SEQUENCE: 326

Ala Phe Cys Asn Leu Arg Arg Cys Glu Leu Ser Cys Arg Ser Leu Gly
1               5                   10                  15

Leu Cys Gly Lys Cys Ile Gly Glu Glu Cys Lys Cys Val Pro Tyr
            20                  25                  30

<210> SEQ ID NO 327
<211> LENGTH: 31
<212> TYPE: PRT
<213> ORGANISM: Artificial Sequence
<220> FEATURE:
```

<223> OTHER INFORMATION: Tamapin L18D

<400> SEQUENCE: 327

Ala Phe Cys Asn Leu Arg Arg Cys Glu Leu Ser Cys Arg Ser Leu Gly
1               5                   10                  15

Leu Asp Gly Lys Cys Ile Gly Glu Glu Cys Lys Cys Val Pro Tyr
            20                  25                  30

<210> SEQ ID NO 328
<211> LENGTH: 31
<212> TYPE: PRT
<213> ORGANISM: Artificial Sequence
<220> FEATURE:
<223> OTHER INFORMATION: Tamapin L18E

<400> SEQUENCE: 328

Ala Phe Cys Asn Leu Arg Arg Cys Glu Leu Ser Cys Arg Ser Leu Gly
1               5                   10                  15

Leu Glu Gly Lys Cys Ile Gly Glu Glu Cys Lys Cys Val Pro Tyr
            20                  25                  30

<210> SEQ ID NO 329
<211> LENGTH: 31
<212> TYPE: PRT
<213> ORGANISM: Artificial Sequence
<220> FEATURE:
<223> OTHER INFORMATION: Tamapin L18F

<400> SEQUENCE: 329

Ala Phe Cys Asn Leu Arg Arg Cys Glu Leu Ser Cys Arg Ser Leu Gly
1               5                   10                  15

Leu Phe Gly Lys Cys Ile Gly Glu Glu Cys Lys Cys Val Pro Tyr
            20                  25                  30

<210> SEQ ID NO 330
<211> LENGTH: 31
<212> TYPE: PRT
<213> ORGANISM: Artificial Sequence
<220> FEATURE:
<223> OTHER INFORMATION: Tamapin L18G

<400> SEQUENCE: 330

Ala Phe Cys Asn Leu Arg Arg Cys Glu Leu Ser Cys Arg Ser Leu Gly
1               5                   10                  15

Leu Gly Gly Lys Cys Ile Gly Glu Glu Cys Lys Cys Val Pro Tyr
            20                  25                  30

<210> SEQ ID NO 331
<211> LENGTH: 31
<212> TYPE: PRT
<213> ORGANISM: Artificial Sequence
<220> FEATURE:
<223> OTHER INFORMATION: Tamapin L18H

<400> SEQUENCE: 331

Ala Phe Cys Asn Leu Arg Arg Cys Glu Leu Ser Cys Arg Ser Leu Gly
1               5                   10                  15

Leu His Gly Lys Cys Ile Gly Glu Glu Cys Lys Cys Val Pro Tyr
            20                  25                  30

<210> SEQ ID NO 332
<211> LENGTH: 31
<212> TYPE: PRT
<213> ORGANISM: Artificial Sequence
<220> FEATURE:
<223> OTHER INFORMATION: Tamapin L18I

<400> SEQUENCE: 332

Ala Phe Cys Asn Leu Arg Arg Cys Glu Leu Ser Cys Arg Ser Leu Gly
1               5                   10                  15
Leu Ile Gly Lys Cys Ile Gly Glu Glu Cys Lys Cys Val Pro Tyr
            20                  25                  30

<210> SEQ ID NO 333
<211> LENGTH: 31
<212> TYPE: PRT
<213> ORGANISM: Artificial Sequence
<220> FEATURE:
<223> OTHER INFORMATION: Tamapin L18K

<400> SEQUENCE: 333

Ala Phe Cys Asn Leu Arg Arg Cys Glu Leu Ser Cys Arg Ser Leu Gly
1               5                   10                  15
Leu Lys Gly Lys Cys Ile Gly Glu Glu Cys Lys Cys Val Pro Tyr
            20                  25                  30

<210> SEQ ID NO 334
<211> LENGTH: 31
<212> TYPE: PRT
<213> ORGANISM: Artificial Sequence
<220> FEATURE:
<223> OTHER INFORMATION: Tamapin L18M

<400> SEQUENCE: 334

Ala Phe Cys Asn Leu Arg Arg Cys Glu Leu Ser Cys Arg Ser Leu Gly
1               5                   10                  15
Leu Met Gly Lys Cys Ile Gly Glu Glu Cys Lys Cys Val Pro Tyr
            20                  25                  30

<210> SEQ ID NO 335
<211> LENGTH: 31
<212> TYPE: PRT
<213> ORGANISM: Artificial Sequence
<220> FEATURE:
<223> OTHER INFORMATION: Tamapin L18N

<400> SEQUENCE: 335

Ala Phe Cys Asn Leu Arg Arg Cys Glu Leu Ser Cys Arg Ser Leu Gly
1               5                   10                  15
Leu Asn Gly Lys Cys Ile Gly Glu Glu Cys Lys Cys Val Pro Tyr
            20                  25                  30

<210> SEQ ID NO 336
<211> LENGTH: 31
<212> TYPE: PRT
<213> ORGANISM: Artificial Sequence
<220> FEATURE:
<223> OTHER INFORMATION: Tamapin L18P

<400> SEQUENCE: 336

Ala Phe Cys Asn Leu Arg Arg Cys Glu Leu Ser Cys Arg Ser Leu Gly
1               5                   10                  15
Leu Pro Gly Lys Cys Ile Gly Glu Glu Cys Lys Cys Val Pro Tyr
            20                  25                  30

<210> SEQ ID NO 337
<211> LENGTH: 31
<212> TYPE: PRT

```
<213> ORGANISM: Artificial Sequence
<220> FEATURE:
<223> OTHER INFORMATION: Tamapin L18Q

<400> SEQUENCE: 337

Ala Phe Cys Asn Leu Arg Arg Cys Glu Leu Ser Cys Arg Ser Leu Gly
1               5                   10                  15

Leu Gln Gly Lys Cys Ile Gly Glu Glu Cys Lys Cys Val Pro Tyr
            20                  25                  30

<210> SEQ ID NO 338
<211> LENGTH: 31
<212> TYPE: PRT
<213> ORGANISM: Artificial Sequence
<220> FEATURE:
<223> OTHER INFORMATION: Tamapin L18R

<400> SEQUENCE: 338

Ala Phe Cys Asn Leu Arg Arg Cys Glu Leu Ser Cys Arg Ser Leu Gly
1               5                   10                  15

Leu Arg Gly Lys Cys Ile Gly Glu Glu Cys Lys Cys Val Pro Tyr
            20                  25                  30

<210> SEQ ID NO 339
<211> LENGTH: 31
<212> TYPE: PRT
<213> ORGANISM: Artificial Sequence
<220> FEATURE:
<223> OTHER INFORMATION: Tamapin L18S

<400> SEQUENCE: 339

Ala Phe Cys Asn Leu Arg Arg Cys Glu Leu Ser Cys Arg Ser Leu Gly
1               5                   10                  15

Leu Ser Gly Lys Cys Ile Gly Glu Glu Cys Lys Cys Val Pro Tyr
            20                  25                  30

<210> SEQ ID NO 340
<211> LENGTH: 31
<212> TYPE: PRT
<213> ORGANISM: Artificial Sequence
<220> FEATURE:
<223> OTHER INFORMATION: Tamapin L18T

<400> SEQUENCE: 340

Ala Phe Cys Asn Leu Arg Arg Cys Glu Leu Ser Cys Arg Ser Leu Gly
1               5                   10                  15

Leu Thr Gly Lys Cys Ile Gly Glu Glu Cys Lys Cys Val Pro Tyr
            20                  25                  30

<210> SEQ ID NO 341
<211> LENGTH: 31
<212> TYPE: PRT
<213> ORGANISM: Artificial Sequence
<220> FEATURE:
<223> OTHER INFORMATION: Tamapin L18V

<400> SEQUENCE: 341

Ala Phe Cys Asn Leu Arg Arg Cys Glu Leu Ser Cys Arg Ser Leu Gly
1               5                   10                  15

Leu Val Gly Lys Cys Ile Gly Glu Glu Cys Lys Cys Val Pro Tyr
            20                  25                  30

<210> SEQ ID NO 342
<211> LENGTH: 31
```

```
<212> TYPE: PRT
<213> ORGANISM: Artificial Sequence
<220> FEATURE:
<223> OTHER INFORMATION: Tamapin L18W

<400> SEQUENCE: 342

Ala Phe Cys Asn Leu Arg Arg Cys Glu Leu Ser Cys Arg Ser Leu Gly
1               5                   10                  15
Leu Trp Gly Lys Cys Ile Gly Glu Glu Cys Lys Cys Val Pro Tyr
            20                  25                  30

<210> SEQ ID NO 343
<211> LENGTH: 31
<212> TYPE: PRT
<213> ORGANISM: Artificial Sequence
<220> FEATURE:
<223> OTHER INFORMATION: Tamapin L18Y

<400> SEQUENCE: 343

Ala Phe Cys Asn Leu Arg Arg Cys Glu Leu Ser Cys Arg Ser Leu Gly
1               5                   10                  15
Leu Tyr Gly Lys Cys Ile Gly Glu Glu Cys Lys Cys Val Pro Tyr
            20                  25                  30

<210> SEQ ID NO 344
<211> LENGTH: 31
<212> TYPE: PRT
<213> ORGANISM: Artificial Sequence
<220> FEATURE:
<223> OTHER INFORMATION: Tamapin G19A

<400> SEQUENCE: 344

Ala Phe Cys Asn Leu Arg Arg Cys Glu Leu Ser Cys Arg Ser Leu Gly
1               5                   10                  15
Leu Leu Ala Lys Cys Ile Gly Glu Glu Cys Lys Cys Val Pro Tyr
            20                  25                  30

<210> SEQ ID NO 345
<211> LENGTH: 31
<212> TYPE: PRT
<213> ORGANISM: Artificial Sequence
<220> FEATURE:
<223> OTHER INFORMATION: Tamapin G19C

<400> SEQUENCE: 345

Ala Phe Cys Asn Leu Arg Arg Cys Glu Leu Ser Cys Arg Ser Leu Gly
1               5                   10                  15
Leu Leu Cys Lys Cys Ile Gly Glu Glu Cys Lys Cys Val Pro Tyr
            20                  25                  30

<210> SEQ ID NO 346
<211> LENGTH: 31
<212> TYPE: PRT
<213> ORGANISM: Artificial Sequence
<220> FEATURE:
<223> OTHER INFORMATION: Tamapin G19D

<400> SEQUENCE: 346

Ala Phe Cys Asn Leu Arg Arg Cys Glu Leu Ser Cys Arg Ser Leu Gly
1               5                   10                  15
Leu Leu Asp Lys Cys Ile Gly Glu Glu Cys Lys Cys Val Pro Tyr
            20                  25                  30

<210> SEQ ID NO 347
```

<211> LENGTH: 31
<212> TYPE: PRT
<213> ORGANISM: Artificial Sequence
<220> FEATURE:
<223> OTHER INFORMATION: Tamapin G19E

<400> SEQUENCE: 347

Ala Phe Cys Asn Leu Arg Arg Cys Glu Leu Ser Cys Arg Ser Leu Gly
1               5                   10                  15

Leu Leu Glu Lys Cys Ile Gly Glu Glu Cys Lys Cys Val Pro Tyr
            20                  25                  30

<210> SEQ ID NO 348
<211> LENGTH: 31
<212> TYPE: PRT
<213> ORGANISM: Artificial Sequence
<220> FEATURE:
<223> OTHER INFORMATION: Tamapin G19F

<400> SEQUENCE: 348

Ala Phe Cys Asn Leu Arg Arg Cys Glu Leu Ser Cys Arg Ser Leu Gly
1               5                   10                  15

Leu Leu Phe Lys Cys Ile Gly Glu Glu Cys Lys Cys Val Pro Tyr
            20                  25                  30

<210> SEQ ID NO 349
<211> LENGTH: 31
<212> TYPE: PRT
<213> ORGANISM: Artificial Sequence
<220> FEATURE:
<223> OTHER INFORMATION: Tamapin G19H

<400> SEQUENCE: 349

Ala Phe Cys Asn Leu Arg Arg Cys Glu Leu Ser Cys Arg Ser Leu Gly
1               5                   10                  15

Leu Leu His Lys Cys Ile Gly Glu Glu Cys Lys Cys Val Pro Tyr
            20                  25                  30

<210> SEQ ID NO 350
<211> LENGTH: 31
<212> TYPE: PRT
<213> ORGANISM: Artificial Sequence
<220> FEATURE:
<223> OTHER INFORMATION: Tamapin G19I

<400> SEQUENCE: 350

Ala Phe Cys Asn Leu Arg Arg Cys Glu Leu Ser Cys Arg Ser Leu Gly
1               5                   10                  15

Leu Leu Ile Lys Cys Ile Gly Glu Glu Cys Lys Cys Val Pro Tyr
            20                  25                  30

<210> SEQ ID NO 351
<211> LENGTH: 31
<212> TYPE: PRT
<213> ORGANISM: Artificial Sequence
<220> FEATURE:
<223> OTHER INFORMATION: Tamapin G19K

<400> SEQUENCE: 351

Ala Phe Cys Asn Leu Arg Arg Cys Glu Leu Ser Cys Arg Ser Leu Gly
1               5                   10                  15

Leu Leu Lys Lys Cys Ile Gly Glu Glu Cys Lys Cys Val Pro Tyr
            20                  25                  30

```
<210> SEQ ID NO 352
<211> LENGTH: 31
<212> TYPE: PRT
<213> ORGANISM: Artificial Sequence
<220> FEATURE:
<223> OTHER INFORMATION: Tamapin G19L

<400> SEQUENCE: 352

Ala Phe Cys Asn Leu Arg Arg Cys Glu Leu Ser Cys Arg Ser Leu Gly
1               5                   10                  15

Leu Leu Leu Lys Cys Ile Gly Glu Glu Cys Lys Cys Val Pro Tyr
            20                  25                  30

<210> SEQ ID NO 353
<211> LENGTH: 31
<212> TYPE: PRT
<213> ORGANISM: Artificial Sequence
<220> FEATURE:
<223> OTHER INFORMATION: Tamapin G19M

<400> SEQUENCE: 353

Ala Phe Cys Asn Leu Arg Arg Cys Glu Leu Ser Cys Arg Ser Leu Gly
1               5                   10                  15

Leu Leu Met Lys Cys Ile Gly Glu Glu Cys Lys Cys Val Pro Tyr
            20                  25                  30

<210> SEQ ID NO 354
<211> LENGTH: 31
<212> TYPE: PRT
<213> ORGANISM: Artificial Sequence
<220> FEATURE:
<223> OTHER INFORMATION: Tamapin G19N

<400> SEQUENCE: 354

Ala Phe Cys Asn Leu Arg Arg Cys Glu Leu Ser Cys Arg Ser Leu Gly
1               5                   10                  15

Leu Leu Asn Lys Cys Ile Gly Glu Glu Cys Lys Cys Val Pro Tyr
            20                  25                  30

<210> SEQ ID NO 355
<211> LENGTH: 31
<212> TYPE: PRT
<213> ORGANISM: Artificial Sequence
<220> FEATURE:
<223> OTHER INFORMATION: Tamapin G19P

<400> SEQUENCE: 355

Ala Phe Cys Asn Leu Arg Arg Cys Glu Leu Ser Cys Arg Ser Leu Gly
1               5                   10                  15

Leu Leu Pro Lys Cys Ile Gly Glu Glu Cys Lys Cys Val Pro Tyr
            20                  25                  30

<210> SEQ ID NO 356
<211> LENGTH: 31
<212> TYPE: PRT
<213> ORGANISM: Artificial Sequence
<220> FEATURE:
<223> OTHER INFORMATION: Tamapin G19Q

<400> SEQUENCE: 356

Ala Phe Cys Asn Leu Arg Arg Cys Glu Leu Ser Cys Arg Ser Leu Gly
1               5                   10                  15

Leu Leu Gln Lys Cys Ile Gly Glu Glu Cys Lys Cys Val Pro Tyr
            20                  25                  30
```

<210> SEQ ID NO 357
<211> LENGTH: 31
<212> TYPE: PRT
<213> ORGANISM: Artificial Sequence
<220> FEATURE:
<223> OTHER INFORMATION: Tamapin G19R

<400> SEQUENCE: 357

Ala Phe Cys Asn Leu Arg Arg Cys Glu Leu Ser Cys Arg Ser Leu Gly
1               5                   10                  15

Leu Leu Arg Lys Cys Ile Gly Glu Glu Cys Lys Cys Val Pro Tyr
            20                  25                  30

<210> SEQ ID NO 358
<211> LENGTH: 31
<212> TYPE: PRT
<213> ORGANISM: Artificial Sequence
<220> FEATURE:
<223> OTHER INFORMATION: Tamapin G19S

<400> SEQUENCE: 358

Ala Phe Cys Asn Leu Arg Arg Cys Glu Leu Ser Cys Arg Ser Leu Gly
1               5                   10                  15

Leu Leu Ser Lys Cys Ile Gly Glu Glu Cys Lys Cys Val Pro Tyr
            20                  25                  30

<210> SEQ ID NO 359
<211> LENGTH: 31
<212> TYPE: PRT
<213> ORGANISM: Artificial Sequence
<220> FEATURE:
<223> OTHER INFORMATION: Tamapin G19T

<400> SEQUENCE: 359

Ala Phe Cys Asn Leu Arg Arg Cys Glu Leu Ser Cys Arg Ser Leu Gly
1               5                   10                  15

Leu Leu Thr Lys Cys Ile Gly Glu Glu Cys Lys Cys Val Pro Tyr
            20                  25                  30

<210> SEQ ID NO 360
<211> LENGTH: 31
<212> TYPE: PRT
<213> ORGANISM: Artificial Sequence
<220> FEATURE:
<223> OTHER INFORMATION: Tamapin G19V

<400> SEQUENCE: 360

Ala Phe Cys Asn Leu Arg Arg Cys Glu Leu Ser Cys Arg Ser Leu Gly
1               5                   10                  15

Leu Leu Val Lys Cys Ile Gly Glu Glu Cys Lys Cys Val Pro Tyr
            20                  25                  30

<210> SEQ ID NO 361
<211> LENGTH: 31
<212> TYPE: PRT
<213> ORGANISM: Artificial Sequence
<220> FEATURE:
<223> OTHER INFORMATION: Tamapin G19W

<400> SEQUENCE: 361

Ala Phe Cys Asn Leu Arg Arg Cys Glu Leu Ser Cys Arg Ser Leu Gly
1               5                   10                  15

Leu Leu Trp Lys Cys Ile Gly Glu Glu Cys Lys Cys Val Pro Tyr
            20                  25                  30

<210> SEQ ID NO 362
<211> LENGTH: 31
<212> TYPE: PRT
<213> ORGANISM: Artificial Sequence
<220> FEATURE:
<223> OTHER INFORMATION: Tamapin G19Y

<400> SEQUENCE: 362

Ala Phe Cys Asn Leu Arg Arg Cys Glu Leu Ser Cys Arg Ser Leu Gly
1               5                   10                  15

Leu Leu Tyr Lys Cys Ile Gly Glu Glu Cys Lys Cys Val Pro Tyr
            20                  25                  30

<210> SEQ ID NO 363
<211> LENGTH: 31
<212> TYPE: PRT
<213> ORGANISM: Artificial Sequence
<220> FEATURE:
<223> OTHER INFORMATION: Tamapin K20A

<400> SEQUENCE: 363

Ala Phe Cys Asn Leu Arg Arg Cys Glu Leu Ser Cys Arg Ser Leu Gly
1               5                   10                  15

Leu Leu Gly Ala Cys Ile Gly Glu Glu Cys Lys Cys Val Pro Tyr
            20                  25                  30

<210> SEQ ID NO 364
<211> LENGTH: 31
<212> TYPE: PRT
<213> ORGANISM: Artificial Sequence
<220> FEATURE:
<223> OTHER INFORMATION: Tamapin K20C

<400> SEQUENCE: 364

Ala Phe Cys Asn Leu Arg Arg Cys Glu Leu Ser Cys Arg Ser Leu Gly
1               5                   10                  15

Leu Leu Gly Cys Cys Ile Gly Glu Glu Cys Lys Cys Val Pro Tyr
            20                  25                  30

<210> SEQ ID NO 365
<211> LENGTH: 31
<212> TYPE: PRT
<213> ORGANISM: Artificial Sequence
<220> FEATURE:
<223> OTHER INFORMATION: Tamapin K20D

<400> SEQUENCE: 365

Ala Phe Cys Asn Leu Arg Arg Cys Glu Leu Ser Cys Arg Ser Leu Gly
1               5                   10                  15

Leu Leu Gly Asp Cys Ile Gly Glu Glu Cys Lys Cys Val Pro Tyr
            20                  25                  30

<210> SEQ ID NO 366
<211> LENGTH: 31
<212> TYPE: PRT
<213> ORGANISM: Artificial Sequence
<220> FEATURE:
<223> OTHER INFORMATION: Tamapin K20E

<400> SEQUENCE: 366

Ala Phe Cys Asn Leu Arg Arg Cys Glu Leu Ser Cys Arg Ser Leu Gly
1               5                   10                  15

Leu Leu Gly Glu Cys Ile Gly Glu Glu Cys Lys Cys Val Pro Tyr

-continued

```
                20                  25                  30

<210> SEQ ID NO 367
<211> LENGTH: 31
<212> TYPE: PRT
<213> ORGANISM: Artificial Sequence
<220> FEATURE:
<223> OTHER INFORMATION: Tamapin K20F

<400> SEQUENCE: 367

Ala Phe Cys Asn Leu Arg Arg Cys Glu Leu Ser Cys Arg Ser Leu Gly
1               5                   10                  15

Leu Leu Gly Phe Cys Ile Gly Glu Glu Cys Lys Cys Val Pro Tyr
            20                  25                  30

<210> SEQ ID NO 368
<211> LENGTH: 31
<212> TYPE: PRT
<213> ORGANISM: Artificial Sequence
<220> FEATURE:
<223> OTHER INFORMATION: Tamapin K20G

<400> SEQUENCE: 368

Ala Phe Cys Asn Leu Arg Arg Cys Glu Leu Ser Cys Arg Ser Leu Gly
1               5                   10                  15

Leu Leu Gly Gly Cys Ile Gly Glu Glu Cys Lys Cys Val Pro Tyr
            20                  25                  30

<210> SEQ ID NO 369
<211> LENGTH: 31
<212> TYPE: PRT
<213> ORGANISM: Artificial Sequence
<220> FEATURE:
<223> OTHER INFORMATION: Tamapin K20H

<400> SEQUENCE: 369

Ala Phe Cys Asn Leu Arg Arg Cys Glu Leu Ser Cys Arg Ser Leu Gly
1               5                   10                  15

Leu Leu Gly His Cys Ile Gly Glu Glu Cys Lys Cys Val Pro Tyr
            20                  25                  30

<210> SEQ ID NO 370
<211> LENGTH: 31
<212> TYPE: PRT
<213> ORGANISM: Artificial Sequence
<220> FEATURE:
<223> OTHER INFORMATION: Tamapin K20I

<400> SEQUENCE: 370

Ala Phe Cys Asn Leu Arg Arg Cys Glu Leu Ser Cys Arg Ser Leu Gly
1               5                   10                  15

Leu Leu Gly Ile Cys Ile Gly Glu Glu Cys Lys Cys Val Pro Tyr
            20                  25                  30

<210> SEQ ID NO 371
<211> LENGTH: 31
<212> TYPE: PRT
<213> ORGANISM: Artificial Sequence
<220> FEATURE:
<223> OTHER INFORMATION: Tamapin K20L

<400> SEQUENCE: 371

Ala Phe Cys Asn Leu Arg Arg Cys Glu Leu Ser Cys Arg Ser Leu Gly
1               5                   10                  15
```

```
Leu Leu Gly Leu Cys Ile Gly Glu Glu Cys Lys Cys Val Pro Tyr
        20                  25                  30
```

<210> SEQ ID NO 372
<211> LENGTH: 31
<212> TYPE: PRT
<213> ORGANISM: Artificial Sequence
<220> FEATURE:
<223> OTHER INFORMATION: Tamapin K20M

<400> SEQUENCE: 372

```
Ala Phe Cys Asn Leu Arg Arg Cys Glu Leu Ser Cys Arg Ser Leu Gly
1               5                   10                  15

Leu Leu Gly Met Cys Ile Gly Glu Glu Cys Lys Cys Val Pro Tyr
        20                  25                  30
```

<210> SEQ ID NO 373
<211> LENGTH: 31
<212> TYPE: PRT
<213> ORGANISM: Artificial Sequence
<220> FEATURE:
<223> OTHER INFORMATION: Tamapin K20N

<400> SEQUENCE: 373

```
Ala Phe Cys Asn Leu Arg Arg Cys Glu Leu Ser Cys Arg Ser Leu Gly
1               5                   10                  15

Leu Leu Gly Asn Cys Ile Gly Glu Glu Cys Lys Cys Val Pro Tyr
        20                  25                  30
```

<210> SEQ ID NO 374
<211> LENGTH: 31
<212> TYPE: PRT
<213> ORGANISM: Artificial Sequence
<220> FEATURE:
<223> OTHER INFORMATION: Tamapin K20P

<400> SEQUENCE: 374

```
Ala Phe Cys Asn Leu Arg Arg Cys Glu Leu Ser Cys Arg Ser Leu Gly
1               5                   10                  15

Leu Leu Gly Pro Cys Ile Gly Glu Glu Cys Lys Cys Val Pro Tyr
        20                  25                  30
```

<210> SEQ ID NO 375
<211> LENGTH: 31
<212> TYPE: PRT
<213> ORGANISM: Artificial Sequence
<220> FEATURE:
<223> OTHER INFORMATION: Tamapin K20Q

<400> SEQUENCE: 375

```
Ala Phe Cys Asn Leu Arg Arg Cys Glu Leu Ser Cys Arg Ser Leu Gly
1               5                   10                  15

Leu Leu Gly Gln Cys Ile Gly Glu Glu Cys Lys Cys Val Pro Tyr
        20                  25                  30
```

<210> SEQ ID NO 376
<211> LENGTH: 31
<212> TYPE: PRT
<213> ORGANISM: Artificial Sequence
<220> FEATURE:
<223> OTHER INFORMATION: Tamapin K20R

<400> SEQUENCE: 376

```
Ala Phe Cys Asn Leu Arg Arg Cys Glu Leu Ser Cys Arg Ser Leu Gly
1               5                   10                  15
```

Leu Leu Gly Arg Cys Ile Gly Glu Glu Cys Lys Cys Val Pro Tyr
            20                  25                  30

<210> SEQ ID NO 377
<211> LENGTH: 31
<212> TYPE: PRT
<213> ORGANISM: Artificial Sequence
<220> FEATURE:
<223> OTHER INFORMATION: Tamapin K20S

<400> SEQUENCE: 377

Ala Phe Cys Asn Leu Arg Arg Cys Glu Leu Ser Cys Arg Ser Leu Gly
1               5                   10                  15

Leu Leu Gly Ser Cys Ile Gly Glu Glu Cys Lys Cys Val Pro Tyr
            20                  25                  30

<210> SEQ ID NO 378
<211> LENGTH: 31
<212> TYPE: PRT
<213> ORGANISM: Artificial Sequence
<220> FEATURE:
<223> OTHER INFORMATION: Tamapin K20T

<400> SEQUENCE: 378

Ala Phe Cys Asn Leu Arg Arg Cys Glu Leu Ser Cys Arg Ser Leu Gly
1               5                   10                  15

Leu Leu Gly Thr Cys Ile Gly Glu Glu Cys Lys Cys Val Pro Tyr
            20                  25                  30

<210> SEQ ID NO 379
<211> LENGTH: 31
<212> TYPE: PRT
<213> ORGANISM: Artificial Sequence
<220> FEATURE:
<223> OTHER INFORMATION: Tamapin K20V

<400> SEQUENCE: 379

Ala Phe Cys Asn Leu Arg Arg Cys Glu Leu Ser Cys Arg Ser Leu Gly
1               5                   10                  15

Leu Leu Gly Val Cys Ile Gly Glu Glu Cys Lys Cys Val Pro Tyr
            20                  25                  30

<210> SEQ ID NO 380
<211> LENGTH: 31
<212> TYPE: PRT
<213> ORGANISM: Artificial Sequence
<220> FEATURE:
<223> OTHER INFORMATION: Tamapin K20W

<400> SEQUENCE: 380

Ala Phe Cys Asn Leu Arg Arg Cys Glu Leu Ser Cys Arg Ser Leu Gly
1               5                   10                  15

Leu Leu Gly Trp Cys Ile Gly Glu Glu Cys Lys Cys Val Pro Tyr
            20                  25                  30

<210> SEQ ID NO 381
<211> LENGTH: 31
<212> TYPE: PRT
<213> ORGANISM: Artificial Sequence
<220> FEATURE:
<223> OTHER INFORMATION: Tamapin K20Y

<400> SEQUENCE: 381

Ala Phe Cys Asn Leu Arg Arg Cys Glu Leu Ser Cys Arg Ser Leu Gly

```
                1               5                   10                  15
Leu Leu Gly Tyr Cys Ile Gly Glu Glu Cys Lys Cys Val Pro Tyr
                20                  25                  30
```

<210> SEQ ID NO 382
<211> LENGTH: 31
<212> TYPE: PRT
<213> ORGANISM: Artificial Sequence
<220> FEATURE:
<223> OTHER INFORMATION: Tamapin C21A

<400> SEQUENCE: 382

```
Ala Phe Cys Asn Leu Arg Arg Cys Glu Leu Ser Cys Arg Ser Leu Gly
1               5                   10                  15
Leu Leu Gly Lys Ala Ile Gly Glu Glu Cys Lys Cys Val Pro Tyr
                20                  25                  30
```

<210> SEQ ID NO 383
<211> LENGTH: 31
<212> TYPE: PRT
<213> ORGANISM: Artificial Sequence
<220> FEATURE:
<223> OTHER INFORMATION: Tamapin C21D

<400> SEQUENCE: 383

```
Ala Phe Cys Asn Leu Arg Arg Cys Glu Leu Ser Cys Arg Ser Leu Gly
1               5                   10                  15
Leu Leu Gly Lys Asp Ile Gly Glu Glu Cys Lys Cys Val Pro Tyr
                20                  25                  30
```

<210> SEQ ID NO 384
<211> LENGTH: 31
<212> TYPE: PRT
<213> ORGANISM: Artificial Sequence
<220> FEATURE:
<223> OTHER INFORMATION: Tamapin C21E

<400> SEQUENCE: 384

```
Ala Phe Cys Asn Leu Arg Arg Cys Glu Leu Ser Cys Arg Ser Leu Gly
1               5                   10                  15
Leu Leu Gly Lys Glu Ile Gly Glu Glu Cys Lys Cys Val Pro Tyr
                20                  25                  30
```

<210> SEQ ID NO 385
<211> LENGTH: 31
<212> TYPE: PRT
<213> ORGANISM: Artificial Sequence
<220> FEATURE:
<223> OTHER INFORMATION: Tamapin C21F

<400> SEQUENCE: 385

```
Ala Phe Cys Asn Leu Arg Arg Cys Glu Leu Ser Cys Arg Ser Leu Gly
1               5                   10                  15
Leu Leu Gly Lys Phe Ile Gly Glu Glu Cys Lys Cys Val Pro Tyr
                20                  25                  30
```

<210> SEQ ID NO 386
<211> LENGTH: 31
<212> TYPE: PRT
<213> ORGANISM: Artificial Sequence
<220> FEATURE:
<223> OTHER INFORMATION: Tamapin C21G

<400> SEQUENCE: 386

```
Ala Phe Cys Asn Leu Arg Arg Cys Glu Leu Ser Cys Arg Ser Leu Gly
1               5                   10                  15

Leu Leu Gly Lys Gly Ile Gly Glu Glu Cys Lys Cys Val Pro Tyr
            20                  25                  30
```

<210> SEQ ID NO 387
<211> LENGTH: 31
<212> TYPE: PRT
<213> ORGANISM: Artificial Sequence
<220> FEATURE:
<223> OTHER INFORMATION: Tamapin C21H

<400> SEQUENCE: 387

```
Ala Phe Cys Asn Leu Arg Arg Cys Glu Leu Ser Cys Arg Ser Leu Gly
1               5                   10                  15

Leu Leu Gly Lys His Ile Gly Glu Glu Cys Lys Cys Val Pro Tyr
            20                  25                  30
```

<210> SEQ ID NO 388
<211> LENGTH: 31
<212> TYPE: PRT
<213> ORGANISM: Artificial Sequence
<220> FEATURE:
<223> OTHER INFORMATION: Tamapin C21I

<400> SEQUENCE: 388

```
Ala Phe Cys Asn Leu Arg Arg Cys Glu Leu Ser Cys Arg Ser Leu Gly
1               5                   10                  15

Leu Leu Gly Lys Ile Ile Gly Glu Glu Cys Lys Cys Val Pro Tyr
            20                  25                  30
```

<210> SEQ ID NO 389
<211> LENGTH: 31
<212> TYPE: PRT
<213> ORGANISM: Artificial Sequence
<220> FEATURE:
<223> OTHER INFORMATION: Tamapin C21K

<400> SEQUENCE: 389

```
Ala Phe Cys Asn Leu Arg Arg Cys Glu Leu Ser Cys Arg Ser Leu Gly
1               5                   10                  15

Leu Leu Gly Lys Lys Ile Gly Glu Glu Cys Lys Cys Val Pro Tyr
            20                  25                  30
```

<210> SEQ ID NO 390
<211> LENGTH: 31
<212> TYPE: PRT
<213> ORGANISM: Artificial Sequence
<220> FEATURE:
<223> OTHER INFORMATION: Tamapin C21L

<400> SEQUENCE: 390

```
Ala Phe Cys Asn Leu Arg Arg Cys Glu Leu Ser Cys Arg Ser Leu Gly
1               5                   10                  15

Leu Leu Gly Lys Leu Ile Gly Glu Glu Cys Lys Cys Val Pro Tyr
            20                  25                  30
```

<210> SEQ ID NO 391
<211> LENGTH: 31
<212> TYPE: PRT
<213> ORGANISM: Artificial Sequence
<220> FEATURE:
<223> OTHER INFORMATION: Tamapin C21M

<400> SEQUENCE: 391

```
Ala Phe Cys Asn Leu Arg Arg Cys Glu Leu Ser Cys Arg Ser Leu Gly
1               5                   10                  15

Leu Leu Gly Lys Met Ile Gly Glu Glu Cys Lys Cys Val Pro Tyr
                20                  25                  30

<210> SEQ ID NO 392
<211> LENGTH: 31
<212> TYPE: PRT
<213> ORGANISM: Artificial Sequence
<220> FEATURE:
<223> OTHER INFORMATION: Tamapin C21N

<400> SEQUENCE: 392

Ala Phe Cys Asn Leu Arg Arg Cys Glu Leu Ser Cys Arg Ser Leu Gly
1               5                   10                  15

Leu Leu Gly Lys Asn Ile Gly Glu Glu Cys Lys Cys Val Pro Tyr
                20                  25                  30

<210> SEQ ID NO 393
<211> LENGTH: 31
<212> TYPE: PRT
<213> ORGANISM: Artificial Sequence
<220> FEATURE:
<223> OTHER INFORMATION: Tamapin C21P

<400> SEQUENCE: 393

Ala Phe Cys Asn Leu Arg Arg Cys Glu Leu Ser Cys Arg Ser Leu Gly
1               5                   10                  15

Leu Leu Gly Lys Pro Ile Gly Glu Glu Cys Lys Cys Val Pro Tyr
                20                  25                  30

<210> SEQ ID NO 394
<211> LENGTH: 31
<212> TYPE: PRT
<213> ORGANISM: Artificial Sequence
<220> FEATURE:
<223> OTHER INFORMATION: Tamapin C21Q

<400> SEQUENCE: 394

Ala Phe Cys Asn Leu Arg Arg Cys Glu Leu Ser Cys Arg Ser Leu Gly
1               5                   10                  15

Leu Leu Gly Lys Gln Ile Gly Glu Glu Cys Lys Cys Val Pro Tyr
                20                  25                  30

<210> SEQ ID NO 395
<211> LENGTH: 31
<212> TYPE: PRT
<213> ORGANISM: Artificial Sequence
<220> FEATURE:
<223> OTHER INFORMATION: Tamapin C21R

<400> SEQUENCE: 395

Ala Phe Cys Asn Leu Arg Arg Cys Glu Leu Ser Cys Arg Ser Leu Gly
1               5                   10                  15

Leu Leu Gly Lys Arg Ile Gly Glu Glu Cys Lys Cys Val Pro Tyr
                20                  25                  30

<210> SEQ ID NO 396
<211> LENGTH: 31
<212> TYPE: PRT
<213> ORGANISM: Artificial Sequence
<220> FEATURE:
<223> OTHER INFORMATION: Tamapin C21S
```

```
<400> SEQUENCE: 396

Ala Phe Cys Asn Leu Arg Arg Cys Glu Leu Ser Cys Arg Ser Leu Gly
1               5                   10                  15

Leu Leu Gly Lys Ser Ile Gly Glu Glu Cys Lys Cys Val Pro Tyr
            20                  25                  30

<210> SEQ ID NO 397
<211> LENGTH: 31
<212> TYPE: PRT
<213> ORGANISM: Artificial Sequence
<220> FEATURE:
<223> OTHER INFORMATION: Tamapin C21T

<400> SEQUENCE: 397

Ala Phe Cys Asn Leu Arg Arg Cys Glu Leu Ser Cys Arg Ser Leu Gly
1               5                   10                  15

Leu Leu Gly Lys Thr Ile Gly Glu Glu Cys Lys Cys Val Pro Tyr
            20                  25                  30

<210> SEQ ID NO 398
<211> LENGTH: 31
<212> TYPE: PRT
<213> ORGANISM: Artificial Sequence
<220> FEATURE:
<223> OTHER INFORMATION: Tamapin C21V

<400> SEQUENCE: 398

Ala Phe Cys Asn Leu Arg Arg Cys Glu Leu Ser Cys Arg Ser Leu Gly
1               5                   10                  15

Leu Leu Gly Lys Val Ile Gly Glu Glu Cys Lys Cys Val Pro Tyr
            20                  25                  30

<210> SEQ ID NO 399
<211> LENGTH: 31
<212> TYPE: PRT
<213> ORGANISM: Artificial Sequence
<220> FEATURE:
<223> OTHER INFORMATION: Tamapin C21W

<400> SEQUENCE: 399

Ala Phe Cys Asn Leu Arg Arg Cys Glu Leu Ser Cys Arg Ser Leu Gly
1               5                   10                  15

Leu Leu Gly Lys Trp Ile Gly Glu Glu Cys Lys Cys Val Pro Tyr
            20                  25                  30

<210> SEQ ID NO 400
<211> LENGTH: 31
<212> TYPE: PRT
<213> ORGANISM: Artificial Sequence
<220> FEATURE:
<223> OTHER INFORMATION: Tamapin C21Y

<400> SEQUENCE: 400

Ala Phe Cys Asn Leu Arg Arg Cys Glu Leu Ser Cys Arg Ser Leu Gly
1               5                   10                  15

Leu Leu Gly Lys Tyr Ile Gly Glu Glu Cys Lys Cys Val Pro Tyr
            20                  25                  30

<210> SEQ ID NO 401
<211> LENGTH: 31
<212> TYPE: PRT
<213> ORGANISM: Artificial Sequence
<220> FEATURE:
<223> OTHER INFORMATION: Tamapin I22A
```

```
<400> SEQUENCE: 401

Ala Phe Cys Asn Leu Arg Arg Cys Glu Leu Ser Cys Arg Ser Leu Gly
1               5                   10                  15

Leu Leu Gly Lys Cys Ala Gly Glu Glu Cys Lys Cys Val Pro Tyr
            20                  25                  30

<210> SEQ ID NO 402
<211> LENGTH: 31
<212> TYPE: PRT
<213> ORGANISM: Artificial Sequence
<220> FEATURE:
<223> OTHER INFORMATION: Tamapin I22C

<400> SEQUENCE: 402

Ala Phe Cys Asn Leu Arg Arg Cys Glu Leu Ser Cys Arg Ser Leu Gly
1               5                   10                  15

Leu Leu Gly Lys Cys Cys Gly Glu Glu Cys Lys Cys Val Pro Tyr
            20                  25                  30

<210> SEQ ID NO 403
<211> LENGTH: 31
<212> TYPE: PRT
<213> ORGANISM: Artificial Sequence
<220> FEATURE:
<223> OTHER INFORMATION: Tamapin I22D

<400> SEQUENCE: 403

Ala Phe Cys Asn Leu Arg Arg Cys Glu Leu Ser Cys Arg Ser Leu Gly
1               5                   10                  15

Leu Leu Gly Lys Cys Asp Gly Glu Glu Cys Lys Cys Val Pro Tyr
            20                  25                  30

<210> SEQ ID NO 404
<211> LENGTH: 31
<212> TYPE: PRT
<213> ORGANISM: Artificial Sequence
<220> FEATURE:
<223> OTHER INFORMATION: Tamapin I22E

<400> SEQUENCE: 404

Ala Phe Cys Asn Leu Arg Arg Cys Glu Leu Ser Cys Arg Ser Leu Gly
1               5                   10                  15

Leu Leu Gly Lys Cys Glu Gly Glu Glu Cys Lys Cys Val Pro Tyr
            20                  25                  30

<210> SEQ ID NO 405
<211> LENGTH: 31
<212> TYPE: PRT
<213> ORGANISM: Artificial Sequence
<220> FEATURE:
<223> OTHER INFORMATION: Tamapin I22F

<400> SEQUENCE: 405

Ala Phe Cys Asn Leu Arg Arg Cys Glu Leu Ser Cys Arg Ser Leu Gly
1               5                   10                  15

Leu Leu Gly Lys Cys Phe Gly Glu Glu Cys Lys Cys Val Pro Tyr
            20                  25                  30

<210> SEQ ID NO 406
<211> LENGTH: 31
<212> TYPE: PRT
<213> ORGANISM: Artificial Sequence
<220> FEATURE:
```

-continued

<223> OTHER INFORMATION: Tamapin I22G

<400> SEQUENCE: 406

Ala Phe Cys Asn Leu Arg Arg Cys Glu Leu Ser Cys Arg Ser Leu Gly
1               5                   10                  15

Leu Leu Gly Lys Cys Gly Gly Glu Glu Cys Lys Cys Val Pro Tyr
            20                  25                  30

<210> SEQ ID NO 407
<211> LENGTH: 31
<212> TYPE: PRT
<213> ORGANISM: Artificial Sequence
<220> FEATURE:
<223> OTHER INFORMATION: Tamapin I22H

<400> SEQUENCE: 407

Ala Phe Cys Asn Leu Arg Arg Cys Glu Leu Ser Cys Arg Ser Leu Gly
1               5                   10                  15

Leu Leu Gly Lys Cys His Gly Glu Glu Cys Lys Cys Val Pro Tyr
            20                  25                  30

<210> SEQ ID NO 408
<211> LENGTH: 31
<212> TYPE: PRT
<213> ORGANISM: Artificial Sequence
<220> FEATURE:
<223> OTHER INFORMATION: Tamapin I22K

<400> SEQUENCE: 408

Ala Phe Cys Asn Leu Arg Arg Cys Glu Leu Ser Cys Arg Ser Leu Gly
1               5                   10                  15

Leu Leu Gly Lys Cys Lys Gly Glu Glu Cys Lys Cys Val Pro Tyr
            20                  25                  30

<210> SEQ ID NO 409
<211> LENGTH: 31
<212> TYPE: PRT
<213> ORGANISM: Artificial Sequence
<220> FEATURE:
<223> OTHER INFORMATION: Tamapin I22L

<400> SEQUENCE: 409

Ala Phe Cys Asn Leu Arg Arg Cys Glu Leu Ser Cys Arg Ser Leu Gly
1               5                   10                  15

Leu Leu Gly Lys Cys Leu Gly Glu Glu Cys Lys Cys Val Pro Tyr
            20                  25                  30

<210> SEQ ID NO 410
<211> LENGTH: 31
<212> TYPE: PRT
<213> ORGANISM: Artificial Sequence
<220> FEATURE:
<223> OTHER INFORMATION: Tamapin I22M

<400> SEQUENCE: 410

Ala Phe Cys Asn Leu Arg Arg Cys Glu Leu Ser Cys Arg Ser Leu Gly
1               5                   10                  15

Leu Leu Gly Lys Cys Met Gly Glu Glu Cys Lys Cys Val Pro Tyr
            20                  25                  30

<210> SEQ ID NO 411
<211> LENGTH: 31
<212> TYPE: PRT
<213> ORGANISM: Artificial Sequence

```
<220> FEATURE:
<223> OTHER INFORMATION: Tamapin I22N

<400> SEQUENCE: 411

Ala Phe Cys Asn Leu Arg Arg Cys Glu Leu Ser Cys Arg Ser Leu Gly
1               5                   10                  15
Leu Leu Gly Lys Cys Asn Gly Glu Glu Cys Lys Cys Val Pro Tyr
            20                  25                  30

<210> SEQ ID NO 412
<211> LENGTH: 31
<212> TYPE: PRT
<213> ORGANISM: Artificial Sequence
<220> FEATURE:
<223> OTHER INFORMATION: Tamapin I22P

<400> SEQUENCE: 412

Ala Phe Cys Asn Leu Arg Arg Cys Glu Leu Ser Cys Arg Ser Leu Gly
1               5                   10                  15
Leu Leu Gly Lys Cys Pro Gly Glu Glu Cys Lys Cys Val Pro Tyr
            20                  25                  30

<210> SEQ ID NO 413
<211> LENGTH: 31
<212> TYPE: PRT
<213> ORGANISM: Artificial Sequence
<220> FEATURE:
<223> OTHER INFORMATION: Tamapin I22Q

<400> SEQUENCE: 413

Ala Phe Cys Asn Leu Arg Arg Cys Glu Leu Ser Cys Arg Ser Leu Gly
1               5                   10                  15
Leu Leu Gly Lys Cys Gln Gly Glu Glu Cys Lys Cys Val Pro Tyr
            20                  25                  30

<210> SEQ ID NO 414
<211> LENGTH: 31
<212> TYPE: PRT
<213> ORGANISM: Artificial Sequence
<220> FEATURE:
<223> OTHER INFORMATION: Tamapin I22R

<400> SEQUENCE: 414

Ala Phe Cys Asn Leu Arg Arg Cys Glu Leu Ser Cys Arg Ser Leu Gly
1               5                   10                  15
Leu Leu Gly Lys Cys Arg Gly Glu Glu Cys Lys Cys Val Pro Tyr
            20                  25                  30

<210> SEQ ID NO 415
<211> LENGTH: 31
<212> TYPE: PRT
<213> ORGANISM: Artificial Sequence
<220> FEATURE:
<223> OTHER INFORMATION: Tamapin I22S

<400> SEQUENCE: 415

Ala Phe Cys Asn Leu Arg Arg Cys Glu Leu Ser Cys Arg Ser Leu Gly
1               5                   10                  15
Leu Leu Gly Lys Cys Ser Gly Glu Glu Cys Lys Cys Val Pro Tyr
            20                  25                  30

<210> SEQ ID NO 416
<211> LENGTH: 31
<212> TYPE: PRT
```

```
<213> ORGANISM: Artificial Sequence
<220> FEATURE:
<223> OTHER INFORMATION: Tamapin I22T

<400> SEQUENCE: 416

Ala Phe Cys Asn Leu Arg Arg Cys Glu Leu Ser Cys Arg Ser Leu Gly
1               5                   10                  15
Leu Leu Gly Lys Cys Thr Gly Glu Glu Cys Lys Cys Val Pro Tyr
            20                  25                  30

<210> SEQ ID NO 417
<211> LENGTH: 31
<212> TYPE: PRT
<213> ORGANISM: Artificial Sequence
<220> FEATURE:
<223> OTHER INFORMATION: Tamapin I22V

<400> SEQUENCE: 417

Ala Phe Cys Asn Leu Arg Arg Cys Glu Leu Ser Cys Arg Ser Leu Gly
1               5                   10                  15
Leu Leu Gly Lys Cys Val Gly Glu Glu Cys Lys Cys Val Pro Tyr
            20                  25                  30

<210> SEQ ID NO 418
<211> LENGTH: 31
<212> TYPE: PRT
<213> ORGANISM: Artificial Sequence
<220> FEATURE:
<223> OTHER INFORMATION: Tamapin I22W

<400> SEQUENCE: 418

Ala Phe Cys Asn Leu Arg Arg Cys Glu Leu Ser Cys Arg Ser Leu Gly
1               5                   10                  15
Leu Leu Gly Lys Cys Trp Gly Glu Glu Cys Lys Cys Val Pro Tyr
            20                  25                  30

<210> SEQ ID NO 419
<211> LENGTH: 31
<212> TYPE: PRT
<213> ORGANISM: Artificial Sequence
<220> FEATURE:
<223> OTHER INFORMATION: Tamapin I22Y

<400> SEQUENCE: 419

Ala Phe Cys Asn Leu Arg Arg Cys Glu Leu Ser Cys Arg Ser Leu Gly
1               5                   10                  15
Leu Leu Gly Lys Cys Tyr Gly Glu Glu Cys Lys Cys Val Pro Tyr
            20                  25                  30

<210> SEQ ID NO 420
<211> LENGTH: 31
<212> TYPE: PRT
<213> ORGANISM: Artificial Sequence
<220> FEATURE:
<223> OTHER INFORMATION: Tamapin G23A

<400> SEQUENCE: 420

Ala Phe Cys Asn Leu Arg Arg Cys Glu Leu Ser Cys Arg Ser Leu Gly
1               5                   10                  15
Leu Leu Gly Lys Cys Ile Ala Glu Glu Cys Lys Cys Val Pro Tyr
            20                  25                  30

<210> SEQ ID NO 421
<211> LENGTH: 31
```

```
<212> TYPE: PRT
<213> ORGANISM: Artificial Sequence
<220> FEATURE:
<223> OTHER INFORMATION: Tamapin G23C

<400> SEQUENCE: 421

Ala Phe Cys Asn Leu Arg Arg Cys Glu Leu Ser Cys Arg Ser Leu Gly
1               5                   10                  15

Leu Leu Gly Lys Cys Ile Cys Glu Glu Cys Lys Cys Val Pro Tyr
            20                  25                  30

<210> SEQ ID NO 422
<211> LENGTH: 31
<212> TYPE: PRT
<213> ORGANISM: Artificial Sequence
<220> FEATURE:
<223> OTHER INFORMATION: Tamapin G23D

<400> SEQUENCE: 422

Ala Phe Cys Asn Leu Arg Arg Cys Glu Leu Ser Cys Arg Ser Leu Gly
1               5                   10                  15

Leu Leu Gly Lys Cys Ile Asp Glu Glu Cys Lys Cys Val Pro Tyr
            20                  25                  30

<210> SEQ ID NO 423
<211> LENGTH: 31
<212> TYPE: PRT
<213> ORGANISM: Artificial Sequence
<220> FEATURE:
<223> OTHER INFORMATION: Tamapin G23E

<400> SEQUENCE: 423

Ala Phe Cys Asn Leu Arg Arg Cys Glu Leu Ser Cys Arg Ser Leu Gly
1               5                   10                  15

Leu Leu Gly Lys Cys Ile Glu Glu Glu Cys Lys Cys Val Pro Tyr
            20                  25                  30

<210> SEQ ID NO 424
<211> LENGTH: 31
<212> TYPE: PRT
<213> ORGANISM: Artificial Sequence
<220> FEATURE:
<223> OTHER INFORMATION: Tamapin G23F

<400> SEQUENCE: 424

Ala Phe Cys Asn Leu Arg Arg Cys Glu Leu Ser Cys Arg Ser Leu Gly
1               5                   10                  15

Leu Leu Gly Lys Cys Ile Phe Glu Glu Cys Lys Cys Val Pro Tyr
            20                  25                  30

<210> SEQ ID NO 425
<211> LENGTH: 31
<212> TYPE: PRT
<213> ORGANISM: Artificial Sequence
<220> FEATURE:
<223> OTHER INFORMATION: Tamapin G23H

<400> SEQUENCE: 425

Ala Phe Cys Asn Leu Arg Arg Cys Glu Leu Ser Cys Arg Ser Leu Gly
1               5                   10                  15

Leu Leu Gly Lys Cys Ile His Glu Glu Cys Lys Cys Val Pro Tyr
            20                  25                  30

<210> SEQ ID NO 426
```

```
<211> LENGTH: 31
<212> TYPE: PRT
<213> ORGANISM: Artificial Sequence
<220> FEATURE:
<223> OTHER INFORMATION: Tamapin G23I

<400> SEQUENCE: 426

Ala Phe Cys Asn Leu Arg Arg Cys Glu Leu Ser Cys Arg Ser Leu Gly
1               5                   10                  15

Leu Leu Gly Lys Cys Ile Ile Glu Glu Cys Lys Cys Val Pro Tyr
            20                  25                  30

<210> SEQ ID NO 427
<211> LENGTH: 31
<212> TYPE: PRT
<213> ORGANISM: Artificial Sequence
<220> FEATURE:
<223> OTHER INFORMATION: Tamapin G23K

<400> SEQUENCE: 427

Ala Phe Cys Asn Leu Arg Arg Cys Glu Leu Ser Cys Arg Ser Leu Gly
1               5                   10                  15

Leu Leu Gly Lys Cys Ile Lys Glu Glu Cys Lys Cys Val Pro Tyr
            20                  25                  30

<210> SEQ ID NO 428
<211> LENGTH: 31
<212> TYPE: PRT
<213> ORGANISM: Artificial Sequence
<220> FEATURE:
<223> OTHER INFORMATION: Tamapin G23L

<400> SEQUENCE: 428

Ala Phe Cys Asn Leu Arg Arg Cys Glu Leu Ser Cys Arg Ser Leu Gly
1               5                   10                  15

Leu Leu Gly Lys Cys Ile Leu Glu Glu Cys Lys Cys Val Pro Tyr
            20                  25                  30

<210> SEQ ID NO 429
<211> LENGTH: 31
<212> TYPE: PRT
<213> ORGANISM: Artificial Sequence
<220> FEATURE:
<223> OTHER INFORMATION: Tamapin G23M

<400> SEQUENCE: 429

Ala Phe Cys Asn Leu Arg Arg Cys Glu Leu Ser Cys Arg Ser Leu Gly
1               5                   10                  15

Leu Leu Gly Lys Cys Ile Met Glu Glu Cys Lys Cys Val Pro Tyr
            20                  25                  30

<210> SEQ ID NO 430
<211> LENGTH: 31
<212> TYPE: PRT
<213> ORGANISM: Artificial Sequence
<220> FEATURE:
<223> OTHER INFORMATION: Tamapin G23N

<400> SEQUENCE: 430

Ala Phe Cys Asn Leu Arg Arg Cys Glu Leu Ser Cys Arg Ser Leu Gly
1               5                   10                  15

Leu Leu Gly Lys Cys Ile Asn Glu Glu Cys Lys Cys Val Pro Tyr
            20                  25                  30
```

<210> SEQ ID NO 431
<211> LENGTH: 31
<212> TYPE: PRT
<213> ORGANISM: Artificial Sequence
<220> FEATURE:
<223> OTHER INFORMATION: Tamapin G23P

<400> SEQUENCE: 431

Ala Phe Cys Asn Leu Arg Arg Cys Glu Leu Ser Cys Arg Ser Leu Gly
1               5                   10                  15

Leu Leu Gly Lys Cys Ile Pro Glu Glu Cys Lys Cys Val Pro Tyr
            20                  25                  30

<210> SEQ ID NO 432
<211> LENGTH: 31
<212> TYPE: PRT
<213> ORGANISM: Artificial Sequence
<220> FEATURE:
<223> OTHER INFORMATION: Tamapin G23Q

<400> SEQUENCE: 432

Ala Phe Cys Asn Leu Arg Arg Cys Glu Leu Ser Cys Arg Ser Leu Gly
1               5                   10                  15

Leu Leu Gly Lys Cys Ile Gln Glu Glu Cys Lys Cys Val Pro Tyr
            20                  25                  30

<210> SEQ ID NO 433
<211> LENGTH: 31
<212> TYPE: PRT
<213> ORGANISM: Artificial Sequence
<220> FEATURE:
<223> OTHER INFORMATION: Tamapin G23R

<400> SEQUENCE: 433

Ala Phe Cys Asn Leu Arg Arg Cys Glu Leu Ser Cys Arg Ser Leu Gly
1               5                   10                  15

Leu Leu Gly Lys Cys Ile Arg Glu Glu Cys Lys Cys Val Pro Tyr
            20                  25                  30

<210> SEQ ID NO 434
<211> LENGTH: 31
<212> TYPE: PRT
<213> ORGANISM: Artificial Sequence
<220> FEATURE:
<223> OTHER INFORMATION: Tamapin G23S

<400> SEQUENCE: 434

Ala Phe Cys Asn Leu Arg Arg Cys Glu Leu Ser Cys Arg Ser Leu Gly
1               5                   10                  15

Leu Leu Gly Lys Cys Ile Ser Glu Glu Cys Lys Cys Val Pro Tyr
            20                  25                  30

<210> SEQ ID NO 435
<211> LENGTH: 31
<212> TYPE: PRT
<213> ORGANISM: Artificial Sequence
<220> FEATURE:
<223> OTHER INFORMATION: Tamapin G23T

<400> SEQUENCE: 435

Ala Phe Cys Asn Leu Arg Arg Cys Glu Leu Ser Cys Arg Ser Leu Gly
1               5                   10                  15

Leu Leu Gly Lys Cys Ile Thr Glu Glu Cys Lys Cys Val Pro Tyr
            20                  25                  30

```
<210> SEQ ID NO 436
<211> LENGTH: 31
<212> TYPE: PRT
<213> ORGANISM: Artificial Sequence
<220> FEATURE:
<223> OTHER INFORMATION: Tamapin G23V

<400> SEQUENCE: 436

Ala Phe Cys Asn Leu Arg Arg Cys Glu Leu Ser Cys Arg Ser Leu Gly
1               5                   10                  15

Leu Leu Gly Lys Cys Ile Val Glu Glu Cys Lys Cys Val Pro Tyr
            20                  25                  30

<210> SEQ ID NO 437
<211> LENGTH: 31
<212> TYPE: PRT
<213> ORGANISM: Artificial Sequence
<220> FEATURE:
<223> OTHER INFORMATION: Tamapin G23W

<400> SEQUENCE: 437

Ala Phe Cys Asn Leu Arg Arg Cys Glu Leu Ser Cys Arg Ser Leu Gly
1               5                   10                  15

Leu Leu Gly Lys Cys Ile Trp Glu Glu Cys Lys Cys Val Pro Tyr
            20                  25                  30

<210> SEQ ID NO 438
<211> LENGTH: 31
<212> TYPE: PRT
<213> ORGANISM: Artificial Sequence
<220> FEATURE:
<223> OTHER INFORMATION: Tamapin G23Y

<400> SEQUENCE: 438

Ala Phe Cys Asn Leu Arg Arg Cys Glu Leu Ser Cys Arg Ser Leu Gly
1               5                   10                  15

Leu Leu Gly Lys Cys Ile Tyr Glu Glu Cys Lys Cys Val Pro Tyr
            20                  25                  30

<210> SEQ ID NO 439
<211> LENGTH: 31
<212> TYPE: PRT
<213> ORGANISM: Artificial Sequence
<220> FEATURE:
<223> OTHER INFORMATION: Tamapin E24A

<400> SEQUENCE: 439

Ala Phe Cys Asn Leu Arg Arg Cys Glu Leu Ser Cys Arg Ser Leu Gly
1               5                   10                  15

Leu Leu Gly Lys Cys Ile Gly Ala Glu Cys Lys Cys Val Pro Tyr
            20                  25                  30

<210> SEQ ID NO 440
<211> LENGTH: 31
<212> TYPE: PRT
<213> ORGANISM: Artificial Sequence
<220> FEATURE:
<223> OTHER INFORMATION: Tamapin E24C

<400> SEQUENCE: 440

Ala Phe Cys Asn Leu Arg Arg Cys Glu Leu Ser Cys Arg Ser Leu Gly
1               5                   10                  15

Leu Leu Gly Lys Cys Ile Gly Cys Glu Cys Lys Cys Val Pro Tyr
            20                  25                  30
```

<210> SEQ ID NO 441
<211> LENGTH: 31
<212> TYPE: PRT
<213> ORGANISM: Artificial Sequence
<220> FEATURE:
<223> OTHER INFORMATION: Tamapin E24D

<400> SEQUENCE: 441

Ala Phe Cys Asn Leu Arg Arg Cys Glu Leu Ser Cys Arg Ser Leu Gly
1               5                   10                  15

Leu Leu Gly Lys Cys Ile Gly Asp Glu Cys Lys Cys Val Pro Tyr
            20                  25                  30

<210> SEQ ID NO 442
<211> LENGTH: 31
<212> TYPE: PRT
<213> ORGANISM: Artificial Sequence
<220> FEATURE:
<223> OTHER INFORMATION: Tamapin E24F

<400> SEQUENCE: 442

Ala Phe Cys Asn Leu Arg Arg Cys Glu Leu Ser Cys Arg Ser Leu Gly
1               5                   10                  15

Leu Leu Gly Lys Cys Ile Gly Phe Glu Cys Lys Cys Val Pro Tyr
            20                  25                  30

<210> SEQ ID NO 443
<211> LENGTH: 31
<212> TYPE: PRT
<213> ORGANISM: Artificial Sequence
<220> FEATURE:
<223> OTHER INFORMATION: Tamapin E24G

<400> SEQUENCE: 443

Ala Phe Cys Asn Leu Arg Arg Cys Glu Leu Ser Cys Arg Ser Leu Gly
1               5                   10                  15

Leu Leu Gly Lys Cys Ile Gly Gly Glu Cys Lys Cys Val Pro Tyr
            20                  25                  30

<210> SEQ ID NO 444
<211> LENGTH: 31
<212> TYPE: PRT
<213> ORGANISM: Artificial Sequence
<220> FEATURE:
<223> OTHER INFORMATION: Tamapin E24H

<400> SEQUENCE: 444

Ala Phe Cys Asn Leu Arg Arg Cys Glu Leu Ser Cys Arg Ser Leu Gly
1               5                   10                  15

Leu Leu Gly Lys Cys Ile Gly His Glu Cys Lys Cys Val Pro Tyr
            20                  25                  30

<210> SEQ ID NO 445
<211> LENGTH: 31
<212> TYPE: PRT
<213> ORGANISM: Artificial Sequence
<220> FEATURE:
<223> OTHER INFORMATION: Tamapin E24I

<400> SEQUENCE: 445

Ala Phe Cys Asn Leu Arg Arg Cys Glu Leu Ser Cys Arg Ser Leu Gly
1               5                   10                  15

Leu Leu Gly Lys Cys Ile Gly Ile Glu Cys Lys Cys Val Pro Tyr

-continued

```
                 20                  25                  30

<210> SEQ ID NO 446
<211> LENGTH: 31
<212> TYPE: PRT
<213> ORGANISM: Artificial Sequence
<220> FEATURE:
<223> OTHER INFORMATION: Tamapin E24K

<400> SEQUENCE: 446

Ala Phe Cys Asn Leu Arg Arg Cys Glu Leu Ser Cys Arg Ser Leu Gly
1               5                   10                  15

Leu Leu Gly Lys Cys Ile Gly Lys Glu Cys Lys Cys Val Pro Tyr
            20                  25                  30

<210> SEQ ID NO 447
<211> LENGTH: 31
<212> TYPE: PRT
<213> ORGANISM: Artificial Sequence
<220> FEATURE:
<223> OTHER INFORMATION: Tamapin E24L

<400> SEQUENCE: 447

Ala Phe Cys Asn Leu Arg Arg Cys Glu Leu Ser Cys Arg Ser Leu Gly
1               5                   10                  15

Leu Leu Gly Lys Cys Ile Gly Leu Glu Cys Lys Cys Val Pro Tyr
            20                  25                  30

<210> SEQ ID NO 448
<211> LENGTH: 31
<212> TYPE: PRT
<213> ORGANISM: Artificial Sequence
<220> FEATURE:
<223> OTHER INFORMATION: Tamapin E24M

<400> SEQUENCE: 448

Ala Phe Cys Asn Leu Arg Arg Cys Glu Leu Ser Cys Arg Ser Leu Gly
1               5                   10                  15

Leu Leu Gly Lys Cys Ile Gly Met Glu Cys Lys Cys Val Pro Tyr
            20                  25                  30

<210> SEQ ID NO 449
<211> LENGTH: 31
<212> TYPE: PRT
<213> ORGANISM: Artificial Sequence
<220> FEATURE:
<223> OTHER INFORMATION: Tamapin E24N

<400> SEQUENCE: 449

Ala Phe Cys Asn Leu Arg Arg Cys Glu Leu Ser Cys Arg Ser Leu Gly
1               5                   10                  15

Leu Leu Gly Lys Cys Ile Gly Asn Glu Cys Lys Cys Val Pro Tyr
            20                  25                  30

<210> SEQ ID NO 450
<211> LENGTH: 31
<212> TYPE: PRT
<213> ORGANISM: Artificial Sequence
<220> FEATURE:
<223> OTHER INFORMATION: Tamapin E24P

<400> SEQUENCE: 450

Ala Phe Cys Asn Leu Arg Arg Cys Glu Leu Ser Cys Arg Ser Leu Gly
1               5                   10                  15
```

```
Leu Leu Gly Lys Cys Ile Gly Pro Glu Cys Lys Cys Val Pro Tyr
            20                  25                  30
```

<210> SEQ ID NO 451
<211> LENGTH: 31
<212> TYPE: PRT
<213> ORGANISM: Artificial Sequence
<220> FEATURE:
<223> OTHER INFORMATION: Tamapin E24Q

<400> SEQUENCE: 451

```
Ala Phe Cys Asn Leu Arg Arg Cys Glu Leu Ser Cys Arg Ser Leu Gly
1               5                   10                  15

Leu Leu Gly Lys Cys Ile Gly Gln Glu Cys Lys Cys Val Pro Tyr
            20                  25                  30
```

<210> SEQ ID NO 452
<211> LENGTH: 31
<212> TYPE: PRT
<213> ORGANISM: Artificial Sequence
<220> FEATURE:
<223> OTHER INFORMATION: Tamapin E24R

<400> SEQUENCE: 452

```
Ala Phe Cys Asn Leu Arg Arg Cys Glu Leu Ser Cys Arg Ser Leu Gly
1               5                   10                  15

Leu Leu Gly Lys Cys Ile Gly Arg Glu Cys Lys Cys Val Pro Tyr
            20                  25                  30
```

<210> SEQ ID NO 453
<211> LENGTH: 31
<212> TYPE: PRT
<213> ORGANISM: Artificial Sequence
<220> FEATURE:
<223> OTHER INFORMATION: Tamapin E24S

<400> SEQUENCE: 453

```
Ala Phe Cys Asn Leu Arg Arg Cys Glu Leu Ser Cys Arg Ser Leu Gly
1               5                   10                  15

Leu Leu Gly Lys Cys Ile Gly Ser Glu Cys Lys Cys Val Pro Tyr
            20                  25                  30
```

<210> SEQ ID NO 454
<211> LENGTH: 31
<212> TYPE: PRT
<213> ORGANISM: Artificial Sequence
<220> FEATURE:
<223> OTHER INFORMATION: Tamapin E24T

<400> SEQUENCE: 454

```
Ala Phe Cys Asn Leu Arg Arg Cys Glu Leu Ser Cys Arg Ser Leu Gly
1               5                   10                  15

Leu Leu Gly Lys Cys Ile Gly Thr Glu Cys Lys Cys Val Pro Tyr
            20                  25                  30
```

<210> SEQ ID NO 455
<211> LENGTH: 31
<212> TYPE: PRT
<213> ORGANISM: Artificial Sequence
<220> FEATURE:
<223> OTHER INFORMATION: Tamapin E24V

<400> SEQUENCE: 455

```
Ala Phe Cys Asn Leu Arg Arg Cys Glu Leu Ser Cys Arg Ser Leu Gly
1               5                   10                  15
```

Leu Leu Gly Lys Cys Ile Gly Val Glu Cys Lys Cys Val Pro Tyr
            20                  25                  30

<210> SEQ ID NO 456
<211> LENGTH: 31
<212> TYPE: PRT
<213> ORGANISM: Artificial Sequence
<220> FEATURE:
<223> OTHER INFORMATION: Tamapin E24W

<400> SEQUENCE: 456

Ala Phe Cys Asn Leu Arg Arg Cys Glu Leu Ser Cys Arg Ser Leu Gly
1               5                   10                  15

Leu Leu Gly Lys Cys Ile Gly Trp Glu Cys Lys Cys Val Pro Tyr
            20                  25                  30

<210> SEQ ID NO 457
<211> LENGTH: 31
<212> TYPE: PRT
<213> ORGANISM: Artificial Sequence
<220> FEATURE:
<223> OTHER INFORMATION: Tamapin E24Y

<400> SEQUENCE: 457

Ala Phe Cys Asn Leu Arg Arg Cys Glu Leu Ser Cys Arg Ser Leu Gly
1               5                   10                  15

Leu Leu Gly Lys Cys Ile Gly Tyr Glu Cys Lys Cys Val Pro Tyr
            20                  25                  30

<210> SEQ ID NO 458
<211> LENGTH: 31
<212> TYPE: PRT
<213> ORGANISM: Artificial Sequence
<220> FEATURE:
<223> OTHER INFORMATION: Tamapin E25A

<400> SEQUENCE: 458

Ala Phe Cys Asn Leu Arg Arg Cys Glu Leu Ser Cys Arg Ser Leu Gly
1               5                   10                  15

Leu Leu Gly Lys Cys Ile Gly Glu Ala Cys Lys Cys Val Pro Tyr
            20                  25                  30

<210> SEQ ID NO 459
<211> LENGTH: 31
<212> TYPE: PRT
<213> ORGANISM: Artificial Sequence
<220> FEATURE:
<223> OTHER INFORMATION: Tamapin E25C

<400> SEQUENCE: 459

Ala Phe Cys Asn Leu Arg Arg Cys Glu Leu Ser Cys Arg Ser Leu Gly
1               5                   10                  15

Leu Leu Gly Lys Cys Ile Gly Glu Cys Cys Lys Cys Val Pro Tyr
            20                  25                  30

<210> SEQ ID NO 460
<211> LENGTH: 31
<212> TYPE: PRT
<213> ORGANISM: Artificial Sequence
<220> FEATURE:
<223> OTHER INFORMATION: Tamapin E25D

<400> SEQUENCE: 460

Ala Phe Cys Asn Leu Arg Arg Cys Glu Leu Ser Cys Arg Ser Leu Gly

-continued

```
                1               5                  10                  15
Leu Leu Gly Lys Cys Ile Gly Glu Asp Cys Lys Cys Val Pro Tyr
            20                  25                  30
```

<210> SEQ ID NO 461
<211> LENGTH: 31
<212> TYPE: PRT
<213> ORGANISM: Artificial Sequence
<220> FEATURE:
<223> OTHER INFORMATION: Tamapin E25F

<400> SEQUENCE: 461

```
Ala Phe Cys Asn Leu Arg Arg Cys Glu Leu Ser Cys Arg Ser Leu Gly
1               5                   10                  15
Leu Leu Gly Lys Cys Ile Gly Glu Phe Cys Lys Cys Val Pro Tyr
            20                  25                  30
```

<210> SEQ ID NO 462
<211> LENGTH: 31
<212> TYPE: PRT
<213> ORGANISM: Artificial Sequence
<220> FEATURE:
<223> OTHER INFORMATION: Tamapin E25G

<400> SEQUENCE: 462

```
Ala Phe Cys Asn Leu Arg Arg Cys Glu Leu Ser Cys Arg Ser Leu Gly
1               5                   10                  15
Leu Leu Gly Lys Cys Ile Gly Glu Gly Cys Lys Cys Val Pro Tyr
            20                  25                  30
```

<210> SEQ ID NO 463
<211> LENGTH: 31
<212> TYPE: PRT
<213> ORGANISM: Artificial Sequence
<220> FEATURE:
<223> OTHER INFORMATION: Tamapin E25H

<400> SEQUENCE: 463

```
Ala Phe Cys Asn Leu Arg Arg Cys Glu Leu Ser Cys Arg Ser Leu Gly
1               5                   10                  15
Leu Leu Gly Lys Cys Ile Gly Glu His Cys Lys Cys Val Pro Tyr
            20                  25                  30
```

<210> SEQ ID NO 464
<211> LENGTH: 31
<212> TYPE: PRT
<213> ORGANISM: Artificial Sequence
<220> FEATURE:
<223> OTHER INFORMATION: Tamapin E25I

<400> SEQUENCE: 464

```
Ala Phe Cys Asn Leu Arg Arg Cys Glu Leu Ser Cys Arg Ser Leu Gly
1               5                   10                  15
Leu Leu Gly Lys Cys Ile Gly Glu Ile Cys Lys Cys Val Pro Tyr
            20                  25                  30
```

<210> SEQ ID NO 465
<211> LENGTH: 31
<212> TYPE: PRT
<213> ORGANISM: Artificial Sequence
<220> FEATURE:
<223> OTHER INFORMATION: Tamapin E25K

<400> SEQUENCE: 465

```
Ala Phe Cys Asn Leu Arg Arg Cys Glu Leu Ser Cys Arg Ser Leu Gly
1               5                   10                  15

Leu Leu Gly Lys Cys Ile Gly Glu Lys Cys Lys Cys Val Pro Tyr
            20                  25                  30
```

<210> SEQ ID NO 466
<211> LENGTH: 31
<212> TYPE: PRT
<213> ORGANISM: Artificial Sequence
<220> FEATURE:
<223> OTHER INFORMATION: Tamapin E25L

<400> SEQUENCE: 466

```
Ala Phe Cys Asn Leu Arg Arg Cys Glu Leu Ser Cys Arg Ser Leu Gly
1               5                   10                  15

Leu Leu Gly Lys Cys Ile Gly Glu Leu Cys Lys Cys Val Pro Tyr
            20                  25                  30
```

<210> SEQ ID NO 467
<211> LENGTH: 31
<212> TYPE: PRT
<213> ORGANISM: Artificial Sequence
<220> FEATURE:
<223> OTHER INFORMATION: Tamapin E25M

<400> SEQUENCE: 467

```
Ala Phe Cys Asn Leu Arg Arg Cys Glu Leu Ser Cys Arg Ser Leu Gly
1               5                   10                  15

Leu Leu Gly Lys Cys Ile Gly Glu Met Cys Lys Cys Val Pro Tyr
            20                  25                  30
```

<210> SEQ ID NO 468
<211> LENGTH: 31
<212> TYPE: PRT
<213> ORGANISM: Artificial Sequence
<220> FEATURE:
<223> OTHER INFORMATION: Tamapin E25N

<400> SEQUENCE: 468

```
Ala Phe Cys Asn Leu Arg Arg Cys Glu Leu Ser Cys Arg Ser Leu Gly
1               5                   10                  15

Leu Leu Gly Lys Cys Ile Gly Glu Asn Cys Lys Cys Val Pro Tyr
            20                  25                  30
```

<210> SEQ ID NO 469
<211> LENGTH: 31
<212> TYPE: PRT
<213> ORGANISM: Artificial Sequence
<220> FEATURE:
<223> OTHER INFORMATION: Tamapin E25P

<400> SEQUENCE: 469

```
Ala Phe Cys Asn Leu Arg Arg Cys Glu Leu Ser Cys Arg Ser Leu Gly
1               5                   10                  15

Leu Leu Gly Lys Cys Ile Gly Glu Pro Cys Lys Cys Val Pro Tyr
            20                  25                  30
```

<210> SEQ ID NO 470
<211> LENGTH: 31
<212> TYPE: PRT
<213> ORGANISM: Artificial Sequence
<220> FEATURE:
<223> OTHER INFORMATION: Tamapin E25Q

<400> SEQUENCE: 470

```
Ala Phe Cys Asn Leu Arg Arg Cys Glu Leu Ser Cys Arg Ser Leu Gly
1               5                   10                  15

Leu Leu Gly Lys Cys Ile Gly Glu Gln Cys Lys Cys Val Pro Tyr
            20                  25                  30
```

<210> SEQ ID NO 471
<211> LENGTH: 31
<212> TYPE: PRT
<213> ORGANISM: Artificial Sequence
<220> FEATURE:
<223> OTHER INFORMATION: Tamapin E25R

<400> SEQUENCE: 471

```
Ala Phe Cys Asn Leu Arg Arg Cys Glu Leu Ser Cys Arg Ser Leu Gly
1               5                   10                  15

Leu Leu Gly Lys Cys Ile Gly Glu Arg Cys Lys Cys Val Pro Tyr
            20                  25                  30
```

<210> SEQ ID NO 472
<211> LENGTH: 31
<212> TYPE: PRT
<213> ORGANISM: Artificial Sequence
<220> FEATURE:
<223> OTHER INFORMATION: Tamapin E25S

<400> SEQUENCE: 472

```
Ala Phe Cys Asn Leu Arg Arg Cys Glu Leu Ser Cys Arg Ser Leu Gly
1               5                   10                  15

Leu Leu Gly Lys Cys Ile Gly Glu Ser Cys Lys Cys Val Pro Tyr
            20                  25                  30
```

<210> SEQ ID NO 473
<211> LENGTH: 31
<212> TYPE: PRT
<213> ORGANISM: Artificial Sequence
<220> FEATURE:
<223> OTHER INFORMATION: Tamapin E25T

<400> SEQUENCE: 473

```
Ala Phe Cys Asn Leu Arg Arg Cys Glu Leu Ser Cys Arg Ser Leu Gly
1               5                   10                  15

Leu Leu Gly Lys Cys Ile Gly Glu Thr Cys Lys Cys Val Pro Tyr
            20                  25                  30
```

<210> SEQ ID NO 474
<211> LENGTH: 31
<212> TYPE: PRT
<213> ORGANISM: Artificial Sequence
<220> FEATURE:
<223> OTHER INFORMATION: Tamapin E25V

<400> SEQUENCE: 474

```
Ala Phe Cys Asn Leu Arg Arg Cys Glu Leu Ser Cys Arg Ser Leu Gly
1               5                   10                  15

Leu Leu Gly Lys Cys Ile Gly Glu Val Cys Lys Cys Val Pro Tyr
            20                  25                  30
```

<210> SEQ ID NO 475
<211> LENGTH: 31
<212> TYPE: PRT
<213> ORGANISM: Artificial Sequence
<220> FEATURE:
<223> OTHER INFORMATION: Tamapin E25W

```
<400> SEQUENCE: 475

Ala Phe Cys Asn Leu Arg Arg Cys Glu Leu Ser Cys Arg Ser Leu Gly
1               5                   10                  15

Leu Leu Gly Lys Cys Ile Gly Glu Trp Cys Lys Cys Val Pro Tyr
            20                  25                  30

<210> SEQ ID NO 476
<211> LENGTH: 31
<212> TYPE: PRT
<213> ORGANISM: Artificial Sequence
<220> FEATURE:
<223> OTHER INFORMATION: Tamapin E25Y

<400> SEQUENCE: 476

Ala Phe Cys Asn Leu Arg Arg Cys Glu Leu Ser Cys Arg Ser Leu Gly
1               5                   10                  15

Leu Leu Gly Lys Cys Ile Gly Glu Tyr Cys Lys Cys Val Pro Tyr
            20                  25                  30

<210> SEQ ID NO 477
<211> LENGTH: 31
<212> TYPE: PRT
<213> ORGANISM: Artificial Sequence
<220> FEATURE:
<223> OTHER INFORMATION: Tamapin C26A

<400> SEQUENCE: 477

Ala Phe Cys Asn Leu Arg Arg Cys Glu Leu Ser Cys Arg Ser Leu Gly
1               5                   10                  15

Leu Leu Gly Lys Cys Ile Gly Glu Glu Ala Lys Cys Val Pro Tyr
            20                  25                  30

<210> SEQ ID NO 478
<211> LENGTH: 31
<212> TYPE: PRT
<213> ORGANISM: Artificial Sequence
<220> FEATURE:
<223> OTHER INFORMATION: Tamapin C26D

<400> SEQUENCE: 478

Ala Phe Cys Asn Leu Arg Arg Cys Glu Leu Ser Cys Arg Ser Leu Gly
1               5                   10                  15

Leu Leu Gly Lys Cys Ile Gly Glu Glu Asp Lys Cys Val Pro Tyr
            20                  25                  30

<210> SEQ ID NO 479
<211> LENGTH: 31
<212> TYPE: PRT
<213> ORGANISM: Artificial Sequence
<220> FEATURE:
<223> OTHER INFORMATION: Tamapin C26E

<400> SEQUENCE: 479

Ala Phe Cys Asn Leu Arg Arg Cys Glu Leu Ser Cys Arg Ser Leu Gly
1               5                   10                  15

Leu Leu Gly Lys Cys Ile Gly Glu Glu Glu Lys Cys Val Pro Tyr
            20                  25                  30

<210> SEQ ID NO 480
<211> LENGTH: 31
<212> TYPE: PRT
<213> ORGANISM: Artificial Sequence
<220> FEATURE:
<223> OTHER INFORMATION: Tamapin C26F
```

<400> SEQUENCE: 480

Ala Phe Cys Asn Leu Arg Arg Cys Glu Leu Ser Cys Arg Ser Leu Gly
1               5                   10                  15

Leu Leu Gly Lys Cys Ile Gly Glu Glu Phe Lys Cys Val Pro Tyr
            20                  25                  30

<210> SEQ ID NO 481
<211> LENGTH: 31
<212> TYPE: PRT
<213> ORGANISM: Artificial Sequence
<220> FEATURE:
<223> OTHER INFORMATION: Tamapin C26G

<400> SEQUENCE: 481

Ala Phe Cys Asn Leu Arg Arg Cys Glu Leu Ser Cys Arg Ser Leu Gly
1               5                   10                  15

Leu Leu Gly Lys Cys Ile Gly Glu Glu Gly Lys Cys Val Pro Tyr
            20                  25                  30

<210> SEQ ID NO 482
<211> LENGTH: 31
<212> TYPE: PRT
<213> ORGANISM: Artificial Sequence
<220> FEATURE:
<223> OTHER INFORMATION: Tamapin C26H

<400> SEQUENCE: 482

Ala Phe Cys Asn Leu Arg Arg Cys Glu Leu Ser Cys Arg Ser Leu Gly
1               5                   10                  15

Leu Leu Gly Lys Cys Ile Gly Glu Glu His Lys Cys Val Pro Tyr
            20                  25                  30

<210> SEQ ID NO 483
<211> LENGTH: 31
<212> TYPE: PRT
<213> ORGANISM: Artificial Sequence
<220> FEATURE:
<223> OTHER INFORMATION: Tamapin C26I

<400> SEQUENCE: 483

Ala Phe Cys Asn Leu Arg Arg Cys Glu Leu Ser Cys Arg Ser Leu Gly
1               5                   10                  15

Leu Leu Gly Lys Cys Ile Gly Glu Glu Ile Lys Cys Val Pro Tyr
            20                  25                  30

<210> SEQ ID NO 484
<211> LENGTH: 31
<212> TYPE: PRT
<213> ORGANISM: Artificial Sequence
<220> FEATURE:
<223> OTHER INFORMATION: Tamapin C26K

<400> SEQUENCE: 484

Ala Phe Cys Asn Leu Arg Arg Cys Glu Leu Ser Cys Arg Ser Leu Gly
1               5                   10                  15

Leu Leu Gly Lys Cys Ile Gly Glu Glu Lys Lys Cys Val Pro Tyr
            20                  25                  30

<210> SEQ ID NO 485
<211> LENGTH: 31
<212> TYPE: PRT
<213> ORGANISM: Artificial Sequence
<220> FEATURE:

<223> OTHER INFORMATION: Tamapin C26L

<400> SEQUENCE: 485

Ala Phe Cys Asn Leu Arg Arg Cys Glu Leu Ser Cys Arg Ser Leu Gly
1               5                   10                  15

Leu Leu Gly Lys Cys Ile Gly Glu Glu Leu Lys Cys Val Pro Tyr
            20                  25                  30

<210> SEQ ID NO 486
<211> LENGTH: 31
<212> TYPE: PRT
<213> ORGANISM: Artificial Sequence
<220> FEATURE:
<223> OTHER INFORMATION: Tamapin C26M

<400> SEQUENCE: 486

Ala Phe Cys Asn Leu Arg Arg Cys Glu Leu Ser Cys Arg Ser Leu Gly
1               5                   10                  15

Leu Leu Gly Lys Cys Ile Gly Glu Glu Met Lys Cys Val Pro Tyr
            20                  25                  30

<210> SEQ ID NO 487
<211> LENGTH: 31
<212> TYPE: PRT
<213> ORGANISM: Artificial Sequence
<220> FEATURE:
<223> OTHER INFORMATION: Tamapin C26N

<400> SEQUENCE: 487

Ala Phe Cys Asn Leu Arg Arg Cys Glu Leu Ser Cys Arg Ser Leu Gly
1               5                   10                  15

Leu Leu Gly Lys Cys Ile Gly Glu Glu Asn Lys Cys Val Pro Tyr
            20                  25                  30

<210> SEQ ID NO 488
<211> LENGTH: 31
<212> TYPE: PRT
<213> ORGANISM: Artificial Sequence
<220> FEATURE:
<223> OTHER INFORMATION: Tamapin C26P

<400> SEQUENCE: 488

Ala Phe Cys Asn Leu Arg Arg Cys Glu Leu Ser Cys Arg Ser Leu Gly
1               5                   10                  15

Leu Leu Gly Lys Cys Ile Gly Glu Glu Pro Lys Cys Val Pro Tyr
            20                  25                  30

<210> SEQ ID NO 489
<211> LENGTH: 31
<212> TYPE: PRT
<213> ORGANISM: Artificial Sequence
<220> FEATURE:
<223> OTHER INFORMATION: Tamapin C26Q

<400> SEQUENCE: 489

Ala Phe Cys Asn Leu Arg Arg Cys Glu Leu Ser Cys Arg Ser Leu Gly
1               5                   10                  15

Leu Leu Gly Lys Cys Ile Gly Glu Glu Gln Lys Cys Val Pro Tyr
            20                  25                  30

<210> SEQ ID NO 490
<211> LENGTH: 31
<212> TYPE: PRT
<213> ORGANISM: Artificial Sequence
<220> FEATURE:
<223> OTHER INFORMATION: Tamapin C26R

<400> SEQUENCE: 490

Ala Phe Cys Asn Leu Arg Arg Cys Glu Leu Ser Cys Arg Ser Leu Gly
1               5                   10                  15

Leu Leu Gly Lys Cys Ile Gly Glu Glu Arg Lys Cys Val Pro Tyr
            20                  25                  30

<210> SEQ ID NO 491
<211> LENGTH: 31
<212> TYPE: PRT
<213> ORGANISM: Artificial Sequence
<220> FEATURE:
<223> OTHER INFORMATION: Tamapin C26S

<400> SEQUENCE: 491

Ala Phe Cys Asn Leu Arg Arg Cys Glu Leu Ser Cys Arg Ser Leu Gly
1               5                   10                  15

Leu Leu Gly Lys Cys Ile Gly Glu Glu Ser Lys Cys Val Pro Tyr
            20                  25                  30

<210> SEQ ID NO 492
<211> LENGTH: 31
<212> TYPE: PRT
<213> ORGANISM: Artificial Sequence
<220> FEATURE:
<223> OTHER INFORMATION: Tamapin C26T

<400> SEQUENCE: 492

Ala Phe Cys Asn Leu Arg Arg Cys Glu Leu Ser Cys Arg Ser Leu Gly
1               5                   10                  15

Leu Leu Gly Lys Cys Ile Gly Glu Glu Thr Lys Cys Val Pro Tyr
            20                  25                  30

<210> SEQ ID NO 493
<211> LENGTH: 31
<212> TYPE: PRT
<213> ORGANISM: Artificial Sequence
<220> FEATURE:
<223> OTHER INFORMATION: Tamapin C26V

<400> SEQUENCE: 493

Ala Phe Cys Asn Leu Arg Arg Cys Glu Leu Ser Cys Arg Ser Leu Gly
1               5                   10                  15

Leu Leu Gly Lys Cys Ile Gly Glu Glu Val Lys Cys Val Pro Tyr
            20                  25                  30

<210> SEQ ID NO 494
<211> LENGTH: 31
<212> TYPE: PRT
<213> ORGANISM: Artificial Sequence
<220> FEATURE:
<223> OTHER INFORMATION: Tamapin C26W

<400> SEQUENCE: 494

Ala Phe Cys Asn Leu Arg Arg Cys Glu Leu Ser Cys Arg Ser Leu Gly
1               5                   10                  15

Leu Leu Gly Lys Cys Ile Gly Glu Glu Trp Lys Cys Val Pro Tyr
            20                  25                  30

<210> SEQ ID NO 495
<211> LENGTH: 31
<212> TYPE: PRT

<213> ORGANISM: Artificial Sequence
<220> FEATURE:
<223> OTHER INFORMATION: Tamapin C26Y

<400> SEQUENCE: 495

Ala Phe Cys Asn Leu Arg Arg Cys Glu Leu Ser Cys Arg Ser Leu Gly
1               5                   10                  15
Leu Leu Gly Lys Cys Ile Gly Glu Glu Tyr Lys Cys Val Pro Tyr
            20                  25                  30

<210> SEQ ID NO 496
<211> LENGTH: 31
<212> TYPE: PRT
<213> ORGANISM: Artificial Sequence
<220> FEATURE:
<223> OTHER INFORMATION: Tamapin K27A

<400> SEQUENCE: 496

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Ala Cys Val Pro Tyr
            20                  25                  30

<210> SEQ ID NO 497
<211> LENGTH: 31
<212> TYPE: PRT
<213> ORGANISM: Artificial Sequence
<220> FEATURE:
<223> OTHER INFORMATION: Tamapin K27C

<400> SEQUENCE: 497

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Cys Cys Val Pro Tyr
            20                  25                  30

<210> SEQ ID NO 498
<211> LENGTH: 31
<212> TYPE: PRT
<213> ORGANISM: Artificial Sequence
<220> FEATURE:
<223> OTHER INFORMATION: Tamapin K27D

<400> SEQUENCE: 498

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Asp Cys Val Pro Tyr
            20                  25                  30

<210> SEQ ID NO 499
<211> LENGTH: 31
<212> TYPE: PRT
<213> ORGANISM: Artificial Sequence
<220> FEATURE:
<223> OTHER INFORMATION: Tamapin K27E

<400> SEQUENCE: 499

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Glu Cys Val Pro Tyr
            20                  25                  30

<210> SEQ ID NO 500
<211> LENGTH: 31

<212> TYPE: PRT
<213> ORGANISM: Artificial Sequence
<220> FEATURE:
<223> OTHER INFORMATION: Tamapin K27F

<400> SEQUENCE: 500

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Phe Cys Val Pro Tyr
            20                  25                  30

<210> SEQ ID NO 501
<211> LENGTH: 31
<212> TYPE: PRT
<213> ORGANISM: Artificial Sequence
<220> FEATURE:
<223> OTHER INFORMATION: Tamapin K27G

<400> SEQUENCE: 501

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Gly Cys Val Pro Tyr
            20                  25                  30

<210> SEQ ID NO 502
<211> LENGTH: 31
<212> TYPE: PRT
<213> ORGANISM: Artificial Sequence
<220> FEATURE:
<223> OTHER INFORMATION: Tamapin K27H

<400> SEQUENCE: 502

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys His Cys Val Pro Tyr
            20                  25                  30

<210> SEQ ID NO 503
<211> LENGTH: 31
<212> TYPE: PRT
<213> ORGANISM: Artificial Sequence
<220> FEATURE:
<223> OTHER INFORMATION: Tamapin K27I

<400> SEQUENCE: 503

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Ile Cys Val Pro Tyr
            20                  25                  30

<210> SEQ ID NO 504
<211> LENGTH: 31
<212> TYPE: PRT
<213> ORGANISM: Artificial Sequence
<220> FEATURE:
<223> OTHER INFORMATION: Tamapin K27L

<400> SEQUENCE: 504

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Leu Cys Val Pro Tyr
            20                  25                  30

<210> SEQ ID NO 505

-continued

```
<211> LENGTH: 31
<212> TYPE: PRT
<213> ORGANISM: Artificial Sequence
<220> FEATURE:
<223> OTHER INFORMATION: Tamapin K27M

<400> SEQUENCE: 505
```

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Met Cys Val Pro Tyr
            20                  25                  30

```
<210> SEQ ID NO 506
<211> LENGTH: 31
<212> TYPE: PRT
<213> ORGANISM: Artificial Sequence
<220> FEATURE:
<223> OTHER INFORMATION: Tamapin K27N

<400> SEQUENCE: 506
```

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Asn Cys Val Pro Tyr
            20                  25                  30

```
<210> SEQ ID NO 507
<211> LENGTH: 31
<212> TYPE: PRT
<213> ORGANISM: Artificial Sequence
<220> FEATURE:
<223> OTHER INFORMATION: Tamapin K27P

<400> SEQUENCE: 507
```

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Pro Cys Val Pro Tyr
            20                  25                  30

```
<210> SEQ ID NO 508
<211> LENGTH: 31
<212> TYPE: PRT
<213> ORGANISM: Artificial Sequence
<220> FEATURE:
<223> OTHER INFORMATION: Tamapin K27Q

<400> SEQUENCE: 508
```

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Gln Cys Val Pro Tyr
            20                  25                  30

```
<210> SEQ ID NO 509
<211> LENGTH: 31
<212> TYPE: PRT
<213> ORGANISM: Artificial Sequence
<220> FEATURE:
<223> OTHER INFORMATION: Tamapin K27R

<400> SEQUENCE: 509
```

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Arg Cys Val Pro Tyr
            20                  25                  30

```
<210> SEQ ID NO 510
<211> LENGTH: 31
<212> TYPE: PRT
<213> ORGANISM: Artificial Sequence
<220> FEATURE:
<223> OTHER INFORMATION: Tamapin K27S

<400> SEQUENCE: 510

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Ser Cys Val Pro Tyr
            20                  25                  30

<210> SEQ ID NO 511
<211> LENGTH: 31
<212> TYPE: PRT
<213> ORGANISM: Artificial Sequence
<220> FEATURE:
<223> OTHER INFORMATION: Tamapin K27T

<400> SEQUENCE: 511

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Thr Cys Val Pro Tyr
            20                  25                  30

<210> SEQ ID NO 512
<211> LENGTH: 31
<212> TYPE: PRT
<213> ORGANISM: Artificial Sequence
<220> FEATURE:
<223> OTHER INFORMATION: Tamapin K27V

<400> SEQUENCE: 512

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Val Cys Val Pro Ty

<210> SEQ ID NO 515
<211> LENGTH: 31
<212> TYPE: PRT
<213> ORGANISM: Artificial Sequence
<220> FEATURE:
<223> OTHER INFORMATION: Tamapin C28A

<400> SEQUENCE: 515

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Ala Val Pro Tyr
            20                  25                  30

<210> SEQ ID NO 516
<211> LENGTH: 31
<212> TYPE: PRT
<213> ORGANISM: Artificial Sequence
<220> FEATURE:
<223> OTHER INFORMATION: Tamapin C28D

<400> SEQUENCE: 516

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Asp Val Pro Tyr
            20                  25                  30

<210> SEQ ID NO 517
<211> LENGTH: 31
<212> TYPE: PRT
<213> ORGANISM: Artificial Sequence
<220> FEATURE:
<223> OTHER INFORMATION: Tamapin C28E

<400> SEQUENCE: 517

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Glu Val Pro Tyr
            20                  25                  30

<210> SEQ ID NO 518
<211> LENGTH: 31
<212> TYPE: PRT
<213> ORGANISM: Artificial Sequence
<220> FEATURE:
<223> OTHER INFORMATION: Tamapin C28F

<400> SEQUENCE: 518

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Phe Val Pro Tyr
            20                  25                  30

<210> SEQ ID NO 519
<211> LENGTH: 31
<212> TYPE: PRT
<213> ORGANISM: Artificial Sequence
<220> FEATURE:
<223> OTHER INFORMATION: Tamapin C28G

<400> SEQUENCE: 519

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Gly Val Pro Tyr
            20                  25                  30

<210> SEQ ID NO 520
<211> LENGTH: 31
<212> TYPE: PRT
<213> ORGANISM: Artificial Sequence
<220> FEATURE:
<223> OTHER INFORMATION: Tamapin C28H

<400> SEQUENCE: 520

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys His Val Pro Tyr
            20                  25                  30

<210> SEQ ID NO 521
<211> LENGTH: 31
<212> TYPE: PRT
<213> ORGANISM: Artificial Sequence
<220> FEATURE:
<223> OTHER INFORMATION: Tamapin C28I

<400> SEQUENCE: 521

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Ile Val Pro Tyr
            20                  25                  30

<210> SEQ ID NO 522
<211> LENGTH: 31
<212> TYPE: PRT
<213> ORGANISM: Artificial Sequence
<220> FEATURE:
<223> OTHER INFORMATION: Tamapin C28K

<400> SEQUENCE: 522

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Lys Val Pro Tyr
            20                  25                  30

<210> SEQ ID NO 523
<211> LENGTH: 31
<212> TYPE: PRT
<213> ORGANISM: Artificial Sequence
<220> FEATURE:
<223> OTHER INFORMATION: Tamapin C28L

<400> SEQUENCE: 523

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Leu Val Pro Tyr
            20                  25                  30

<210> SEQ ID NO 524
<211> LENGTH: 31
<212> TYPE: PRT
<213> ORGANISM: Artificial Sequence
<220> FEATURE:
<223> OTHER INFORMATION: Tamapin C28M

<400> SEQUENCE: 524

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Met Val Pro Tyr

```
                 20                  25                  30

<210> SEQ ID NO 525
<211> LENGTH: 31
<212> TYPE: PRT
<213> ORGANISM: Artificial Sequence
<220> FEATURE:
<223> OTHER INFORMATION: Tamapin analog

<400> SEQUENCE: 525

Ala Phe Cys Asn Leu Arg Arg Cys Glu Leu Ser Cys Arg Ser Leu Gly
1               5                  10                  15

Leu Leu Gly Lys Cys Ile Gly Glu Glu Cys Lys Asn Val Pro Tyr
            20                  25                  30

<210> SEQ ID NO 526
<211> LENGTH: 31
<212> TYPE: PRT
<213> ORGANISM: Artificial Sequence
<220> FEATURE:
<223> OTHER INFORMATION: Tamapin C28P

<400> SEQUENCE: 526

Ala Phe Cys Asn Leu Arg Arg Cys Glu Leu Ser Cys Arg Ser Leu Gly
1               5                  10                  15

Leu Leu Gly Lys Cys Ile Gly Glu Glu Cys Lys Pro Val Pro Tyr
            20                  25                  30

<210> SEQ ID NO 527
<211> LENGTH: 31
<212> TYPE: PRT
<213> ORGANISM: Artificial Sequence
<220> FEATURE:
<223> OTHER INFORMATION: Tamapin C28Q

<400> SEQUENCE: 527

Ala Phe Cys Asn Leu Arg Arg Cys Glu Leu Ser Cys Arg Ser Leu Gly
1               5                  10                  15

Leu Leu Gly Lys Cys Ile Gly Glu Glu Cys Lys Gln Val Pro Tyr
            20                  25                  30

<210> SEQ ID NO 528
<211> LENGTH: 31
<212> TYPE: PRT
<213> ORGANISM: Artificial Sequence
<220> FEATURE:
<223> OTHER INFORMATION: Tamapin C28R

<400> SEQUENCE: 528

Ala Phe Cys Asn Leu Arg Arg Cys Glu Leu Ser Cys Arg Ser Leu Gly
1               5                  10                  15

Leu Leu Gly Lys Cys Ile Gly Glu Glu Cys Lys Arg Val Pro Tyr
            20                  25                  30

<210> SEQ ID NO 529
<211> LENGTH: 31
<212> TYPE: PRT
<213> ORGANISM: Artificial Sequence
<220> FEATURE:
<223> OTHER INFORMATION: Tamapin C28S

<400> SEQUENCE: 529

Ala Phe Cys Asn Leu Arg Arg Cys Glu Leu Ser Cys Arg Ser Leu Gly
1               5                  10                  15
```

Leu Leu Gly Lys Cys Ile Gly Glu Glu Cys Lys Ser Val Pro Tyr
            20                  25                  30

<210> SEQ ID NO 530
<211> LENGTH: 31
<212> TYPE: PRT
<213> ORGANISM: Artificial Sequence
<220> FEATURE:
<223> OTHER INFORMATION: Tamapin C28T

<400> SEQUENCE: 530

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Thr Val Pro Tyr
            20                  25                  30

<210> SEQ ID NO 531
<211> LENGTH: 31
<212> TYPE: PRT
<213> ORGANISM: Artificial Sequence
<220> FEATURE:
<223> OTHER INFORMATION: Tamapin C28V

<400> SEQUENCE: 531

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Val Val Pro Tyr
            20                  25                  30

<210> SEQ ID NO 532
<211> LENGTH: 31
<212> TYPE: PRT
<213> ORGANISM: Artificial Sequence
<220> FEATURE:
<223> OTHER INFORMATION: Tamapin C28W

<400> SEQUENCE: 532

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Trp Val Pro Tyr
            20                  25                  30

<210> SEQ ID NO 533
<211> LENGTH: 31
<212> TYPE: PRT
<213> ORGANISM: Artificial Sequence
<220> FEATURE:
<223> OTHER INFORMATION: Tamapin C28Y

<400> SEQUENCE: 533

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Tyr Val Pro Tyr
            20                  25                  30

<210> SEQ ID NO 534
<211> LENGTH: 31
<212> TYPE: PRT
<213> ORGANISM: Artificial Sequence
<220> FEATURE:
<223> OTHER INFORMATION: Tamapin V29A

<400> SEQUENCE: 534

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Ala Pro Tyr
            20                  25                  30

<210> SEQ ID NO 535
<211> LENGTH: 31
<212> TYPE: PRT
<213> ORGANISM: Artificial Sequence
<220> FEATURE:
<223> OTHER INFORMATION: Tamapin V29C

<400> SEQUENCE: 535

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Cys Pro Tyr
            20                  25                  30

<210> SEQ ID NO 536
<211> LENGTH: 31
<212> TYPE: PRT
<213> ORGANISM: Artificial Sequence
<220> FEATURE:
<223> OTHER INFORMATION: Tamapin V29D

<400> SEQUENCE: 536

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Asp Pro Tyr
            20                  25                  30

<210> SEQ ID NO 537
<211> LENGTH: 31
<212> TYPE: PRT
<213> ORGANISM: Artificial Sequence
<220> FEATURE:
<223> OTHER INFORMATION: Tamapin V29E

<400> SEQUENCE: 537

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Glu Pro Tyr
            20                  25                  30

<210> SEQ ID NO 538
<211> LENGTH: 31
<212> TYPE: PRT
<213> ORGANISM: Artificial Sequence
<220> FEATURE:
<223> OTHER INFORMATION: Tamapin V29F

<400> SEQUENCE: 538

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Phe Pro Tyr
            20                  25                  30

<210> SEQ ID NO 539
<211> LENGTH: 31
<212> TYPE: PRT
<213> ORGANISM: Artificial Sequence
<220> FEATURE:
<223> OTHER INFORMATION: Tamapin V29G

<400> SEQUENCE: 539

Ala Phe Cys Asn Leu Arg Arg Cys Glu Leu Ser Cys Arg Ser Leu Gly

```
1               5                   10                  15
Leu Leu Gly Lys Cys Ile Gly Glu Glu Cys Lys Cys Gly Pro Tyr
            20                  25                  30
```

<210> SEQ ID NO 540
<211> LENGTH: 31
<212> TYPE: PRT
<213> ORGANISM: Artificial Sequence
<220> FEATURE:
<223> OTHER INFORMATION: Tamapin V29H

<400> SEQUENCE: 540

```
Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys His Pro Tyr
            20                  25                  30
```

<210> SEQ ID NO 541
<211> LENGTH: 31
<212> TYPE: PRT
<213> ORGANISM: Artificial Sequence
<220> FEATURE:
<223> OTHER INFORMATION: Tamapin V29I

<400> SEQUENCE: 541

```
Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Ile Pro Tyr
            20                  25                  30
```

<210> SEQ ID NO 542
<211> LENGTH: 31
<212> TYPE: PRT
<213> ORGANISM: Artificial Sequence
<220> FEATURE:
<223> OTHER INFORMATION: Tamapin V29K

<400> SEQUENCE: 542

```
Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Lys Pro Tyr
            20                  25                  30
```

<210> SEQ ID NO 543
<211> LENGTH: 31
<212> TYPE: PRT
<213> ORGANISM: Artificial Sequence
<220> FEATURE:
<223> OTHER INFORMATION: Tamapin V29L

<400> SEQUENCE: 543

```
Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Leu Pro Tyr
            20                  25                  30
```

<210> SEQ ID NO 544
<211> LENGTH: 31
<212> TYPE: PRT
<213> ORGANISM: Artificial Sequence
<220> FEATURE:
<223> OTHER INFORMATION: Tamapin V29M

<400> SEQUENCE: 544

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Met Pro Tyr
            20                  25                  30
```

<210> SEQ ID NO 545
<211> LENGTH: 31
<212> TYPE: PRT
<213> ORGANISM: Artificial Sequence
<220> FEATURE:
<223> OTHER INFORMATION: Tamapin V29N

<400> SEQUENCE: 545

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Asn Pro Tyr
            20                  25                  30
```

<210> SEQ ID NO 546
<211> LENGTH: 31
<212> TYPE: PRT
<213> ORGANISM: Artificial Sequence
<220> FEATURE:
<223> OTHER INFORMATION: Tamapin V29P

<400> SEQUENCE: 546

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Pro Pro Tyr
            20                  25                  30
```

<210> SEQ ID NO 547
<211> LENGTH: 31
<212> TYPE: PRT
<213> ORGANISM: Artificial Sequence
<220> FEATURE:
<223> OTHER INFORMATION: Tamapin V29Q

<400> SEQUENCE: 547

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Gln Pro Tyr
            20                  25                  30
```

<210> SEQ ID NO 548
<211> LENGTH: 31
<212> TYPE: PRT
<213> ORGANISM: Artificial Sequence
<220> FEATURE:
<223> OTHER INFORMATION: Tamapin V29R

<400> SEQUENCE: 548

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Arg Pro Tyr
            20                  25                  30
```

<210> SEQ ID NO 549
<211> LENGTH: 31
<212> TYPE: PRT
<213> ORGANISM: Artificial Sequence
<220> FEATURE:
<223> OTHER INFORMATION: Tamapin V29S

<400> SEQUENCE: 549

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Ser Pro Tyr
            20                  25                  30
```

<210> SEQ ID NO 550
<211> LENGTH: 31
<212> TYPE: PRT
<213> ORGANISM: Artificial Sequence
<220> FEATURE:
<223> OTHER INFORMATION: Tamapin V29T

<400> SEQUENCE: 550

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Thr Pro Tyr
            20                  25                  30
```

<210> SEQ ID NO 551
<211> LENGTH: 31
<212> TYPE: PRT
<213> ORGANISM: Artificial Sequence
<220> FEATURE:
<223> OTHER INFORMATION: Tamapin V29W

<400> SEQUENCE: 551

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Trp Pro Tyr
            20                  25                  30
```

<210> SEQ ID NO 552
<211> LENGTH: 31
<212> TYPE: PRT
<213> ORGANISM: Artificial Sequence
<220> FEATURE:
<223> OTHER INFORMATION: Tamapin V29Y

<400> SEQUENCE: 552

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Tyr Pro Tyr
            20                  25                  30
```

<210> SEQ ID NO 553
<211> LENGTH: 31
<212> TYPE: PRT
<213> ORGANISM: Artificial Sequence
<220> FEATURE:
<223> OTHER INFORMATION: Tamapin P30A

<400> SEQUENCE: 553

```
Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Ala Tyr
            20                  25                  30
```

<210> SEQ ID NO 554
<211> LENGTH: 31
<212> TYPE: PRT
<213> ORGANISM: Artificial Sequence
<220> FEATURE:
<223> OTHER INFORMATION: Tamapin P30C

<400> SEQUENCE: 554

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Cys Tyr
            20                  25                  30

<210> SEQ ID NO 555
<211> LENGTH: 31
<212> TYPE: PRT
<213> ORGANISM: Artificial Sequence
<220> FEATURE:
<223> OTHER INFORMATION: Tamapin P30D

<400> SEQUENCE: 555

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Asp Tyr
            20                  25                  30

<210> SEQ ID NO 556
<211> LENGTH: 31
<212> TYPE: PRT
<213> ORGANISM: Artificial Sequence
<220> FEATURE:
<223> OTHER INFORMATION: Tamapin P30E

<400> SEQUENCE: 556

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Glu Tyr
            20                  25                  30

<210> SEQ ID NO 557
<211> LENGTH: 31
<212> TYPE: PRT
<213> ORGANISM: Artificial Sequence
<220> FEATURE:
<223> OTHER INFORMATION: Tamapin P30F

<400> SEQUENCE: 557

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Phe Tyr
            20                  25                  30

<210> SEQ ID NO 558
<211> LENGTH: 31
<212> TYPE: PRT
<213> ORGANISM: Artificial Sequence
<220> FEATURE:
<223> OTHER INFORMATION: Tamapin P30G

<400> SEQUENCE: 558

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Gly Tyr
            20                  25                  30

<210> SEQ ID NO 559
<211> LENGTH: 31
<212> TYPE: PRT
<213> ORGANISM: Artificial Sequence
<220> FEATURE:
<223> OTHER INFORMATION: Tamapin P30H

<400> SEQUENCE: 559

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val His Tyr
            20                  25                  30

<210> SEQ ID NO 560
<211> LENGTH: 31
<212> TYPE: PRT
<213> ORGANISM: Artificial Sequence
<220> FEATURE:
<223> OTHER INFORMATION: Tamapin P30I

<400> SEQUENCE: 560

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Ile Tyr
            20                  25                  30

<210> SEQ ID NO 561
<211> LENGTH: 31
<212> TYPE: PRT
<213> ORGANISM: Artificial Sequence
<220> FEATURE:
<223> OTHER INFORMATION: Tamapin P30K

<400> SEQUENCE: 561

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Lys Tyr
            20                  25                  30

<210> SEQ ID NO 562
<211> LENGTH: 31
<212> TYPE: PRT
<213> ORGANISM: Artificial Sequence
<220> FEATURE:
<223> OTHER INFORMATION: Tamapin P30L

<400> SEQUENCE: 562

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Leu Tyr
            20                  25                  30

<210> SEQ ID NO 563
<211> LENGTH: 31
<212> TYPE: PRT
<213> ORGANISM: Artificial Sequence
<220> FEATURE:
<223> OTHER INFORMATION: Tamapin P30M

<400> SEQUENCE: 563

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Met Tyr
            20                  25                  30

<210> SEQ ID NO 564
<211> LENGTH: 31
<212> TYPE: PRT
<213> ORGANISM: Artificial Sequence
<220> FEATURE:

<223> OTHER INFORMATION: Tamapin P30N

<400> SEQUENCE: 564

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Asn Tyr
            20                  25                  30

<210> SEQ ID NO 565
<211> LENGTH: 31
<212> TYPE: PRT
<213> ORGANISM: Artificial Sequence
<220> FEATURE:
<223> OTHER INFORMATION: Tamapin P30Q

<400> SEQUENCE: 565

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Gln Tyr
            20                  25                  30

<210> SEQ ID NO 566
<211> LENGTH: 31
<212> TYPE: PRT
<213> ORGANISM: Artificial Sequence
<220> FEATURE:
<223> OTHER INFORMATION: Tamapin P30R

<400> SEQUENCE: 566

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Arg Tyr
            20                  25                  30

<210> SEQ ID NO 567
<211> LENGTH: 31
<212> TYPE: PRT
<213> ORGANISM: Artificial Sequence
<220> FEATURE:
<223> OTHER INFORMATION: Tamapin P30S

<400> SEQUENCE: 567

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Ser Tyr
            20                  25                  30

<210> SEQ ID NO 568
<211> LENGTH: 31
<212> TYPE: PRT
<213> ORGANISM: Artificial Sequence
<220> FEATURE:
<223> OTHER INFORMATION: Tamapin P30T

<400> SEQUENCE: 568

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Thr Tyr
            20                  25                  30

<210> SEQ ID NO 569
<211> LENGTH: 31
<212> TYPE: PRT
<213> ORGANISM: Artificial Sequence
<220> FEATURE:
<223> OTHER INFORMATION: Tamapin P30V

<400> SEQUENCE: 569

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Val Tyr
            20                  25                  30

<210> SEQ ID NO 570
<211> LENGTH: 31
<212> TYPE: PRT
<213> ORGANISM: Artificial Sequence
<220> FEATURE:
<223> OTHER INFORMATION: Tamapin P30W

<400> SEQUENCE: 570

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Trp Tyr
            20                  25                  30

<210> SEQ ID NO 571
<211> LENGTH: 31
<212> TYPE: PRT
<213> ORGANISM: Artificial Sequence
<220> FEATURE:
<223> OTHER INFORMATION: Tamapin P30Y

<400> SEQUENCE: 571

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Tyr Tyr
            20                  25                  30

<210> SEQ ID NO 572
<211> LENGTH: 31
<212> TYPE: PRT
<213> ORGANISM: Artificial Sequence
<220> FEATURE:
<223> OTHER INFORMATION: Tamapin Y31A

<400> SEQUENCE: 572

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Ala
            20                  25                  30

<210> SEQ ID NO 573
<211> LENGTH: 31
<212> TYPE: PRT
<213> ORGANISM: Artificial Sequence
<220> FEATURE:
<223> OTHER INFORMATION: Tamapin Y31C

<400> SEQUENCE: 573

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Cys
            20                  25                  30

<210> SEQ ID NO 574
<211> LENGTH: 31
<212> TYPE: PRT
<213> ORGANISM: Artificial Sequence
<220> FEATURE:
<223> OTHER INFORMATION: Tamapin Y31D

<400> SEQUENCE: 574

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Asp
            20                  25                  30

<210> SEQ ID NO 575
<211> LENGTH: 31
<212> TYPE: PRT
<213> ORGANISM: Artificial Sequence
<220> FEATURE:
<223> OTHER INFORMATION: Tamapin Y31E

<400> SEQUENCE: 575

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Glu
            20                  25                  30

<210> SEQ ID NO 576
<211> LENGTH: 31
<212> TYPE: PRT
<213> ORGANISM: Artificial Sequence
<220> FEATURE:
<223> OTHER INFORMATION: Tamapin Y31F

<400> SEQUENCE: 576

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Phe
            20                  25                  30

<210> SEQ ID NO 577
<211> LENGTH: 31
<212> TYPE: PRT
<213> ORGANISM: Artificial Sequence
<220> FEATURE:
<223> OTHER INFORMATION: Tamapin Y31G

<400> SEQUENCE: 577

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Gly
            20                  25                  30

<210> SEQ ID NO 578
<211> LENGTH: 31
<212> TYPE: PRT
<213> ORGANISM: Artificial Sequence
<220> FEATURE:
<223> OTHER INFORMATION: Tamapin Y31H

<400> SEQUENCE: 578

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro His
            20                  25                  30

```
<210> SEQ ID NO 579
<211> LENGTH: 31
<212> TYPE: PRT
<213> ORGANISM: Artificial Sequence
<220> FEATURE:
<223> OTHER INFORMATION: Tamapin Y31I

<400> SEQUENCE: 579

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Ile
            20                  25                  30

<210> SEQ ID NO 580
<211> LENGTH: 31
<212> TYPE: PRT
<213> ORGANISM: Artificial Sequence
<220> FEATURE:
<223> OTHER INFORMATION: Tamapin Y31K

<400> SEQUENCE: 580

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Lys
            20                  25                  30

<210> SEQ ID NO 581
<211> LENGTH: 31
<212> TYPE: PRT
<213> ORGANISM: Artificial Sequence
<220> FEATURE:
<223> OTHER INFORMATION: Tamapin Y31L

<400> SEQUENCE: 581

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Leu
            20                  25                  30

<210> SEQ ID NO 582
<211> LENGTH: 31
<212> TYPE: PRT
<213> ORGANISM: Artificial Sequence
<220> FEATURE:
<223> OTHER INFORMATION: Tamapin Y31M

<400> SEQUENCE: 582

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Met
            20                  25                  30

<210> SEQ ID NO 583
<211> LENGTH: 31
<212> TYPE: PRT
<213> ORGANISM: Artificial Sequence
<220> FEATURE:
<223> OTHER INFORMATION: Tamapin Y31N

<400> SEQUENCE: 583

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Asn
            20                  25                  30
```

```
<210> SEQ ID NO 584
<211> LENGTH: 31
<212> TYPE: PRT
<213> ORGANISM: Artificial Sequence
<220> FEATURE:
<223> OTHER INFORMATION: Tamapin Y31P

<400> SEQUENCE: 584

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Pro
            20                  25                  30

<210> SEQ ID NO 585
<211> LENGTH: 31
<212> TYPE: PRT
<213> ORGANISM: Artificial Sequence
<220> FEATURE:
<223> OTHER INFORMATION: Tamapin Y31Q

<400> SEQUENCE: 585

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Gln
            20                  25                  30

<210> SEQ ID NO 586
<211> LENGTH: 31
<212> TYPE: PRT
<213> ORGANISM: Artificial Sequence
<220> FEATURE:
<223> OTHER INFORMATION: Tamapin Y31R

<400> SEQUENCE: 586

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Arg
            20                  25                  30

<210> SEQ ID NO 587
<211> LENGTH: 31
<212> TYPE: PRT
<213> ORGANISM: Artificial Sequence
<220> FEATURE:
<223> OTHER INFORMATION: Tamapin Y31S

<400> SEQUENCE: 587

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Ser
            20                  25                  30

<210> SEQ ID NO 588
<211> LENGTH: 31
<212> TYPE: PRT
<213> ORGANISM: Artificial Sequence
<220> FEATURE:
<223> OTHER INFORMATION: Tamapin Y31T

<400> SEQUENCE: 588

Ala Phe Cys Asn Leu Arg Arg Cys Glu Leu Ser Cys Arg Ser Leu Gly
1               5                   10                  15
Leu Leu Gly Lys Cys Ile Gly Glu Glu Cys Lys Cys Val Pro Thr
            20                  25                  30
```

```
<210> SEQ ID NO 589
<211> LENGTH: 31
<212> TYPE: PRT
<213> ORGANISM: Artificial Sequence
<220> FEATURE:
<223> OTHER INFORMATION: Tamapin Y31V

<400> SEQUENCE: 589

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Val
            20                  25                  30

<210> SEQ ID NO 590
<211> LENGTH: 31
<212> TYPE: PRT
<213> ORGANISM: Artificial Sequence
<220> FEATURE:
<223> OTHER INFORMATION: Tamapin Y31W

<400> SEQUENCE: 590

Ala Phe Cys Asn Leu Arg Arg Cys Glu Leu Ser Cys Arg Ser Leu Gly
1               5                   10                  15

Leu Leu Gly Lys Cys Ile Gly Glu Glu Cys Lys Cys Val Pro Trp
            20                  25                  30
```